US012558432B2

(12) United States Patent
Geraths et al.

(10) Patent No.: US 12,558,432 B2
(45) Date of Patent: Feb. 24, 2026

(54) BIOCOMPATIBLE POLYMERIC DRUG CARRIERS FOR DELIVERING ACTIVE AGENTS

(71) Applicant: CIS BIOPHARMA AG, Bubendorf (CH)

(72) Inventors: Christian Geraths, Rheinfelden (DE); Christophe Thommen, Steinbrunn-le-Bas (FR); Michael Hackebeil, Gorwihl (DE); Davide Panighetti, Munchenstein (CH); Hans Hitz, Arisdorf (CH)

(73) Assignee: CIS BIOPHARMA AG, Bubendorf (CH)

( * ) Notice: Subject to any disclaimer, the term of this patent is extended or adjusted under 35 U.S.C. 154(b) by 781 days.

(21) Appl. No.: 17/771,996

(22) PCT Filed: Oct. 30, 2020

(86) PCT No.: PCT/EP2020/080545
§ 371 (c)(1),
(2) Date: Apr. 26, 2022

(87) PCT Pub. No.: WO2021/084087
PCT Pub. Date: May 6, 2021

(65) Prior Publication Data

US 2022/0409737 A1 Dec. 29, 2022

Related U.S. Application Data

(60) Provisional application No. 62/973,844, filed on Oct. 30, 2019.

(51) Int. Cl.

*A61K 47/68* (2017.01)
*A61K 47/58* (2017.01)
*A61K 51/06* (2006.01)
*A61K 51/10* (2006.01)

(52) U.S. Cl.

CPC .......... *A61K 47/6883* (2017.08); *A61K 47/58* (2017.08); *A61K 51/065* (2013.01); *A61K 51/1093* (2013.01)

(58) Field of Classification Search

CPC .. A61K 47/58; A61K 51/065; A61K 47/6883; A61K 51/1093

See application file for complete search history.

(56) References Cited

U.S. PATENT DOCUMENTS 5,508,269 A 4/1996 Smith et al.
5,767,068 A 6/1998 VanDevanter et al.
6,014,969 A 1/2000 Lloyd et al.
11,008,414 B2 * 5/2021 Geraths ............ B29D 11/00048
2009/0232871 A1 * 9/2009 Hitz ...................... C08F 220/20 526/321
2011/0262991 A1 * 10/2011 Raja ..................... A61K 49/085 435/235.1
2019/0224318 A1 7/2019 Yin et al.
2021/0128735 A1 * 5/2021 Geraths .................. A61K 47/64

FOREIGN PATENT DOCUMENTS

| | | |
|---|---|---|
| CA | 3016474 | 9/2017 |
| CA | 3066754 | 12/2018 |
| CA | 3075798 | 3/2019 |
| CA | 3096754 | 11/2019 |
| CA | 3117666 | 4/2020 |
| CA | 3121857 | 6/2020 |
| EP | 2 777 714 | 9/2017 |
| JP | 2019/528258 | 10/2019 |
| WO | WO 98/43650 | 10/1998 |
| WO | WO 03/053473 | 7/2003 |
| WO | WO2017/055536 | 4/2017 |
| WO | WO 2017/055536 A1 * | 4/2017 |
| WO | WO 2018/027164 | 2/2018 |
| WO | WO 2019/136866 | 7/2019 |

OTHER PUBLICATIONS

M. Talelli et al., "Synthesis and Characterization of Biodegradable and Thermosensitive Polymeric Micelles with Covalently Bound Doxorubicin-Glucuronide Prodrug via Click Chemistry," *Bioconjugate Chemistry*, 22(12):2519-2530 (2011).

P. Kitov et al., "Impact of the Nature and Size of the Polymeric Backbone on the Ability of Heterobifunctional Ligands to Mediate Shiga Toxin and Serum Amyloid P Component Ternary Complex Formation," *Toxins*, 3(9):1065-1088 (2011).

S. Périno et al., "Inhibition of angiogenesis by THAM-derived cotelomers endowed with thalidomide moieties," *Bioorganic & Medicinal Chem. Letters*, 14(2):421-425 (2004).

N. Berger et al., "Cancer in the Elderly," *Transactions of the American Clinical and Climatological Association*, 117:147-156 (2006).

R. Yancik, "Population Aging and Cancer: A Cross-National Concern," *The Cancer Journal*, 11:437-41 (2005).

Q. Zhou, "Site-Specific Antibody Conjugation for ADC and Beyond," *Biomedicines*, 5(4) (2017), pp. 1-15.

J. Reichert, "Antibodies to Watch in 2017," *MAbs*, 9(2):167-181 (2017).

A. Mullard, "Maturing antibody-drug conjugate pipeline hits 30," *Nature Reviews / Drug Discovery*, 12:329-333 (2013).

A. Beck et al., "Strategies and challenges for the next generation of antibody-drug conjugates," *Nature Reviews | Drug Discovery*, 16:315-337 (2017).

H. Yao et al., "Methods to Design and Synthesize Antibody-Drug Conjugates (ADCs)," *Int. J. Mol. Sci.*, 17(2):194 (2016), pp. 1-16.

(Continued)

*Primary Examiner* — Hong Yu
(74) *Attorney, Agent, or Firm* — Buscher Patent PLLC

(57) ABSTRACT

The present disclosure relates to the delivery of multiple copies of a payload molecule such as an active agent or a chelating agent capable of capturing an active agent, using as a carrier for their delivery a biocompatible copolymer comprising side chain-linked amino acids functionalized at their alpha-amino group by a reactive azide moiety by means of which the payload molecules are coupled to the copolymer. The copolymer is typically further functionalized to contain a single copy of a cell type- or tissue type-specific targeting moiety.

35 Claims, No Drawings

(56) References Cited

OTHER PUBLICATIONS

A. Beck et al., "The Next Generation of Antibody-drug Conjugates Comes of Age," *Discovery Medicine*, 10(53):329-39 (Oct. 2010).
S. Shaunak et al., "Site-specific PEGylation of native disulfide bonds in therapeutic proteins," *Nature Chemical Biology*, 2(6): 312-3 (Jun. 2006).
S. Balan et al., "Site-Specific PEGylation of Protein Disulfide Bonds Using a Three-Carbon Bridge," *Bioconjugate Chemistry*, 18(1):61-76 (2007).
A. Tolcher et al., "Randomized Phase II Study of BR96-Doxorubicin Conjugate in Patients with Metastatic Breast Cancer," *Journal of Clinical Oncology*, 17(2):478-478 (Feb. 1999).
S. Alley et al., "Contribution of Linker Stability to the Activities of Anticancer Immunoconjugates," *Bioconjugate Chemistry*, 19(3):759-765 (2008).
B. Shen et al., "Conjugation site modulates the in vivo stability and therapeutic activity of antibody-drug conjugates," *Nature Biotechnology*, 30(2):184-189 (Feb. 2012).
B. Kennedy et al., "Investigation of Optical Coherence Microelastography as a Method to Visualize Cancers in Human Breast Tissue," *Cancer Research*, 75(16 Supp.), Abstract DDT02-04 (Aug. 15, 2015).
N. Stefan et al., "Highly Potent, Anthracycline-based Antibody-Drug Conjugates Generated by Enzymatic, Site-specific Conjugation," *Molecular Cancer Therapeutics*, 16(5):879-892 (May 2017).
D. Bergstrom et al., "Non-clinical pharmacokinetics of XMT-1522, a HER2 targeting auristatin-based antibody drug conjugate"; poster presentation at the American Association for Cancer Research (AACR) annual meeting in Washington D.C., 2017.
M. Koitka et al., "Improving the ex vivo stability of drug ester compounds in rate and dog serum: Inhibition of the specific esterases and implications on their identity," *Journal of Pharmaceutical and Biomedical Analysis*, 51(3):664-678 (2010).
B. Li et al., "Butyrylcholinesterase, paraoxonase, and albumin esterase, but no carboxylesterase, are present in human plasma," *Biochemical Pharmacology*, 70(11):1673-1684 (2005).
M. Mercier et al., "Selection of Nucleic Acid Aptamers Targeting Tumor Cell-Surface Protein Biomarkers," *Cancers* (Basel), 9(6):E69 (2017), pp. 1-33.
A. Ruscito et al., "Small-Molecule Binding Aptamers: Selection Strategies, Characterization, and Applications," *Frontiers in Chemistry*, 4:14 (May 2016).
P. Ray et al., "Application of Aptamers for Targeted Therapeutics," *Archivum Immunologiae et Therapiae Experimentalis* 61(4):255-271, (2013).
X. Pei et al., "Clinical applications of nucleic acid aptamers in caner (Review)," *Molecular and Clinical Oncology*, 2(3):341-348 (2014).
G. Zhou et al., "Aptamers: A promising chemical antibody for cancer therapy," *Oncotarget*, 7(12):13446-63 (2016).
C. Biagi et al., "Comparative safety profiles of intravitreal bevacizumab, ranibizumab and pegaptanib: the analysis of the WHO database of adverse drug reactions," *Eur. J. Clin. Pharmacol.*, 70(12):1505-12 (2014).
D. Pozarowska et al., "The era of anti-vascular endothelial growth factor (VEGF) drugs in ophthalmology, VEGF and anti-VEGF therapy," *Cent. Eur. J. Immunol.*, 41(3):311-316 (2016).
R. Alvarez et al., "Biology of Platelet-Derived Growth Factor and Its Involvement in Disease," *Mayo Clin. Proc.*, 81(9):1241-57 (Sep. 2006).
V. Bagalkot et al., "An Aptamer-Doxorubicin Physical Conjugate as a Novel Targeted Drug-Delivery Platform," *Angew. Chem. Int., Ed.* 45(48):8149-8152 (2006).
N. Kolishetti et al., "Engineering of self-assembled nanoparticle platform for precisely controlled combination drug therapy," *PNAS*, USA, 107(42):17939-17944 (Oct. 19, 2010).
T. Chu et al., "Aptamer mediated siRNA delivery," *Nucleic Acids Research*, 34(10):e73 (2006), pp. 1-6.
N. Zia et al., "A Bivalent Inhibitor of Prostate Specific Membrane Antigen Radio-labeled with Copper-64 with High Tumor Uptake and Retention," *Angewandte Chemie*, 131:15133-15136 (2019).
J. Chiefari et al., "Living Free-Radical Polymerization by Reversible Addition-Fragmentation Chain Transfer: The RAFT Process," *Macromolecules*, 31(16):5559-5562 (1998).
D. Zbaida et al., "Design of Chiral Polymers for the Kinetic Resolution of Racemic Conglomerates," *Reactive Polymers, Ion Exchangers, Sorbents* 6(2-3):241-253 (1987).
R. Cozzi et al., "Structure analysis and site-directed mutagenesis of defined key residues and motives for pilus-related sortase C1 group B *Streptococcus*," *The FASEB Journal*, 25(6):1874-1886 (2011).
R. Beerli et al., "Sortase Enzyme-Mediated Generation of Site-Specifically Conjugated Antibody Drug Conjugates with High In Vitro and In Vivo Potency," PLOS ONE 10(7):e0131177 (Jul. 1, 2015), pp. 1-17.
I. Martins et al., "Transglutaminases: recent achievements and new sources," *Appl. Microbiol. Biotechnol.*, 98:6957-6964 (2014).
M. Ehrbar et al., "Biomolecular Hydrogels Formed and Degraded via Site-Specific Enzymatic Reactions," *Biomacromolecules*, 8(10):3000-3007 (2007).
A. Mero et al., "A new method to increase selectivity of transglutaminase mediated PEGylation of salmon calcitonin and human growth hormone," *Journal of Controlled Release*, 154(1):27-34 (2011).
D. Trentin et al., "Non-viral gene delivery for local and controlled DNA release," *Journal of Controlled Release*, 102(1):263-275 (2005).
M. Kieliszek et al., "Microbial transglutaminase and its application in the food industry. A review," *Folia Microbiol.*, 59:241-250 (2014).
A. Caporale et al., "The LQSP tetrapeptide is a new highly efficient substrate of microbial transglutaminase for the site-specific derivatization of peptides and proteins," *Biotechnology Journal*, 10(1):154-161 (2015).
R. Strickley, "Solubilizing Excipients in Oral and Injectable Formulations," *Pharmaceutical Research*, vol. 21, No. 2, pp. 201-230 (2004).
P. Dennler et al., "Transglutaminase-Based Chemo-Enzymatic Conjugation Approach Yields Homogeneous Antibody-Drug Conjugates," *Bioconjugate Chemistry*, 25:569-578 (2014).

* cited by examiner

BIOCOMPATIBLE POLYMERIC DRUG CARRIERS FOR DELIVERING ACTIVE AGENTS

FIELD OF THE INVENTION

The invention relates to the delivery of active agents, e.g., drug substances, using as carriers for their delivery biocompatible copolymers comprising side chain-linked amino acids to which active agents are bound either directly or via linker molecules.

BACKGROUND

Cancer is one of the major threats to human health and given the fact that its likelihood is a function of age, the case numbers will increase with the ageing of populations. Berger, N A et al. (2006) Cancer in the Elderly, Transactions of the American Clinical and Climatological Association 117: 147-156; Yancik, R (2005) Cancer J. 11: 437-41. In recent years, tumor therapies have made enormous improvements due to the use of tumor-specific agents such as monoclonal antibodies. These antibodies block proliferation signals such as the epidermal growth factor pathway (EGFR) (Cetuximab Erbitux®, Merck KGaA; / Panitumumab, Vectibix®, Amgen/Trastuzumab, Herceptin®, Roche) or prevent the formation of new blood vessels by targeting the vascular endothelial growth factor (VEGF) pathway (Bevacizumab, Avastin®, Roche) to slow tumor growth. Since their target antigens are usually over-expressed in tumor tissues, healthy cells are less impaired, wherefore antibody therapies have less off-target effects compared to conventional cytotoxic agents. Zhou, Q. (2017) Biomedicines 5(4); Reichert, J M (2017) MAbs 9: 167-181. The unique specificity of antibodies was also used for combination approaches aimed at targeting cytotoxic drugs to tumor cells. These so-called antibody drug conjugates (ADCs) have proven to be superior to monotherapies with antibodies or cytotoxic agents. Although known since the 1960s, the ADC concept has encountered interest in the pharmaceutical industry only relatively recently, and more than 60 ADCs are undergoing clinical trials. Mullard, A (2013) Nat Rev Drug Discov 12: 329; Beck, A et al. (2017) Nat Rev Drug Discov 16: 315-337.

The first generation of ADCs used free amino groups in the antibodies to attach cytotoxic drugs and drug linker constructs. With up to 80 free amino-groups per antibody, their indiscriminate functionalization leads to highly heterogeneous ADC species with different drug to antibody ratios (DAR) and affinities due to unintended attachment of cytotoxic drugs to the binding interface of the antibodies. The heterogeneity with respect to DARs could be restricted to a certain extent by adjusting the stoichiometry of drug and antibody used in the reaction. With respect to site specificity, heterogeneity was only limited by chemical accessibility when the first clinical trials were conducted. It took another 20 years for the FDA approval of the first ADC. The development of ADCs has dramatically increased since: 30 ADCs have been entering reactive groups. The latter heterogeneities were also the major issues and regulatory concerns with the first ADCs. Yao, H et al. (2016) Int J Mol Sci 17(2): 194. In addition, the first ADCs were based upon mouse immunoglobulins known to elicit important immune responses. Because of these drawbacks the first ADC generation failed to show much improvement over conventional therapies, so that gemtuzumab ozogamicin (Mylotarg®), the first FDA-approved ADC, was voluntarily withdrawn from the market by Pfizer in 2010. Beck, A et al. (2017) Nat Rev Drug Discov 16(5): 315-337; Beck, A et al. (2010) Discov Med 10(53): 329-39.

The second generation of ADCs mitigated the latter difficulties by targeting free thiol groups of humanized antibodies. These free thiol groups were generated prior to the coupling reaction by mild reduction (e.g., with 1,4-dithiothreitol (DTT)) of 4 inter-chain disulfide bridges in the hinge region of the antibodies. With this strategy, the potential attachment sites could be reduced to 8, resulting in a higher homogeneity of the ADCs. Given the fact that the inter-chain disulfide bonds play a crucial role in antibody integrity, the higher homogeneity was often paid for by negative effects on antibody stability. Although more specific linkers preserving disulfide bridge integrity were designed (as elaborated, e.g., in Shaunak, S et al. (2006) Nat Chem Biol 2(6): 312-3 and Balan, S et al. (2007) Bioconug Chem 18(1): 61-76), ADCs generated suffered from low DARs that were typically about 3-4. If the drug load was further increased, the stability of the antibodies was negatively affected, leading to rapid clearance from the blood stream. In addition, the affinity of the antibodies for their tumor cell-specific targets was negatively affected. Beck et al. (2017) Nat Rev Drug Discov 16(5): 315-337; Yao et al. (2016) Int J Mol Sci 17(2): 194.; Beck et al. (2010) Discov Med 10(53): 329-39. Since only a few cytotoxic entities were coupled to these antibodies, conventional cytotoxic agents like doxorubicin proved to be insufficiently effective in killing tumor cells. Tolcher, AW (1999) J Clin Oncol 17(2): 478-478. Therefore, novel classes of cytotoxic agents had to be used whose cytotoxicity was several orders of magnitudes higher. Examples for these substances are microtubule inhibitors such as mertansine (DM1) or monomethylauristatin E (MMAE). Beck et al. (2017). With such potent drug substances, it is crucial that the drug substances are only released from the ADCs at their target site. Otherwise, severe side effects are likely to result. The linker between the drug and the antibody plays thereby a major role. Recently marketed ADCs like Trastuzumab emtansine (Kadcyla®, Roche) and Brentuximab Vedotin (Adcetris®, Tekada Pharmaceutical) as well as the Mersana concept (Mersana Therapeutics Inc. (Cambridge, Mass.)) use maleimide-based linkers which are known to react with cysteine-bearing proteins, in particular serum albumin. Alley, S C et al. (2008) Bioconjug Chem 19(3): 759-765. Shen, B Q et al. (2012) Nat Biotechnol 30(2): 184-9.

The so-called third generation of ADCs made use of site-specific coupling of the drug to the antibody. A prominent example is Vadatuximab tailirine from Seattle Genetics against acute myeloid leukemia (AML). The ADC contains a genetically engineered cysteine at position 239 in both heavy chains which is used for coupling of pyrrolobenzodiazepine (PBD) dimer that is capable of crosslinking DNA, thereby blocking cell division and causing cell death. The ADC has been successfully tested in a phase I study and is currently in a phase III clinical trial. Beck et al. (2017); Kennedy, D A et al. (2015) Cancer Res 75(15 Supp.), Abstract DDT02-04. Other examples of site-specific coupling of drug to antibody make use of smart tags such as an "aldehyde-tag" (Redwood Biosciences, Catalent) or a "sortase tag" (SMAC-Technology™, NBE Therapeutics; Stefan, N et al. (2017) Mol Cancer Ther 16(5): 879-892). The latter two approaches introduce genetically engineered peptide tags in the antibody to function as specific motives for enzymatic coupling reactions. Third generation ADCs represent more homogeneous products with increased stability but still deliver only a few toxic entities per antibody.

To avoid this limitation, a novel approach that uses a polymeric carrier was recently developed by Mersana Therapeutics. This concept is based on the functionalization of a degradable carrier polymer (referred to as "Fleximers") with several cytotoxic drug molecules. The drug-loaded polymer is subsequently coupled to a monoclonal antibody by conventional linker chemistry. With this, the DAR could be increased to 12-15 drug molecules per antibody molecule, which drug molecules were distributed over 3-5 attached polymer carriers. "Non-clinical pharmacokinetics of XMT-1522, a HER2 targeting auristatin-based antibody drug conjugate"; poster presentation at the American Association for Cancer Research (AACR) annual meeting in Washington D.C, 2017. Although this approach has many advantages, the resulting ADC contain Fleximer polymers of variable chain length and drug load. In combination with the thiol-maleinimide linker chemistry that was used, the molecular weight of the ADCs vary to some extent. Further, the Fleximer polymer comprises biodegradable ester linkages, raising the issues of long-term storage and/or serum stability Koitka, M et al. (2010) J Pharm Biomed Anal 51(3): 664-78; Li, B et al. (2005) Biochem Pharmacol 70(11: 1673-84.

In addition to antibodies, other target-specific agents including aptamers have been elaborated for blocking or activating aberrant pathways to treat metabolic diseases and cancer. Aptamers are small single-stranded polynucleotides with a defined 3-dimensional conformation formed by Watson-Crick base-pairing. Due to their well-defined structure, they can be made to bind specific targets including isolated small molecules such as bacterial toxins or surface markers on cells with high affinity. Mercier, M C et al. (2017) Cancers (Basel) 9(6): E69; Ruscito, A et al. (2016) Front Chem 4:14. Aptamers are far smaller than antibodies, easier to produce and lack immunogenicity. Ray, P et al. (2013) Archivum Immunologiae et Therapiae Experimentalis 61(4): 255-271; Pei, X et al. (2014) Mol Clin Oncol 2(3): 341-348; Zhou, G et al. (2016) Oncotarget 7(12):13446-63. They are usually generated from a pool of up to $10^{15}$ random polynucleotides in an enrichment process that involves iterative binding, washing, and amplification steps. After each cycle, the aptamers with the highest target affinity are chosen for the next cycle. This leads to the selection of molecules with binding affinities in the nano- or even sub-nanomolar range after 10-12 cycles. This process is also known as systematic evolution of ligands by exponential enrichment (SELEX). Zhou, G et al. (2016). Analogous to antibodies, the first therapeutic aptamer approach aimed to block disease-related pathways through interaction with key proteins, receptors or metabolites. A prominent example is Macugen® (Pegaptanib; EyeTech Pharmaceuticals, Pfizer), the first FDA-approved aptamer therapeutic that entered the market in 2004. Macugen® is a 27 nucleotide-long RNA aptamer and is used in age-related macular degeneration (AMD), a serious eye disease causing blindness. AMD is characterized by abnormal formation of blood vessels due to elevated levels of growth factors. Macugen®'s target is $VEGF_{165}$ (isoform), a growth factor responsible for angiogenesis. Since this aptamer had only a short half-life due to fast renal clearance and degradation, it was bound to a 40 kDa PEG polymer to increase its overall size. In addition, some nucleotides were substituted with 2'-fluoro-pyrimidine und 2'-O-methyl-purine to avoid degradation by nucleases. Biagi, C et al. (2014) Eur J Clin Pharmacol 70(12): 1505-12; Pozarowska, D et al. (2016) Cent Eur J Immunol 41(3): 311-316. In contrast to anti-VEGF antibodies (e.g., Bevacizumab, Avastin®; Roche), Macugen® has never been used or licensed for the treatment of cancer due to poor performance in systemic applications, probably due to compensation of effects by bypass pathways (e.g., PDGF-B). Alvarez, R H et al. (2006) Mayo Clin Proc 81(9): 1241-57. Following improvements made in more recent years, several attempts were made to use aptamers not only for targeting and blocking but also as carriers for cytotoxic agents. Bagalkot and co-workers developed an aptamer-doxorubicine complex. However, this complex suffered from poor loading efficiency and rapid systemic clearance. Bagalkot, V et al. (2006) Angew Chem Int Ed 45(48): 8149-8152. In 2010, a different approach was developed based upon docetaxel/cisplatin-loaded PLGA-PEG nanoparticles. These particles were guided to prostate cancer cells by functionalization with A10, an aptamer targeting a tumor cell membrane protein. This rather complex drug delivery system showed promising results at least in in vitro experiments. Kolishetti, N et al. (2010) Proc Natl Acad Sci USA 107(42): 17939-17944. Aptamers were further tested for the delivery of several nucleotide-based therapeutics such as siRNA (short interfering RNAs typically designed to suppress specific gene expression). Chu, T C et al. (2006) Nucleic Acids Res 34(10): e73. Despite the development of many different approaches utilizing the targeting ability of aptamers for tumor treatment, until present aptamers suffer from poor loading capacity, serum instability and fast renal clearance, all of which properties limit their clinical application. None of these aptamer-drug conjugates or complexes have entered clinical phase III or the market. Zhou et al. (2016).

To overcome the above-mentioned shortcomings and increase the drug to antibody/aptamer ratio (DAR) while simultaneously preserving antibody/aptamer affinity for the respective target, a new strategy was developed that utilizes a biocompatible, hydrophilic, non-degradable copolymer as a carrier of active agents. The polymer can be made to carry a multiplicity (within limits, any desirable number) of active agent molecules. The copolymer can be coupled to a tumor-targeting moiety, e.g., a monoclonal antibody or an aptamer. This coupling can occur either prior to or subsequent to the loading of the copolymer with active agent or other payload. Due to its high hydrophilicity, the copolymer is capable of carrying even highly hydrophobic cytotoxic drugs while maintaining the pharmacokinetic properties of the respective antibody/aptamer.

The approach presented in this disclosure has the advantage that only one coupling site is needed to bind a multitude of active agent molecules to an antibody or aptamer molecule. By the use of site-specific coupling methods, e.g., enzymatic coupling reactions to peptide tags at the C-terminus of the heavy chains of an antibody, active agent-containing copolymer will be located at a suitable distance from the antibody's binding interface. With this approach, maximal affinity for the target tissue is preserved as well as a relatively homogenous product is obtained. The chosen linking strategy forms a stable peptide bond between copolymer and antibody/aptamer, which ensures high stability of the ADCs in the blood stream. Furthermore, the chosen design of the copolymers facilitates the coupling of two or more different active agents to the same copolymer molecule, enabling combination therapies. Once active agent (e.g., a cytotoxic drug in the cancer context) is released inside a targeted cell, e.g., a tumor cell, and the targeting moiety (e.g., an antibody or an aptamer) is degraded, the relatively small copolymer is believed to be removed from the body by renal clearance.

SUMMARY OF THE INVENTION

The present disclosure relates to a copolymer molecule containing multiple molecules of a first payload molecule as well as to methods for making this copolymer. The payload-carrying copolymer is made by (a) polymerization of a reaction mixture comprising (1) a co-principal monomer of formula I containing an azide moiety, Formula I

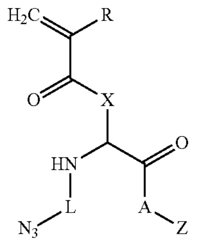

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—$CH(CH_3)$—, —S—$CH_2$— or —NH—$C_6H_4$—$CH_2$—; Z is H (if A is —O—) or —$C_nH_{2n+1}$ (with n=1-8); and A is —O— or —NH—; L is a linker/spacer which can be cleavable or non-cleavable under physiological conditions, (2) a polymerizable principal monomer, which monomer is characterized as having at least one vinylic group and not containing an amino acid moiety or an azide moiety, and (3) an initiator system for generating free radical species, the polymerization yielding a copolymer; and (b) coupling of the first payload molecules, typically functionalized with a click-reactive group, to the azide moieties contained in the copolymer of step (a), typically through a click reaction.

The term “amino acid moiety” refers to an amino acid is coupled through its reactive side chain to an acrylic moiety and contains functionalized or not-functionalized alpha-amino and alpha-carboxy functions. The term “azide moiety” refers to an azido group.

Preferably, the X moiety is attached to C(O)— moiety through its —NH—, —O—, or —S— group.

Within the scope of the present invention, the “initiator system for generating free radical species” is not meant to be particularly limited, and any such system known to the skilled person can be used. The examples are described herein. The term is also meant to encompass the use of UV radiation to generate free radical species.

As preferably understood herein, if A is —O—, then Z is H or —$C_nH_{2n+1}$ (with n=1-8), whereas if A is —NH—, Z is —$C_nH_{2n+1}$ (with n=1-8). Alternatively, Z can preferably also be defined as Z is H or —$C_nH_{2n+1}$ (with n=1-8). Preferably, if A is —O—, Z is preferably H.

The above reaction mixture can further comprise a co-principal monomer of formula II, Formula II

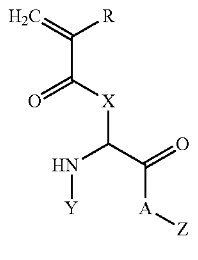

wherein R is —H, —$CH_3$, —$CH_2$—$CH_3$ or —$(CH_2)_2$—$CH_3$; X is —$NH(CH_2)_4$—, —$NH(CH_2)_3$—, —O—$CH_4$—$CH_2$—, —O—$CH_2$—, —O—$CH(CH_3)$—, —S—$CH_2$— or —NH—$CH_4$—$CH_2$—; Y is H or —CO—$C_nH_{2n+1}$ (with n=1-8); Z is H (if A is —O—) or —$C_nH_{2n+1}$ (with n=1-8); and A is —O— or —NH—, and/or a co-principal monomer of formula III, Formula III

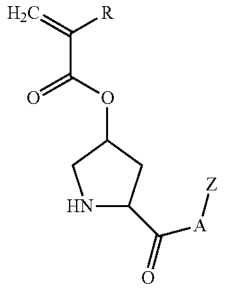

wherein: R is —H, —$CH_3$, —$CH_2$—$CH_3$ or —$(CH_2)_2$—$CH_3$; Z is H (if A is O) or —$C_nH_{2n+1}$ (with n=1-8); and A is —O— or —NH—.

As preferably understood herein, if A is —O—, then Z is H or —$C_nH_{2n+1}$ (with n=1-8), whereas if A is —NH—, Z is —$C_nH_{2n+1}$ (with n=1-8). Alternatively, Z can preferably also be defined as Z is H or —$C_nH_{2n+1}$ (with n=1-8). Preferably, if A is —O—, Z is preferably H.

An exemplary non-cleavable linker/spacer L of Formula I can be —CO—$C_nH_{2n}$ (with n=1-10) or —CO-$PEG_n$ (with n=1-14). Preferably, $PEG_n$ is herein understood as a moiety according to formula —$(OCH_2CH_2)$— or —$(CH_2CH_2O)_n$—. Cleavable linkers/spacers L of Formula I encompass cathepsin B-sensitive linkers such as dipeptide linkers, —CO-valine-citrulline-PABC or variants thereof, valine-lysine, valine-alanine, valine-arginine or tripeptide linkers such as glutamate-valine-citrulline, pH-sensitive linkers such as hydrazones or cis-aconityl-based linkers, linkers for lysosomal trafficking and cleavage such as pyrophosphate diesters. PABC is para-aniline-beta-carbamate. Variants are herein preferably defined as moieties wherein citrulline is replaced with another amino acid residue.

Copolymers that comprise monomers of formula I as well as formula II and/or III can be charged with two different payloads. A first payload, typically functionalized with a click-reactive group, is reacted with the azide moiety of monomers of formula I. The second payload, that is typically derivatized to contain a suitable reactive group, is joined to either the alpha-amino or alpha-carboxy group of the amino acid moiety of monomers of formulae II and III. This requires that in at least a fraction of the monomers of formulae II and/or III the alpha-amino or alpha-carboxy group or unfunctionalized (free), i.e., either or both of Y or Z in monomers of formula II are H, and/or Z in monomers of formula III is H. The copolymer of step (a) can be first loaded with the first payload and subsequently with the second payload. Alternatively, the copolymer of step (a) can be first loaded with the second payload and subsequently with the first payload. Therefore, preparation of the payload-carrying copolymer involves the polymerization step (a), the coupling step (b) and a further step in which second payload molecules containing a reactive group are coupled to co-principal monomers of formulae and/or III. The latter step can occur prior to or subsequent to step (b).

Depending on the structure of the active agent, active agent molecules may be reacted directly or indirectly via linker structures with the azide groups of co-principal monomers of formula I or the alpha-amino or alpha-carboxy groups of co-principle monomers of formulae and/or III in the copolymer. The latter linker should be stable during storage and in the blood stream to avoid unintended release of cytotoxic drug. The linker may be capable of being cleaved by specific intracellular enzymes or may be of a "non-degradable" type and only destroyed in the harsh environments of lysosomes and peroxisomes.

In preferred embodiments, the copolymer (of step (a)) is made by polymerization of a reaction mixture that further comprises a RAFT agent for controlling the copolymerization. The RAFT agent can contain a monodisperse spacer of 2-30 units. Furthermore, the RAFT agent may feature a reactive group that can be used, e.g., for the attachment to the copolymer of a cell type-specific or tissue type-specific targeting moiety. The latter reactive group can be a thiol, an aldehyde, an alkyne, an azide, an amine, a carboxyl, an ester, a diazirine, a phenyl azide, a thioester, a diazo, a Staudinger reactive phosphinoester (or phosphinothioester), a hydrazine, an oxime, an acrylate to perform aza-Micheal ligations, or a motif capable of being used in an enzymatic coupling reaction. The motif can be an oligo-glycine comprising 2-8 amino acids, which peptide motif enables sortase-mediated coupling reactions, a transglutaminase reactive substrate, an aldehyde tag, an autocatalytic intein sequence, or a click-reactive group. Alternatively, the RAFT agent may be capable of being converted subsequent to polymerization to provide a reactive group for attachment of a cell type-specific or tissue type-specific targeting moiety to the copolymer. Generally, RAFT agent is inactivated once polymerization and/or functionalization has been completed, whereby the elimination of the RAFT group is performed by thermal treatment, reaction with suitable amines (aminolysis), or a new reaction with an initiator molecule in the presence of a phosphorus oxoacid or with excess of initiator without phosphorus oxoacid.

Preparation of a copolymer (step (a)) can also involve two successive polymerization reactions. A first reaction mixture can comprise a polymerizable principal monomer not containing an amino acid group or an azide moiety, a RAFT agent for controlling the copolymerization, and an initiator system for generating free radical species, the polymerization yielding a RAFT pre-polymer. A second polymerization reaction is carried out in a second reaction mixture comprising the RAFT pre-polymer of the first polymerization reaction, a co-principle monomer of formulae I and an initiator system for generating free radical species. The second reaction mixture can further comprise a co-principal monomer of one or both of formulae and III and/or a polymerizable principal monomer not containing an amino acid moiety or an azide moiety.

A copolymer of the present disclosure is typically further functionalized with a cell type-specific or a tissue type-specific targeting moiety. The targeting moiety can be attached to the copolymer either prior to or subsequent to its functionalization with first and/or second payload molecules, i.e., prior to or subsequent to step (b) or the step involving coupling of second payload molecules to co-principal monomers of formulae and/or III.

Potential targeting moieties are, but are not limited to, monoclonal antibodies, antibody fragments, nano-bodies (single-domain-antibodies), DARPins (designed ankyrin repeat proteins), peptide hormones, proteins binding to proteins expressed on the tumor cell surface, DNA- or RNA-based aptamers, or small molecules capable of binding to cell surface receptors that are known to be over-expressed in tumor cells, e.g., folic acid or biotin. The covalent attachment of the targeting moiety is carried out in a site-specific manor, typically involving a reactive group in the copolymer's head group (that typically is introduced via a RAFT agent or by conversion of the mentioned RAFT agent). Suitable coupling strategies include the so-called "click-chemistry reaction" using a reactive group (e.g. an strained alkyne in case of a [3+2] cycloaddition or a strained alkene for a [4+2] cycloaddition) at the copolymer's head group which is subsequently used to bind the cell type-specific or a tissue type-specific targeting moiety containing the "counter part" of the click reaction (such as azide for [3+2]cycloaddition or tetrazine for [4+2] cycloaddition). The above-mentioned reactive parts of the click reaction are meant to be interchangeable. The "click reactions" used to modify the copolymer with payload molecules and to attach a targeting moiety to the copolymer may be carried out in a sequential manner or "in parallel" by the use of orthogonal compatible click reactions, e.g. a combination of [3+2] cycloaddition and [4+2] cycloaddition reactions. Usually the modification of the targeting moiety with the counter part of the click reaction should be performed in a site-directed manner, e.g., by the use of enzymatic coupling techniques like transglutaminase-mediated or sortase-mediated coupling or by integration of non-canonical (unnatural) amino acids into the targeting moiety during synthesis or post synthesis.

In different embodiments, an enzymatic coupling reaction may also be used to modify the cell- or tissue-type specific targeting moiety directly with the copolymer containing multiple payload molecules. This is done by modification of the polymer's head group with a suitable tag, e.g., an oligo-glycine for sortase-mediated coupling, aldehyde tags, or transglutaminase tags. In case of a transglutaminase-mediated reaction, the copolymer's head group introduced by a suitable chain transfer agent may comprise a peptide motif containing a reactive lysine (or glutamine) residue or a non-peptide motif, e.g., a linker structure containing a terminal amino group. The latter head group modification may especially be used in combination with microbial transglutaminases, which are known to accept non-peptide motifs with high turnover rates.

A payload molecule may be an active agent or a chelating agent. In the case of a payload-carrying copolymer of the present disclosure in which the payload is a chelating agent, the copolymer is incubated or exposed with an active agent that is capable of being captured by the chelating agent. Preferably, the situation wherein the copolymer is exposed with an active agent refers to contacting the copolymer with an active agent, as disclosed herein. Use of a chelating agent as a payload molecule may be particularly advantageous in the case of short-lived radioisotopes which may be bound to the payload-carrying copolymer immediately prior to diagnostic or therapeutic use.

For clarity, terms used above and in the claims such as "a co-principal monomer of formula I", "a principal monomer", "a co-principal monomer of formula II", "a RAFT agent", and "an initiator system" are not meant to refer to numbers of molecules of a type. The singular is meant to also include the plural. For example, the term "a co-principal monomer of formula I" is meant to indicate the presence of amounts of one or more chemically different compounds that satisfy the requirements of formula I.

In any of the above-described copolymers carrying multiple payload molecules, the copolymers have average molecular weights of 5,000 Daltons to 80,000 Daltons. More preferably, the copolymers have average molecular weights of 5,000 Daltons to 40,000 Daltons. Most preferably, the copolymers have average molecular weights of 5,000 Daltons to 20,000 Daltons. These molecular weights do not include the weight of a coupled targeting moiety. Average molecular weights of the copolymers in this invention are preferably understood as the number average molecular weight which are calculated based on measurements of size exclusion chromatography (SEC)/gel permeation chromatography (GPC) by comparison with a known molecular weight standard, herein different pullulan polymers. For details see the method presented in example 13. In the alternative or in addition, in any of the above-described copolymers carrying multiple payload molecules, at least 80% (w) of the copolymer molecules have an average molecular weight of 5,000 Daltons to 80,000 Daltons. More preferably, at least 80% (w) of the copolymer molecules have an average molecular weight of 5,000 Daltons to 40,000 Daltons. Most preferably, at least 80% (w) of the copolymer molecules have an average molecular weight of 5,000 Daltons to 20,000 Daltons. The presented percentage portions in the last paragraph are thereby a consequence of the polydispersion index (PDI) of the copolymers. The dispersity (D), also referred to as the polydispersity index (PDI) or heterogeneity index, is a measure of the distribution of molecular mass in a given polymer sample. D (PDI) of a polymer is defined by PDI the formula =Mw/Mn, wherein Mw is the weight average molecular weight and Mn is number average molecular weight as measured by gel permeation chromatography using a known polymer as a reference standard. The dispersity indicates the distribution of individual molecular masses in a batch of polymers. PDIs of the copolymers in this invention are typically in the range of 1.03 to 1.4, preferable in the range of 1.05 to 1.35, more preferably in the range of 1.1 to 1.30 and most preferably in the range of 1.15 to 1.25. PDI is characterized by methods presented in example 13, unless stated otherwise.

Preferably, in copolymers that contain co-principal monomers of formula I as the only co-principal monomers, the average number of co-principal monomers is from 2-12. More preferably, the copolymers contain, on average, from 2-8 co-principle monomers, and, most preferably, from 2-6 co-principle monomers. For copolymers that also contain co-principal monomers of formula II and/or formula III that are not functionalized, the preferred average number of all co-principal monomers is from 10-50. More preferred is an average number of co-principal monomers of 10-40 and most preferred is an average number of co-principal monomers of 10-30. If the co-principal monomers of formula II and/or formula III are functionalized with payload molecules, the preferred average number of all co-principal monomers is from 4-20. More preferred is an average number of co-principal monomers of 4-15 and most preferred is an average number of co-principal monomers of 4-10. As understood herein, the term "functionalized" relates to the attachment of a second payload molecule(s) to the monomer(s) of formula II and/or of formula III. If the monomers are not functionalized, it is to be understood that they do not contain the second payload molecule(s). In other words the second payload molecule(s) are not attached thereto.

If the payload molecule contained in a copolymer of the present disclosure is an active agent, this active agent can be a microtubule inhibitor, an intercalating agent, an alkylating agent, an antimetabolite, a hormone or hormone receptor modulation agent, a tyrosine kinase inhibitor, a polynucleotide-based drug capable of interfering with a gene or its respective messenger RNA, a protein-based bacterial toxin, an enzyme suitable for prodrug therapy (ADEPT concept), or a radioisotope. The active agent can also be a tracer molecule including a small molecule fluorophore, a protein/peptide-based fluorophore, a near infrared (NIR) fluorescent probe, a bioluminescent probe, a radiocontrast agent, or a radioisotope.

The present invention preferably further encompasses a copolymer containing multiple copies of a first payload molecule obtainable by (a) polymerization of a reaction mixture comprising (1) a monomer of formula II, (II)

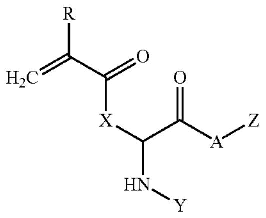

wherein R is —H, —$CH_3$, —$CH_2$—$CH_3$ or —$(CH_2)_2$—$CH_3$; X is —$NH(CH_2)_4$—, —$NH(CH_2)_3$—, —O—$CH_4$—$CH_2$—, —O—$CH_2$—, —O—$CH(CH_3)$—, —S—$CH_2$— or —NH—$CH_4$—$CH_2$—; Y is H; Z is H (if A is —O—) or —$C_nH_{2n+1}$ wherein n=1-8; and A is —O— or —NH—, (2) a monomer having at least one vinylic group and not containing an amino acid moiety or an azide moiety, and (3) an initiator system for generating free radical species, the polymerization yielding a copolymer;

(b) treating the copolymer of step (a) with an amine reactive agent containing a linker/spacer L and an azide moiety, and (c) coupling of the first payload molecules to the azide moieties contained in the copolymer of step (b).

Alternatively, Y may also be defined as H or —$C_nH_{2n+1}B$ (with n=1-8), wherein B is H or OH, preferably Y is H. As preferably understood herein, if A is —O—, then Z is H or —$C_nH_{2n+1}$ (with n=1-8), whereas if A is —NH—, Z is —$C_nH_{2n+1}$ (with n=1-8). Alternatively, Z can preferably also be defined as Z is H or —$C_nH_{2n+1}$ (with n=1-8). Preferably, if A is —O—, Z is preferably H.

The above reaction mixture can be further preferably supplemented with a monomer of formula III, (III)

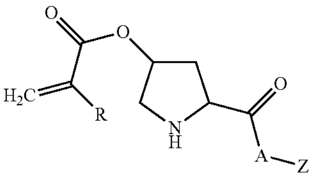

wherein: R is —H, —$CH_3$, —$CH_2$—$CH_3$ or —$(CH_2)_2$—$CH_3$; Z is H (if A is O) or —$C_nH_{2n+1}$ (with n=1-8); and A is —O— or —NH—.

As preferably understood herein, if A is —O—, then Z is H or —$C_nH_{2n+1}$ (with n=1-8), whereas if A is —NH—, Z is —$C_nH_{2n+1}$ (with n=1-8). Alternatively, Z can preferably also be defined as Z is H or —$C_nH_{2n+1}$ (with n=1-8). Preferably, if A is —O—, Z is preferably H.

Further preferably, the present invention relates to a copolymer comprising a repeating unit of formula (R1a)

(R1a)

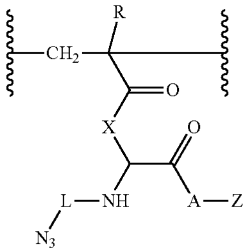

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—$CH(CH_3)$—, —S—$CH_2$— or —NH—$C_6H_4$—$CH_2$—; Z is H (if A is —O—) or —$C_nH_{2n+1}$ (with n=1-8); and A is —O— or —NH—, L is a linker/spacer. L is as defined herein. The polymer as defined herein is obtainable according to the methods of the present invention.

As preferably understood herein, if A is —O—, then Z is H or —$C_nH_{2n+1}$ (with n=1-8), whereas if A is —NH—, Z is —$C_nH_{2n+1}$ (with n=1-8). Alternatively, Z can preferably also be defined as Z is H or —$C_nH_{2n+1}$ (with n=1-8). Preferably, if A is —O—, Z is preferably H.

Further preferably, the present invention relates to a copolymer comprising a repeating unit of a formula (R1)

(R1)

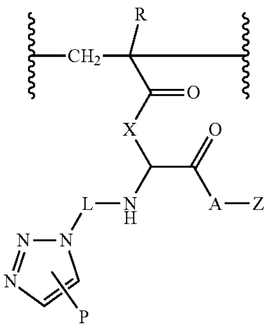

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—$CH(CH_3)$—, —S—$CH_2$— or —NH—$CH_4$—$CH_2$—; Z is H (if A is —O—) or —$C_nH_{2n+1}$ (with n=1-8); and A is —O— or —NH—; L is a linker/spacer, and P comprises a first payload molecule. L and payload molecule are as defined in the present disclosure.

As preferably understood herein, if A is —O—, then Z is H or —$C_nH_{2n+1}$ (with n=1-8), whereas if A is —NH—, Z is —$C_nH_{2n+1}$ (with n=1-8). Alternatively, Z can preferably also be defined as Z is H or —$C_nH_{2n+1}$ (with n=1-8). Preferably, if A is —O—, Z is preferably H.

Preferably, the copolymer comprising the repeating unit of formula (R1a) or the copolymer comprising the repeating unit of formula (R1), further comprise a repeating unit of formula (R2):

(R2)

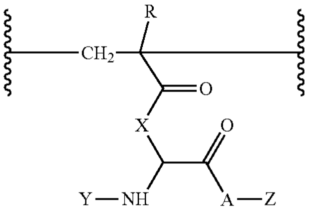

wherein R is —H, —$CH_3$, —$CH_2$—$CH_3$ or —$(CH_2)_2$—$CH_3$; X is —$NH(CH_2)_4$—, —$NH(CH_2)_3$—, —O—$CH_4$—$CH_2$—, —O—$CH_2$—, —O—$CH(CH_3)$—, —S—$CH_2$— or —NH—$CH_4$—$CH_2$—; Y is H or —CO—$C_nH_{2n+1}$ (with n=1-8) or Y comprises a second payload molecule; Z is H (if A is —O—) or —$C_nH_{2n+1}$ (with n=1-8), or Z comprises a second payload molecule; and A is —O— or —NH—, and/or a repeating unit of formula (R3):

(R3)

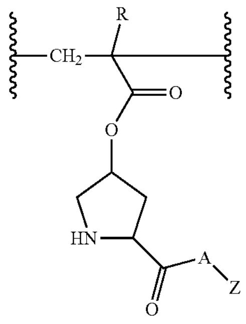

wherein: R is —H, —$CH_3$, —$CH_2$—$CH_3$ or —$(CH_2)_2$—$CH_3$; Z is H (if A is O) or —$C_nH_{2n+1}$ (with n=1-8), or Z comprises a second payload molecule; and A is —O— or —NH—.

As preferably understood herein, if A is —O—, then Z is H or —$C_nH_{2n+1}$ (with n=1-8), whereas if A is —NH—, Z is —$C_nH_{2n+1}$ (with n=1-8). Alternatively, Z can preferably also be defined as Z is H or —$C_nH_{2n+1}$ (with n=1-8). Preferably, if A is —O—, Z is preferably H.

Preferably, Z can be H and/or Y can be H. Alternatively, Z and/or Y can comprise a second payload molecule. The payload molecule is as defined herein. Alternatively, in certain embodiments, Z is H or —$C_nH_{2n+1}$ (with n=1-8), or Z comprises a second payload molecule.

Further preferably, the copolymer of the present invention, comprises a repeating unit obtainable by polymerization of N,N-dimethyl-acrylamide, N-isobutyl-acrylamide, N-tert. butyl-acrylamide, N-hydroxyethyl-acrylamide, N-(2-hydroxypropyl)-acrylamide, N-(3-hydroxypropyl)-acrylamide, N-(3-hydroxypropyl)-methacrylamide, N-(2-hydroxypropyl)-methacrylamide, N-(3-aminopropyl)-acrylamide hydrochloride, or N-(3-aminopropyl)-methacrylamide hydrochloride, or a repeating unit obtained through polymerization of methacrylic acid, 2-hydroxyethyl-acrylate, 2-hydroxypropyl-acrylate, 3-hydroxypropyl-acrylate, 2-hydroxy-1-methylethyl-acrylate, 2-aminoethyl acrylate hydrochloride, 3-hydroxypropyl-methacrylate, 2-hydroxy-1-methylethyl-methacrylate, 2-hydroxyethyl-methacrylate, 2-hydroxypropyl-methacrylate or 2-aminoethyl methacrylate hydrochloride.

Further preferably, in the copolymer of the present invention, wherein the repeating units of formulae (R2) and (R3) are absent, the average number of repeating units according to formula (R1) per molecule of copolymer is 2 to 12, preferably 2 to 8, more preferably 2 to 6.

Further preferably, in the copolymer of the present invention, wherein the repeating units of formulae (R2) or (R3) are not functionalized, as defined herein, the average number of repeating units according to formulae (R1), (R2) or (R3) per molecule of copolymer is 10 to 50, preferably 10 to 40, more preferably 10 to 30.

Further preferably, in the copolymer of the present invention, wherein the repeating units of formulae (R2) or (R3) are functionalized with a second payload molecule, the average number of repeating units according to formulae (R1), (R2) or (R3) per molecule of copolymer is 4 to 20, preferably 4 to 15, more preferably 4 to 10.

The present disclosure also relates to pharmaceutical compositions comprising an effective amount of a copolymer of the present disclosure containing multiple molecules of a covalently bound active agent or of an active agent that is captured by a chelating agent that is covalently bound and a carrier. Depending on the nature of the active agent, these compositions may be used in the treatment of various cancers or of other diseases/conditions.

The present disclosure also encompasses methods of treatment of different types of cancers or other diseases and conditions comprising administration of a pharmaceutical composition comprising an effective amount of a copolymer of the present disclosure containing multiple molecules of a covalently bound active agent or of an active agent that is captured by a chelating agent that is covalently bound and a carrier (also referred to herein as "active moiety"). Within the scope of the present disclosure are also uses of pharmaceutical compositions comprising an effective amount of a copolymer of the present disclosure containing multiple molecules of a covalently bound active agent or of an active agent that is captured by a chelating agent that is covalently bound and a carrier for the treatment of a cancer or another disease or condition in a subject, comprising administering to the subject an effective amount of the copolymer.

The present invention further preferably relates to use of the copolymer of the present invention in therapy, wherein the copolymer comprises a first payload molecule and a second payload molecule, and wherein the first payload molecule and a second payload molecule are two active agents to be administered together as a combination therapy.

The present invention further preferably relates to the copolymer of the present invention for use in diagnostic application, preferably in monitoring of cancer. Preferably the monitoring of cancer is performed simultaneously with cancer therapy. Preferably, the copolymer comprises the radionuclide useful in diagnosis, as disclosed herein.

DETAILED DESCRIPTION OF THE INVENTION

Unless otherwise defined, all terms shall have their ordinary meaning in the relevant art. The following terms are defined and shall have the following meanings:

As used herein, "pharmaceutically acceptable carrier or excipient" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in Remington's Pharmaceutical Sciences (Mack Publishing Co., Easton, Pa., 19th ed. 1995), a standard reference text in the field, which is incorporated herein by reference. Non-limiting examples of materials which can serve as pharmaceutically acceptable carriers are sugars such as lactose, glucose and sucrose; cyclodextrins such as alpha-, beta- and gamma-cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Also encompassed are emulsifiers/surfactants such as cremophor EL and solutol HS15, lecithin and phospholipids such as phosphatylcholine. Liposomes may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "subject" as used herein refers to a mammalian subject. Preferably, the subject is a human subject.

The term "active moiety" relates to a copolymer of the present disclosure containing multiple molecules of a payload molecule (which copolymer may be further functionalized with a cell type-specific or tissue type-specific targeting moiety), whereby, if the payload molecule is a chelating agent, the term refers to a copolymer that also contains an active agent that has been captured by the chelating agent.

The term "cell type-specific or tissue type-specific targeting moiety" in the context of this disclosure refers to a molecule that binds to a surface marker on cells of a specific type or on cells of a particular tissue with an avidity, that renders it useful for the delivery to the cells of a cargo active agent. It can be a monoclonal antibody, a single-domain, variable fragment of an antibody chain, a single-chain antibody, a DARPin (Designed Ankyrin Repeat Protein), a DNA- or RNA-based aptamer, a peptide-based aptamer, a peptide or protein capable of binding a cell surface marker, a hormone, or a small molecule capable of binding a cell surface marker.

A "tracing molecule" is defined as a molecule that is capable of producing a readout signal in a diagnostic or scientific application. It can be a small molecule fluorophore, a protein/peptide-based fluorophore, a near infrared (NIR) fluorescent probe, a bioluminescent probe, a radiocontrast agent, or a radioisotope.

By an "effective amount" of an active moiety of the disclosure is meant an amount of the active moiety which, when administered once or multiple times over the course of a treatment, confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of an active moiety of the disclosure is an amount of the active moiety that comprises an active agent preferably in an amount ranging from about 0.01 mg/kg body weight of a subject to about 50 mg/kg body weight, and more preferably from about 0.1 to about 30 mg/kg body weight. Effective doses will also vary depending on route of administration, as well as the possibility of co-usage with other agents. It will be understood, however, that the total daily usage of the active moiety and pharmaceutical compositions of the present disclosure will be decided by the attending physician within the scope of sound medical judgment. The specific effective dose level for any particular patient will depend upon a variety of factors including the disorder being treated and the severity of the disorder; the activity of the specific active agent employed; the specific composition employed; the age, body weight, general health, sex and diet of the patient; the time of administration, route of administration and rate of excretion of the specific active moiety employed; the duration of the treatment; drugs used in combination or contemporaneously with the specific active moiety employed; and like factors well known in the medical arts. It is noted that when used in the context of prophylaxis or prevention, an “effective amount” of an active moiety of the disclosure is meant to be an amount of the active moiety which, when administered once or multiple times over the course of a treatment, confers a desired prophylactic effect on the treated subject.

The term “payload molecule” or “payload” refers either to an active agent that is covalently linked to a copolymer, directly or via a linker, or to a chelating agent that is covalently linked to a copolymer and that is capable of capturing an active agent. Chelating agents that are covalently coupled to a copolymer can be used to immobilize radioisotopes. Chelating agents include, but are not limited to, (1,4,7,10)-Tetraazacyclododecane-1,4,7,10-tetraacetic acid [DOTA], 2,2',2"-(10-(2,6-Dioxotetrahydro-2H-pyran-3-yl)-1,4,7,10-tetraazacyclododecane-1,4,7-triyl)triacetic acid [DOTA-GA], 1,4,7-Triazacyclononane-N,N',N"-triacetic acid [NOTA], 1,4,8,11-Tetraazacyclotetradecane-1,4,8,11-tetraacetic acid) [TETA], Diethylene-triamine-pentaacetic anhydride [DTPA] and sarcophagine chelators like Sar (see Nicholas et al. 2019, Angewandte Chemie 131: 15133-15136).

The term “active agent” means a therapeutically active substance, which is bound to copolymers of this disclosure. In the context of cancer therapy, the active agent typically is a cytotoxic substance/molecule. Example cytotoxic substance/molecules include microtubule inhibitors such as monomethyl auristatin E (MMAE) or emtansine (DM1), intercalating drugs, e.g., doxorubicin, alkylating agents such as cyclophosphamide (CP), antimetabolites such as 5-fluorouracil (5-FU), hormones or hormone receptor modulation agents such as tamoxifen citrate, tyrosine kinase inhibitors such as Afatinib or Bosutinib, peptide-based toxins, e.g. α-amanitin, immune checkpoint inhibitors such as Nivolumab® or Pembrolizumab®, enzymes suitable for antibody-directed enzyme prodrug therapy (ADEPT), polynucleotide-based drugs capable of interfering with a gene(s) or its respective messenger RNA (siRNA, microRNA or antisense-RNA) and radioisotopes such as, but not limited to, fluorine-18, copper-64, gallium-68, zirconium-89, indium-111, iodine-123, (diagnostic application) or copper-67, strontium-89, yttrium-90, iodine-131, samarium-153, lutetium-177, radium-223 and actinium-225 (therapeutic application). Further example active agent include scandium-43, scandium-44, terbium-152, and terbium-155 (diagnostic application) or scandium-47 terbium-149, and terbium-161 (therapeutic application). Some of the listed radionuclides are suitable for diagnostic and therapeutic applications. E.g. terbium-161 could be used as a therapeutic agent but has due to its γ-emmission also some visibility with gamma cameras, or terbium-149 which can be used for targeted alpha therapy and has visibility in PET scans. Furthermore the here presented radionuclides could also be combined having a “theranostic-tandem” for visualization of biodistribution in a therapeutic approach.

The term “active agent” also encompasses radioisotopes/radionuclides that are typically coupled to a co-principle monomer of a copolymer by means of a chelating agent that is covalently linked to the monomer.

The terms “radioisotope/radionuclide” in the scope of this invention are preferably used synonymically and preferably represent an atom that has excess nuclear energy, making it unstable. This excess energy can be used in one of three ways: emitted from the nucleus as gamma radiation; transferred to one of its electrons to release it as a conversion electron; or used to create and emit a new particle (alpha particle or beta particle) from the nucleus. Radioisotope/radionuclide is herein preferably defined as an isotope which has a half-life of less than $10^{19}$ years.

The term “active agent” further encompasses substances capable of overcoming tumor cell resistance, e.g., by inhibiting an anti-apoptotic factor such as Bcl-2 or targeting a cellular efflux pump (such as the MDR-1 transporter), or anti-inflammatory substances including corticosteroids, glucocorticoids and nonsteroidal anti-inflammatory drugs (e.g., prostaglandins) that are useful for reducing inflammation-related therapy side effects.

The term “amine reactive agent” preferably relates to a moiety that can react with an amino group, thereby attaching to it by a covalent bond.

The term “copy” relates preferably to multiple, i.e. more than one, instances of a molecule, wherein more than one instances of the molecule have the same chemical structure.

A “monomer” means a low molecular weight compound that can be polymerized. For co-principal monomers of formulae I-III, or for principal monomers, low molecular weight typically means a molecular weight of less than 800 Daltons. When referred to in the context of a copolymer, the term “monomer” refers to the smallest building blocks of the copolymer.

The term “repeating unit” preferably relates to a bivalent substructure that is repeated multiple times in a (homo- or co-)polymer. Typically, in the polymers obtainable by (co) polymerization of monomers containing double bond, the points of attachment of the repeating unit correspond to atoms connected by the said double bond. In other words, repeating unit is derived from a monomer by its inclusion in the polymer.

The terms “RAFT agent” and “RAFT process” are preferably not particularly limited and may refer to any type of reversible addition-fragmentation chain transfer. The terms “RAFT agent” and “RAFT process” involve conventional free radical polymerization of a monomer in the presence of a suitable chain transfer agent (CTA). Commonly used RAFT agents include thiocarbonylthio compounds such as dithioesters, dithiocarbamates, trithiocarbonates and xanthates, which agents mediate the polymerization via a reversible chain-transfer process. Chiefari, J. et al. (1998) Macromolecules 31(16): 5559-62.

The term “pre-polymer” relates to a short polymer headed by a RAFT agent and comprising 10-25 units of a hydrophilic principal monomer, e.g., dimethyl-acrylamide. Such pre-polymers represent water-soluble macro-RAFT agents that are used in a second polymerization reaction to synthesize copolymers of principal and co-principal monomers in an aqueous environment.

The terms “substrate, motif or tag” or “reactive substrate, motif or tag” are used interchangeably to relate to chemical structures being able to take part in an enzymatically catalyzed reaction. These chemical structures are recognized by the active center of an enzyme and may intermediately form a covalent or electrostatic enzyme-substrate complex before the enzymatic catalyzed reaction takes place. In the context of the present disclosure, these reactions are often used to mediate the covalent attachment of a copolymer of this disclosure to a tumor cell or tissue-specific targeting moiety. Typical substrates, motifs and tags are defined sequences of amino acids or peptides, reactive functional groups like amino, thiol or carboxyl groups or unsaturated carbon bonds in a flexible spacer region of the copolymer’s head group.

The term “polymer analogous reaction” is preferably defined as deliberate changes of functional groups that are carried in macromolecular chains with the general objective of maintaining the polymerization degree of the original macromolecules.

The term “antibody-drug conjugate”, abbreviated “ADC”, represents a combination of an antibody that targets cell type- or tissue type-specific antigens (including tumor antigens) with a drug molecule or a multitude of drug molecules wherein the drug molecules are covalently attached to the antibody. In the context of the present disclosure, ADC refers to a conjugate of a cell type- or tissue type-specific antigen-targeting antibody with a copolymer displaying multiple molecules of an active agent of the present disclosure. As discussed, the copolymer of the present disclosure carries a multitude of active agent molecules or a combination of different active agent molecules that are covalently bound, via a linker or directly, to azide, alpha-amino and alpha-carboxy groups in the co-principal monomers. It can also carry a multitude of chelating agents that are covalently bound, via a linker or directly, to azide, alpha-amino and alpha-carboxy groups in co-principal monomers and which chelating agents capture active agent molecules.

The term “antibody radionuclide conjugate” (ARC) is preferably defined as a variant of an ADC where the “drug molecule or active molecule” represents a radionuclide/radioisotope either covalently bound to the antibody-polymer-conjugate e.g. in case of radioactive iodine or by a metal chelator complex e.g. with radioactive luthetium, actinium or terbium. The so formed ARC is capable to deliver a high amount of radiation to the tumor tissue thereby killing the tumor cells due to the damaging of DNA, essential enzymes etc.

The term “aptamer” is defined as follows: aptamers are oligonucleotide or peptide molecules that bind to a specific target molecule. Aptamers are usually created by selecting them from a large random sequence pool in an iterative enrichment process to identify the aptamer sequence with the highest target affinity. This process is also known as “systematic evolution of ligands by exponential enrichment (SELEX)”. More specifically, aptamers can be classified as DNA, RNA, xeno nucleic acid (XNA) (a synthetic alternative to natural nucleic acids that differs in the sugar backbone) or peptide aptamers. Aptamers consist of (usually short) strands of oligonucleotides or sequences of amino acids. The oligonucleotide sequence can thereby be formed of one kind of nucleotide, e.g., DNA, or a combination of different nucleotide types, e.g., DNA, RNA and or specially designed so called “locked-nucleotides” having their ribose moiety modified with an extra bridge connecting the 2' oxygen and 4' carbon. Aptamers in this disclosure also means peptide aptamers consisting of one (or more) short peptide domains.

The term “aptamer-drug conjugate” means a combination of an aptamer with an active agent molecule or different active agent molecules. In the context of the present disclosure, the active agent molecules are attached to copolymers either prior to or subsequent to the coupling of the copolymer to the aptamer.

The term “enhanced permeability and retention (EPR) effect” is used to describe the abnormal molecular and fluid transport dynamics in tumor tissue, especially for macromolecular drugs. Molecules of certain sizes (typically liposomes, nanoparticles, and macromolecular drugs) tend to accumulate in tumor tissue at higher levels than in normal tissues. The general explanation that is given for this phenomenon is that, in order for tumor cells to grow quickly, they must stimulate the production of blood vessels. The newly formed tumor vessels are usually abnormal in form and architecture and are permeable for molecules of higher molecular weight. Furthermore, tumor tissues usually lack effective lymphatic drainage so that, once a molecule has entered the tumor tissue, it is not effectively removed from this tissue.

The term “side chain-linked amino acid” in the context of a co-principal monomer means that an amino acid is covalently linked through its side chain (e.g., through an ester or amide linkage) to a moiety containing an acryloyl group. Monomers of formulae I to III contain side chain-linked amino acids.

The terms “principal monomer” and “co-principal monomer” are used mainly to facilitate the description of the invention. Principal monomers refer to monomers that do not include an amino acid moiety, i.e., a functionalized or not-functionalized amino acid, or an azide group, and co-principal monomers refer to monomers that do contain an amino acid moiety. Preferably, the terms “principal monomer” or “polymerizable principal monomer” are used interchangeably with the term “monomer having at least one vinylic group and not containing an amino acid moiety or an azide moiety” or “monomer not containing an amino acid moiety or an azide moiety”. Preferably, the terms “principle” and “principal” are used interchangeably herein.

Side chain-linked amino acids that can be present in co-principal monomers of the present disclosure include lysine (K), tyrosine (Y), serine (S), threonine (T), cysteine (C), 4-hydroxyproline (HO—P), ornithine (ORN) and 4-amino-phenylalanine (HOX). The amino acids can be the L or the D forms, or racemic mixtures. In the copolymers, a single type of side chain-linked amino acid or multiple types of side chain-linked amino acids may be present. For example, a copolymer can comprise both acryloyl-L-lysine (AK) and acryloyl-L-threonine (AT). For the sake of clarity, all monomers described by formulae I-III include a side chain-linked amino acid. The monomers of formula I are functionalized at the alpha-amino group of the amino acid with an azide group. The monomers of formulae and III can be unfunctionalized or can be functionalized at the alpha-amino and/or alpha carboxy-groups of the amino acid moieties they contain. The amino acid-containing copolymers of this disclosure comprise one or more polymerizable principal monomers, which monomers are characterized as having at least one vinylic group but not containing an amino acid residue or azide residue, one or more co-principal monomers according to any of formula I and, optionally, one or more co-principal monomers of formula and/or formula III.

Preferably, in copolymers that only contain co-principal monomers of formula I, the average number of co-principal monomers is from 2-12. More preferably, the copolymers contain, on average, from 2-8 co-principle monomers, and, most preferably, from 2-6 co-principle monomers. For copolymers that also contain co-principal monomers of formula and/or formula III that are not functionalized, the preferred average number of all co-principal monomers is from 10-50. More preferred is an average number of co-principal monomers of 10-40 and most preferred is an average number of co-principal monomers of 10-30. If the co-principal monomers of formula and/or formula III are functionalized, the preferred average number of all co-principal monomers is from 4-20. More preferred is an average number of co-principal monomers of 4-15 and most preferred is an average number of co-principal monomers of 4-10.

The synthesis of monomers containing side chain-linked amino acids was described previously. Zbaida, D et al. (1987) Reactive Polymers, Ion Exchangers, Sorbents 6(2-3): 241-253. Such monomers can be prepared by reacting the amino acid copper complex of lysine, tyrosine, serine, threonine, cysteine, ornithine, 4-amino-phenylalanine or 4-hydroxyproline with either acryloyl chloride, methacryloyl chloride, ethyl-acryloyl chloride or propyl-acryloyl chloride, followed by treatment with a stream of hydrogen sulfide gas or an acidic solution of sodium sulfide to yield the unprotected monomer. Syntheses are disclosed in international patent application publication WO2017/055536 and under Examples.

In particular embodiments, the principle monomers are derivatives of acrylamide and include dimethyl-acrylamide, N-isobutyl-acrylamide, N-tert. butyl-acrylamide, N-hydroxyethyl-acrylamide, N-(2-Hydroxypropyl)-acrylamide, N-(3-Hydroxypropyl)-acrylamide, N-(3-Hydroxypropyl)-methacrylamide, N-(2-Hydroxypropyl)-methacrylamide, N-(3-Aminopropyl)-acrylamide hydrochloride, or N-(3-Aminopropyl)-methacrylamide hydrochloride. Herein, dimethyl acrylamide is preferably understood as N,N-dimethylacrylamide. Preferably, the principle monomer as understood herein is also referred to as a monomer having at least one vinylic group and not containing an amino acid moiety or an azide moiety.

In other particular embodiments, the principle monomers are derivatives of acrylic acid including meth-acrylic acid 2-hydroxyethyl-acrylate, 2-hydroxypropyl-acrylate, 3-hydroxypropyl-acrylate, 2-hydroxy-1-methylethyl-acrylate, 2-aminoethyl acrylate hydrochloride, 3-hydroxypropyl-methacrylate, 2-hydroxy-1-methylethyl-methacrylate, 2-hydroxyethyl-methacrylate, 2-hydroxypropyl-methacrylate and 2-aminoethyl methacrylate hydrochloride. Preferably, the principle monomer as understood herein is also referred to as a monomer having at least one vinylic group and not containing an amino acid moiety or an azide moiety.

Copolymers comprising one or more types of co-principal monomers of formulae I and, optionally, of formula II and/or formula III are typically prepared in a radical polymerization reaction. It is important that copolymers of this disclosure have a narrow size distribution because in various therapies, in particular in cancer therapies, the drug load has to be precisely controlled. If it is not carefully controlled, overdosing or under-dosing effects may be encountered. To obtain copolymers with a narrow size distribution, the number of free radicals in the polymerization process has to be controlled. This can be achieved by the use of polymerization techniques including atom transfer radial polymerization (ATRP), nitroxide-mediated polymerization (NMP) or reversible addition-fragmentation-chain transfer polymerization (RAFT polymerization). RAFT is the most preferred technique for the copolymers described herein as it is compatible with a broad spectrum of monomers, especially acrylics, and can be easily performed in aqueous systems. Furthermore, RAFT polymerization can be used for the synthesis of block copolymers. In addition, the RAFT group can be used to add a reactive moiety to a polymer's head group (e.g., for conjugation with an antibody or aptamer). The RAFT technology was invented by a research group of the Commonwealth Scientific and Industrial Research Organization (CSIRO). Chiefari et al. (1998). Control of the chain size distribution is achieved via chain transfer reactions from the growing polymer chain to a chain transfer agent. A so-called RAFT agent forms an intermediate and is able to fragment into a radical on the propagating chain (designated as R-group) and a stabilizing moiety (designated as Z-group). As a consequence, the number of radicals is limited, and all growing polymer chains have a similar likelihood of propagation, resulting in copolymers with a narrow size distribution. Typical poly-dispersion indices (PDIs) [defined as Mw/Mn, where Mw is the weight-average molar mass and Mn is the number-average molar mass of the polymer] obtained in RAFT polymerizations are in the range of 1.05 to 1.4. Suitable RAFT agents are thiocarbonylthio compounds. Thiocarbonylthio compounds can be divided into four main classes, i.e., dithiobenzoates, trithiocarbonates, dithiocarbamates, and xanthates.

A typical polymerization mixture of this disclosure comprises therefore principal and co-principal monomers, a RAFT agent, and a radical initiator, preferably also referred to as "initiator system for generating free radical species". The mixture is then poured into a suitable container, wherein polymerization is induced. Initiators can be thermal initiators, e.g., VA-044 that is destabilized at elevated temperature to produce reactive radicals, redox initiators or photo initiators. Preferred redox initiators for polymerization in aqueous solution are peroxides, e.g., ammonium persulfate or potassium persulfate in combination with sodium thiosulfate, or azo-type compounds, for instance 2,2'-Azobis[2-(2-imidazolin-2-yl)propane]dihydrochloride or 4,4'-Azobis(4-cyanovaleric acid). For polymerization reactions in non-aqueous solvents, initiators/catalysts of the azo-type, e.g., Azobis(isobutyronitrile (AIBN), 1,1'-Azobis(cyclohexane-1-carbonitrile), 2,2'-Azobis(4-methoxy-2,4-dimethylvaleronitrile) are preferred. Polymer-modified azo-type initiators e.g., (polydimethylsiloxane, polyethylenglycol) can also be utilized. The above-mentioned initiators are usually destabilized at higher temperatures leading to the formation of reactive radicals.

Alternatively, the monomers can be photo-polymerized in a container that is transparent to radiation of a wavelength capable of initiating polymerization of the vinylic or acrylic monomers. Suitable photoinitiator compounds could be from type I, e.g., α-amino alkylphenones, or type II, e.g., benzophenones. Photosensitizers that permit the use of longer wavelengths can also be utilized. Depending on the initiator compound used, polymerization is initiated by heating, radiation or addition of a catalyst. In some embodiments of this disclosure, it is useful to synthesize a macro-RAFT or RAFT pre-polymer composed of 10-25 monomer units of a hydrophilic principal monomer prior to the polymerization of the copolymers (containing a mixture of principal and co-principal monomers). With this, the hydrophilicity of the often-hydrophobic RAFT agents can be enhanced, facilitating polymerization reactions in an aqueous environment.

In other embodiments, the RAFT agent itself is chemically modified by the integration of a water-soluble monodisperse polyethylene glycol (PEG) spacer of 3-25 units. Preferably, PEG spacer is herein understood as a moiety according to formula-$(OCH_2CH_2)_n$— or —$(CH_2CH_2O)_n$— wherein n is an integer from 3 to 25. The modified RAFT agent exhibits an improved water solubility and enables the synthesis of hydrophilic amino acid-containing copolymers in one polymerization step.

In other embodiments it may be useful to generate the co-principal building blocks of formula I in a polymer analogous reaction. For this, first a RAFT copolymer is prepared according to the above presented procedures with the exception that the monomer mixture is composed solely of a principal monomer and one or more monomers of formula II, and optionally one or more monomers of formula III. After purification of the copolymer and removal of the RAFT group the copolymer is treated with an amine reactive agent containing a linker and an azide group, thereby generating a copolymer with azide groups in the sidechain. For the sake of clarity the resulting copolymer of this polymer analogous reaction has an identical structure as copolymers generated by copolymerization including monomers of formula I. In order to synthesize a copolymer having different sidechain groups e.g. a mixture of formula I and II and/or III may be synthesized by variation of the molar ratio of the presented amine reactive azide in the polymer analogous reaction with the result that not all amino groups in the copolymers sidechain are converted.

Since the RAFT agent is known to be unstable in the presence of amines and is responsible for a strong odor of the obtained copolymers, it should usually be inactivated once the polymerization and functionalization process is completed. Preferred methods for RAFT group inactivation in this disclosure are reactions with nucleophiles, thermal elimination, or a second reaction with an initiator in combination with a proton-donating agent or an excess of a functionalized initiator.

Since the copolymers of this disclosure are intended to be used for drug delivery in a patient, it is generally preferable to purify the copolymers after polymerization or after functionalization (i.e., coupling of payload, targeting moiety, etc.). This step removes potentially harmful ingredients including residual initiators, monomers or catalysts. Preferred purification methods for copolymers of this invention are dialysis, tangential flow filtration and capillary ultrafiltration.

It is noted that defining useful parameter values does not require undue effort both because the number of parameters is limited and preferred ranges of some parametric values are known. The level of co-principal monomers in an amino acid-containing copolymer will be between about 2% (mol) and 95% (mol), preferably between about 3% (mol) and 40% (mol), and most preferably between 4% (mol) and 25% (mol) of all monomers present in the polymerization mixture. The average molecular weight of the amino acid-containing copolymer (without cell type- or tissue type-specific targeting moiety) will generally be between about 5,000 and 80,000 Daltons, preferably between about 5,000 and 40,000 Da, and most preferably between about 5,000 and 20,000 Da. The number of co-principal monomers a copolymer of the present disclosure can contain have been discussed above for three scenarios, i.e., for copolymers that contain monomers of formula I as the only type of monomers, for copolymers that contain monomers of formula I as well as formulae and/or III whereby only the monomers for formula I as functionalized (coupled to a first payload) subsequent to polymerization and for similar copolymers in which all coprincipal monomers are functionalized (coupled to first and second payloads).

As understood herein, the term "level of a monomer" in relation to a particular type of monomer is preferably defined as a ratio between the number of repeating units due to the monomers of a particular type to the number of repeating units due to all the monomers in the molecule of the (co)polymer. The level as understood herein is preferably expressed in percent values.

Once copolymerization has been completed, a copolymer of this invention comprising co-principal monomers of formula I is ready for functionalization with active agent molecules and/or a cell type-specific or a tissue type-specific targeting moiety (e.g., an antibody). This functionalization results in the establishment of covalent bonds between copolymer and active agent molecules and/or targeting moiety. In the case of certain active agents, e.g., certain radioisotopes, the copolymer is functionalized with a chelating agent, and the active agent is held by the chelating agent. It is noted that depending on the nature of the particular active agent to be joined to the copolymer, the copolymer may be functionalized with a cell type-specific or a tissue type-specific targeting moiety prior to the introduction of the active agent, or the active agent may be joined to the copolymer prior to functionalization with the targeting moiety.

Co-principal monomers of formula I contain an azide moiety. The azide moiety is a highly reactive entity being used for so called "click reactions" with alkynes. In contrast to amine or thiol addition reactions, the azide-alkyne or tetrazine-transcylcooctene click reactions are fast and highly selective. Indeed, no side reactions are encountered with addition reactions due to the presence of amino and thiol groups in the biological environment (peptides, proteins), making the azide group a perfect choice for drug delivery applications due to its orthogonal reactivity. Furthermore, monomers containing side chain-linked amino acids and (co)polymers that include an appropriate proportion of such monomers (at least 2 mol %) have the advantage of low toxicity. For example, the acryloyl-lysine monomer and (co)polymers containing this monomer do not exhibit any toxic effects in cell culture experiments at concentrations of up to 5 mM. Hence, ideal drug carriers can be designed by functionalization of acryloyl-lysine or other side chain linked amino acids with an azido group, providing biocompatible copolymers with low toxicity potential. In the field of antibody drug conjugates (ADCs) highly toxic drugs are often used, making the preparation of such ADCs expensive and challenging from a safety perspective. With this disclosure a side reactive carrier copolymer is introduced which can be coupled to an antibody to generate a "drug reactive" antibody polymer conjugate. The cytotoxic payload (i.e., a cytotoxic drug or chelating agent holding a cytotoxic drug) is coupled to the conjugate in the last phase of production. Therefore, the number of production steps and downstream process in which a high potency (HIPO) substances is present can be reduced. Furthermore, the here presented technology offers a high degree of flexibility since the payload could also be coupled to the polymeric carrier prior to the attachment of the antibody. This can be especially useful for antibodies or other cancer cell-specific targeting moieties that are sensitive to degradation.

Copolymers of the present disclosure can also include co-principal monomers of formulae II and/or III. The latter co-principal monomers contain side chain-linked amino acids that contain free or functionalized alpha-amino and/or carboxy groups. Copolymers including azide-containing monomers of formula I and monomers of formulae II and/or III in which at least one of the alpha-amino or carboxy groups are unfunctionalized enable "one-pot" coupling of an antibody with two different payload molecules. For example, a first payload molecule, e.g., a chelator for radioisotopes is functionalized with an azide-reactive moiety (e.g., a strained alkyne) and a second payload molecule, e.g., a cytotoxic drug is functionalized with an amine-reactive group (e.g., an NHS ester). This enables drug carriers for powerful combination therapies without the risk of side reactions and "mis-labelling" since both reactions are orthogonal. Furthermore, the number of reaction and purification steps such as dialysis can be reduced which is useful for sensitive and highly potent payload molecules. Furthermore, in cancer therapy applications, the here presented combination approach enables the copolymer to be loaded with cytotoxic agents and diagnostic radioisotopes and therefore to be traceable. The delivery of the cytotoxic agent to even a small tumor metastasis could be followed by positron emission tomography (PET) at high resolution, providing useful information on therapy progression.

The hydrophilic/hydrophobic balance of the cancer cell-specific targeting moiety in an antibody drug or polymer conjugate is crucial for the shelf life and circulation time of the construct since aggregation tends to reduce both shelf life and circulation time, leading to reduced therapy efficacy. Use of a polymeric drug carrier is expected to reduce the risk of aggregation induced by highly hydrophobic payloads such as certain anti-cancer drugs, since the drugs are linked to the carrier rather than directly to the antibody. However, this positive effect may be attenuated or even canceled by the far higher drug load enabled by the use of a drug carrier. In some embodiments of the copolymers of the present disclosure, the latter problem is counteracted by the inclusion in the copolymers of unfunctionalized co-principal monomers of formulae II and/or III. Hence, azide-functionalized side chain linked amino acids such as acryloyl-lysine-azide are used for coupling of payloads to the carrier copolymer, and highly hydrophilic unmodified side chain linked amino acids such as acryloyl-lysine enable an improved "solubility" of hydrophobic payloads. The overall "hydrophobicity" of the hydrophobic payload-loaded polymeric carrier is reduced and with it the potential for aggregation.

In particular embodiments, an active agent (here a cytotoxic drug or molecule used in cancer therapy) can be a microtubule inhibitor such as monomethyl auristatin E (MMAE) or emtansine (DM1); an intercalating drug, e.g., doxorubicin; an alkylating agent such as cyclophosphamide (CP); an antimetabolite such as 5-fluorouracil (5-FU); a hormone or hormone receptor modulation agent such as tamoxifen citrate; a tyrosine kinase inhibitor such as Afatinib or Bosutinib; a peptide-based toxin, e.g., α-amanitin; an immune checkpoint inhibitor such as Nivolumab® or Pembrolizumab®; an enzyme suitable for antibody-directed enzyme prodrug therapy (ADEPT); a polynucleotide-based drug capable of interfering with a gene(s) or its respective messenger RNA, siRNA, microRNA or antisense-RNA; or a radioisotope such as, but not limited to, fluorine-18, copper-64, gallium-68, zirconium-89, indium-111, iodine-123 (diagnostic application) or copper-67, strontium-89, yttrium-90, iodine-131, samarium-153, lutetium-177, radium-223 and actinium 225 (therapeutic application).

In particular embodiments, an active agent (here a cytotoxic drug or molecule used in cancer therapy) can be radioisotopes/radionuclides such as, but not limited to, fluorine-18, scandium-43, scandium-44, copper-61, copper-64, gallium-68, zirconium-89, indium-111, iodine-123, terbium-152, terbium-155 (diagnostic application) or scandium-47, copper-67, strontium-89, yttrium-90, iodine-131, terbium-149, samarium-153, terbium-161, lutetium-177, radium-223 and actinium-225 (therapeutic application).

The present inventors have surprisingly found that the copolymers according to the present invention comprising the first payload molecule and the second payload molecule, wherein first payload molecule and the second payload molecule are active agents useful in the combination therapy, are useful in co-delivering both active agents to the same cancer cell. Thecytotoxic payload can preferably be an agent which has in addition to its cytotoxic potential, an effect on the "radio-sensitivity" of the cancer cells e.g. by inhibition of DNA repair mechanisms (e.g. protein kinase inhibitors) or by targeting DNA strains directly (e.g. by intercalation like in the case of doxurubicin). Such an agent is herein preferably referred to as "radio-sensitizer". In this context such "radio-sensitizer" is useful in an combination therapy with a radionuclide since the cell killing effect of the radiation therapy is intensified. The here disclosed carrier technology has thereby the advantage that both agents can be bound to the same carrier molecule and coupled the same cancer cell specific targeting moiety to ensure "co-delivery" to the same cancer cell. For example, a first payload molecule, e.g., a chelator for radioisotopes is functionalized with an azide-reactive moiety (e.g., a strained alkyne) and a second payload molecule, e.g., a cytotoxic drug is functionalized with an amine-reactive group (e.g., an NHS ester).

Preferably, the radiosensitizer as understood herein for combined application with radioisotope is a kinase inhibitor, preferably selected from alisertib, MK-1775, MK-2206, saracatinib and temsirolimus, more preferably selected from alisertib and MK-2206. Preferably, the radioisotope as understood herein for combined application with radiosensitizer is selected from lutetium-177 and terbium-161. Thus, preferably, withing the scope of the present invention the radiosensitizer and radioisotope for combined application are selected from alisertib and lutetium-177, alisertib and terbium-161, MK-2206 and lutetium-177, and MK-2206 and terbium-161.

As understood herein, alisertib is the compound according to formula:

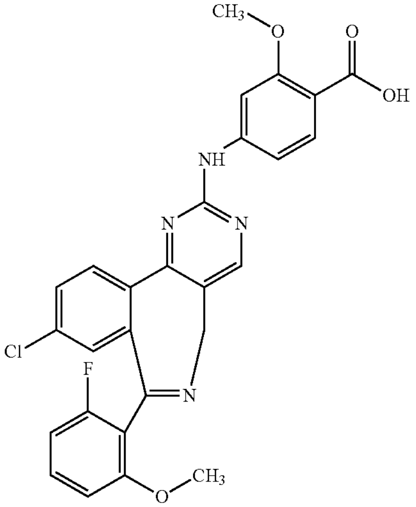 [SMILES: COc1cc(Nc2ncc3c(n2)-c2ccc(Cl)cc2C(c2c(F)cccc2OC)=NC3)ccc1C(=O)O]

which can be comprised in the copolymer of the present invention for example by attachment through a peptide bond formed by its carboxylic group.

As understood herein, MK-2206 is the compound according to the formula:

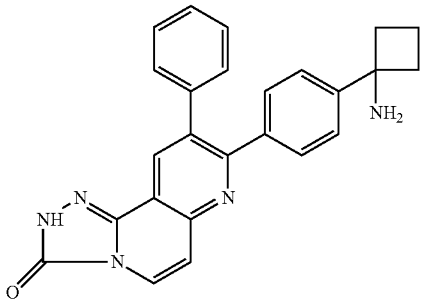 [SMILES: NC1(c2ccc(-c3nc4ccn5c(=O)[nH]nc5c4cc3-c3ccccc3)cc2)CCC1]

which can be comprised in the copolymer of the present invention for example by attachment through a peptide bond formed by its amino group. The present inventors have further surprisingly found that the copolymers of the present invention are suitable for diagnostic applications, as well as combined diagnostic and therapeutic applications. The combined diagnostic and therapeutic application may also be referred to as theranostic application. Preferably according to the present invention, the copolymer of the present invention may comprise a cell-type-specific or tissue-specific targeting moiety, for example an antibody targeting to a particular type of cancer cells, and a payload molecule being a chelating agent with a radionuclide. Certain radionuclides as disclosed herein, can be monitored, for example terbium 161 due to its γ-emmission can be visualized with gamma camera and hence used for detection of cancer tissue or cell-type, as targeted to by the antibody. Terbium-149 which can be used for targeted alpha therapy, has visibility in PET scans and thus can be monitored. According to the present disclosure, fluorine-18, scandium-43, scandium-44, copper-61, copper-64, gallium-68, zirconium-89, indium-111, iodine-123, terbium-152, terbium-155 are particularly useful in diagnostic application as described herein and may be referred to as radionuclides useful in diagnosis. As known to the skilled person, the radionuclides useful in diagnosis can be monitored by using a suitable method, for example Scintigraphy, Single Photon Emission Computed Tomography (SPE-CT); or Positron emission thomography Computed Tomography (PET-CT). Such use of the copolymer according to the present invention allows preferably for monitoring of biodistribution of the copolymer. Biodistribution of a copolymer is herein understood as distribution within the tissues of a subject, preferably of a patient, upon dosing with the said compolymer. The skilled person will appreciate that such copolymer wherein the active agent comprises a radionuclide useful for therapeutic application, for example selected from copper-67, strontium-89, yttrium-90, iodine-131, samarium-153, lutetium-177, radium-223 and actinium 225, (these radionuclides may be referred to as radionuclides useful in therapy) will have substantially the same biodistribution as the copolymer wherein the radionuclide is useful for diagnostic application. Therefore, according to the present invention, the copolymers of the present invention can preferably be used for monitoring of biodistribution of therapeutic copolymers during therapy. For example, a copolymer comprising an active agent being a radionuclide useful in therapy can be supplemented for this purpose preferably with less than 10 weight % of a copolymer wherein the payload comprises a radionuclide useful in diagnosis, as defined herein. Further preferably, the copolymer of the present invention for use in the combined therapeutic and diagnostic application may comprise two radionuclides, one radionuclide useful in therapy and one radionuclide useful in diagnosis, for example comprised within a first and a second payload molecule, respectively. Preferable are combinations wherein a radionuclide useful in therapy and a radionucleide useful in diagnosis are isotopes of the same element. Therefore, preferred combinations include scandium-43 and scandium-47, copper-61 and copper-67, copper-64 and copper-67, iodine-123 and iodine-131, terbium-152 and terbium-161, and terbium-155 and terbium-161. Further preferred combinations include isotopes of two different elements, for example indium-111 and lutetium-177, and indium-111 and terbium-161. The copolymers of the present invention are also useful in diagnostic monitoring. For example, changes in biodistribution of the copolymer comprising a targeting moiety targeting to a certain cancer tissue type, the said copolymer further comprising a radionuclide useful in diagnosis, may indicate progress of a therapy targeting said cancer tissue. In particular, this approach may be useful in cancer monitoring, preferably in monitoring therapy of cancer that has metastasized. As disclosed herein, the copolymers of the present invention may be useful in cancer monitoring, herein defined as distribution of cancer tissue in the body of a subject, preferably of a patient.

In yet other particular embodiments, the active agents are a combination of a cytotoxic drug and a drug being capable of overcoming tumor cell resistance, for instance by inhibiting an anti-apoptotic factor such as Bcl-2 or targeting a cellular efflux pump (such as the MDR-1 transporter).

The afore-mentioned active agents are nonlimiting examples of agents and agent classes that are compatible with the copolymers of this disclosure, and someone skilled in art may use variants or derivatives of the disclosed agents and agent classes without exceeding the scope of this disclosure.

Depending on the structure of an active agent or other payload molecule, it may be coupled directly to the azide moiety of co-principal monomers of formula I or to an alpha-amino or an alpha-carboxylic group of a co-principle monomer of formula II or III contained in the copolymer, or it may be coupled to the copolymer via a linker structure. Such linker may function as a simple spacer between active agent and copolymer, function as a modifier of the copolymer pharmacokinetics or contain an element enabling or facilitating release of the active agent in a target cell. Linkers should be stable during storage and later in the blood stream to avoid unintended release of active agent. Release of active agent from the copolymer should take place only inside the target cells. Useful linkers (focusing on cancer therapy) should therefore be sensitive to intercellular factors such as caspases or cathepsins, glucuronidase (GUSB) (β-glucuronide-based linkers), acidic pH (found in tumor tissues or cell organelles [lysosomes]), or a reducing environment (responding to increased concentrations of intercellular glutathione). Another possibility will be the use of non-degradable linkers of the diamine type or thioether type which are not targets of a specific enzyme and are only degraded in the harsh conditions of the lysosome or peroxisomes. The latter linker type is preferred since it is associated with maximal serum stability and reduced unspecific toxicity.

Copolymers of the present disclosure are typically functionalized with a cell type- or tissue type-specific targeting moieties. While this functionalization step may be performed after active agents have been coupled to the copolymer, it will often be advantageous (in particular when highly cytotoxic agents or radioisotopes with short half lives are used) to first prepare a conjugate of a copolymer and a targeting moiety. Loading of the copolymer which active agents can then occur shortly prior to administration to a subject. Potential targeting moieties are, but are not limited to, monoclonal antibodies including immune checkpoint inhibitors, antibody fragments, nano-bodies (single-domain-antibodies), DARPins, peptide hormones, non-antibody proteins capable of binding to cell surface receptors, DNA/RNA-based aptamers as well as small molecules capable of binding to cell surface receptors (e.g., folic acid or biotin in the tumor context). In the context of a cancer therapy it is favorable if the above mentioned target moieties have a low to negligible expression level in healthy tissues and a high expression level/copy number on the cells surface of the cancer cells to avoid adverse effects. Potential targets are but not limited to CD19 (B-Lymphocyte Surface Antigen B4), CD20 (B-lymphocyte antigen), CD21 (Complement receptor type 2, CR2), CD22 (Cluster of differentiation-22), CD40 (Cluster of differentiation-40), CD52 (CAMPATH-1 antigen), CD152 (ETLA-4, cytotoxic T-lymphocyte-associated Protein 4), CD180 (RP105), CD274 (PD-L1, Programmed cell death 1 ligand 1), CD279 (PD-1, Programmed cell death protein 1), EGFR (Epidermal Growth Factor Receptor), FAP (Fibroblast activation protein), GD2 (Disialoganglioside), GITR (Glucocorticoid-induced TNFR family related gene), HER2 (human epidermal growth factor receptor 2, ERBB2, erb-b2 receptor tyrosine kinase), KIR2DL1 (Killer cell immunoglobulin-like receptor 2DL1), NKG2D (KLRK1) MSLN (Mesothelin), PDGF (Platelet Derived Growth Factor), PDGFR (Platelet Derived Growth Factor Receptor), VEGF (Vascular Endothelial Growth Factor), VEGFR (Vascular Endothelial Growth Factor Receptor), CAE (Carcinoembryonic antigen), CA9/CA IX (Carbonic anhydrase IX), α-folate receptor (Folate receptor 1), and PSMA (prostate-specific membrane antigene).

The covalent attachment of the targeting moiety to the copolymer should be carried out in a site-specific manner to obtain a homogeneous product as well as to preserve the targeting moiety's binding affinity. Suitable coupling strategies are enzyme-catalyzed reactions with peptides tags, e.g., sortase-mediated coupling, aldehyde tags, or transglutaminase tags, or the so-called "click" reaction between copolymer and targeting moiety. The latter process may be achieved through integration during synthesis of reactive, non-canonical (unnatural) amino acids into a proteinaceous targeting moiety, e.g., an antibody (such as by means of a codon expansion technique that uses a reprogrammed stop codon that is recognized by a tRNA for an unnatural amino acid).

Sortase refers to a group of prokaryotic enzymes that modify surface proteins by recognizing and cleaving a carboxyl-terminal sorting signal. For *Staphylococcus aureus*-derived enzymes the recognition signal consists of the motif LPXTG (Leu-Pro-any-Thr-Gly) and for *Staphylococcus pyogenes*-derived enzymes it is LPXTA (Leu-Pro-any-Thr-Ala). The signal sequence is preceded by a highly hydrophobic transmembrane sequence and a cluster of basic residues such as arginine. Cleavage occurs between the Thr and Gly/Ala residues of the signal sequence, with transient attachment of the Thr residue to the active site Cys residue of the sortase, followed by transpeptidation that attaches the protein covalently to a cell wall component (e.g., the peptido-glycan layer of gram-positive bacteria). Cozzi, R. et al. (2011) FASEB J 25(6): 1874-86. This enzymatic mechanism can be adapted to achieve fusion of peptides or proteins and has been used recently for the preparation of ADCs. European patent appl. no. 20130159 484 (EP 2 777 714); Beerli, R R et al. (2015) PloS One 10(7): e0131177. In the approach disclosed, a monoclonal antibody was genetically modified to contain sortase motifs at the C-termini of its heavy and light chains, and a cytotoxic drug was modified to contain an oligo-glycine stretch. The sortase-catalyzed reaction added the modified drug molecules to the C-termini of the antibody chains with high efficiency, resulting in a homogeneous ADC.

By modification of the head group of a copolymer of this disclosure with an oligo-glycine stretch, the copolymer itself becomes a target for sortase-catalyzed reactions. Since the copolymer can be loaded with a multitude of active agents, this approach results in ADCs in which many active agent molecules are linked to a small number of defined (innocuous) sites in an antibody (2-4 C-terminal sortase tags per antibody molecule). Consequently, the DAR is elevated, and with it the potency of the ADC. The oligo-glycine stretch of the copolymer can be introduced at the start of the polymerization using a recently developed RAFT agent containing 2-8 glycine residues. When this functionalized RAFT agent is used, only one sortase motif is present in each copolymer molecule.

Another enzymatic coupling method utilizes a transglutaminase-catalyzed reaction. Transglutaminases, also called protein-glutamine gamma-glutamyltransferases usually cross-link proteins by transferring the γ-carboxyamide group of the glutamine residue of one protein to the ε-amino group of the lysine residue of the same or another protein. Over the last two decades, these enzymes were used in diverse areas like the food industry as "meat-glue" (Martins I M et al. (2014), Appl. Microbiol. Biotechnol. 98: 6957-64?), tissue engineering (Ehrbar M. et al. (2007) Bio-macromolecules, 8(10):3000-7), modification of therapeutic proteins (Mero A. et al. (2011) J Control Release, 154(1):27-34) or gene delivery (Trentin D. et al. (2005) J Control Release, 102(1): 263-75).

In this context, microbial transglutaminases (MTgs) are the preferred class of enzymes as they are, in contrast to endogenous human transglutaminases, calcium- and nucleotide-independent enzymes. They consist of a single domain, compared to the four domains of human transglutaminases, and have about half the molecular weight of human transglutaminases. Moreover, MTgs operate at a larger range of pH values, buffers, and temperatures and have a much larger list of potential substrates. Kieliszek M et al. (2014) Rev Folia Microbiol. 59: 241-50; Martins I M. et al. (2014).

In analogy to the sortase-mediated coupling strategy, a transglutaminase motif is introduced to the head group of a copolymer of this disclosure by modification of a RAFT-agent, ensuring that only one transglutaminase motif is introduced per polymer chain. Suitable motifs are small peptides such as, but not limited to, FKGG (Ehrbar M. et al. (2007)) as potential lysine donor sequence, and LQSP or TQGA (Caporale A. et al. (2015) Biotechnol J. 10(1):154-61) as glutamine acceptor sequences [in this case an reactive lysine residue in the cancer cell specific targeting moiety is used]; or a monodisperse PEG spacer of 3-25 units' length containing a terminal amino group as potential glutamine acceptor sequences.

A variant of this strategy utilizes the transglutaminase for site-directed attachment of a click-reactive group (e.g. an azide or a tetrazine) to the targeting moiety, e.g. a monoclonal antibody, which antibody-linked reactive group is subsequently used for reaction with an "opposite" click-reactive group (alkyne or/strained alkene) at the polymeric head group of a copolymer of this disclosure. The mentioned reactive parts at the copolymer/antibody are meant to be interchangeable. This preferred strategy was used in the Examples presented herein (Examples 16, 23 and 34).

Other methods for linking a targeting moiety to a copolymer may be employed. Targeting antibodies or other polypeptides may be altered post-translationally, e.g., by converting a hydroxyl function in an amino acid side chain to a reactive aldehyde. In the case of polynucleotide-based targeting moieties, e.g., aptamers, coupling to a copolymer of this disclosure might be achieved by reaction with reactive functional groups (for instance amines, thiols, aldehydes) integrated into the aptamer during solid phase synthesis. Other site-directed coupling techniques that are well known in the art can be used to couple a copolymer to a targeting moiety.

Pharmaceutical Compositions

The pharmaceutical compositions of the present disclosure comprise an effective amount of an active moiety of the present disclosure formulated together with one or more pharmaceutically acceptable carriers or excipients.

The pharmaceutical compositions of this disclosure may be administered parenterally, by inhalation spray, topically in the eye, rectally, nasally, buccally, vaginally or via an implanted reservoir, preferably by administration by injection (or infusion). The pharmaceutical compositions of this disclosure may contain any conventional non-toxic pharmaceutically acceptable carrier, adjuvant or vehicle. In some cases, the pH of the formulation may be adjusted with pharmaceutically acceptable acids, bases or buffers to enhance the stability of the formulated active moiety or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. Solubilizing excipients include water-soluble organic solvents such as polyethylene glycol 300, polyethylene glycol 400, ethanol, propylene glycol, glycerin, N-methyl-2-pyrrolidone, dimethylacetamide and dimethylsulfoxide; non-ionic surfactants such as Cremophor EL, Cremophor RH40, Cremophor RH60, Solutol HS15, d-α-tocopherol polyethylene glycol 1000 succinate, polysorbate 20, polysorbate 80, sorbitan monooleate, poloxamer 407, Labrafil M-1944CS, Labrafil M-2125CS, Labrasol, Gellucire 44/14, Softigen 767, and mono- and di-fatty acid esters of PEG 300, 400 and 1750; water-insoluble lipids such as castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil, various cyclodextrins such as α-cyclodextrin, β-cyclodextrin, hydroxypropyl-β-cyclodextrin (e.g., Kleptose), and sulfobutylether-β-cyclodextrin (e.g., Captisol); and phospholipids such as lecithin, hydrogenated soy phosphatidylcholine, distearoylphosphatidylglycerol, L-α-dimyristoylphosphatidylcholine and L-α-dimyristoyl-phosphatidylglycerol. Strickley (2004) Pharm. Res. 21: 201-30.

The injectable formulations can be sterilized, for example, by filtration through a bacteria-retaining filter, or by incorporating sterilizing agents in a sterile solid composition (or sterilize the solid composition by irradiation) which subsequently can be dissolved or dispersed in sterile water or other sterile injectable medium prior to use.

In order to prolong the effect of an active agent, it is often desirable to slow the absorption of an active agent from subcutaneous or intramuscular injection. Delayed absorption of a parenterally administered active moiety is accomplished by dissolving or suspending the active moiety in an oil vehicle. Injectable depot forms are made by microencapsulating the active moiety in biodegradable polymers such as polylactide-polyglycolide. Depending upon the ratio of active moiety to polymer and the nature of the particular polymer employed, the rate of active agent release can be controlled. Examples of other biodegradable polymers include poly(orthoesters) and poly(anhydrides). Depot injectable formulations are also prepared by entrapping the active moiety in liposomes or microemulsions that are compatible with body tissues.

Compositions for rectal or vaginal administration are preferably suppositories which can be prepared by mixing an active moiety of this disclosure with a suitable non-irritating excipient or carrier such as cocoa butter, polyethylene glycol or a suppository wax which excipients/carriers are solid at ambient temperature but liquid at body temperature and therefore melt in the rectum or the vaginal cavity and release the active moiety (and, consequently, the active agent).

Ophthalmic formulations, ear drops, eye ointments, powders and solutions are also contemplated as being within the scope of this disclosure.

For pulmonary delivery, a pharmaceutical composition of the disclosure is formulated and administered to the patient in solid or liquid particulate form by direct administration e.g., inhalation into the respiratory system. Solid or liquid particulate forms of the active moiety prepared for practicing the present disclosure include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. Nos. 5,767,068, 5,508,269 and WO 98/43650). A discussion of pulmonary delivery of antibiotics is also found in U.S. Pat. No. 6,014,969.

The total daily dose of an active moiety of this disclosure administered to a human subject or patient in single dose or in divided doses preferably includes 0.01 to 50 mg/kg body weight of active agent or, more preferably, 0.1 to 30 mg/kg body weight of active agent. Single dose compositions may contain such amounts or submultiples thereof to make up the daily dose. In general, treatment regimens according to the present disclosure comprise administration to a human subject in need of such treatment from about 1 mg to about 5000 mg of active agent (comprised in an active moiety of this disclosure) per day in single dose or divided doses. Doses for mammalian animals can be estimated based on the latter human doses.

For the copolymers of the present invention comprising a radionuclide, in particular a radionuclide useful in therapy, the dose of radionuclide may also be described in the units of radioactivity, preferably in MBq/kg body weight. The total daily dose of the copolymer comprising a radionuclide of this disclosure administered to a human subject or patient in single dose or in divided doses preferably is between 3 and 300 MBq/kg body weight. As it is known to the skilled person, the further preferred dosing regimens depend on the used radionuclide. For the copolymers of the present invention comprising yttrium-90 the total daily dose administered to a human subject or patient in single dose or in divided doses preferably is between 5 and 35 MBq/kg body weight, even more preferably between 7 and 25 MBq/kg body weight, most preferably between 10 and 15 MBq/kg body weight. For the copolymers of the present invention comprising lutetium-177 the total daily dose administered to a human subject or patient in single dose or in divided doses preferably is between 5 and 100 MBq/kg body weight, even more preferably between 10 and 80 MBq/kg body weight, most preferably between 10 and 60 MBq/kg body weight. As understood herein, single dose compositions may contain such amounts or submultiples thereof to make up the daily dose. As understood herein, the skilled person will be able to determine the preferred dosage, depending on the radionuclide and on the desired application (for example treatment of a solid tumour, treatment of a heamatological tumour, lymphodepletion to enable an efficient CART-T therapy).

An active moiety of this disclosure can be administered, for example, by injection, intravenously, intraarterially, subdermally, intraperitoneally, intramuscularly, or subcutaneously; or buccally, nasally, transmucosally, topically in an ophthalmic preparation, or by inhalation, as a daily dose comprising about 0.01 to about 50 mg/kg of body weight of active agent. Alternatively, dosages (based on the latter daily dose of active agent) may be administered every 4 to 120 hours, or according to the requirements of the particular active moiety. The methods herein contemplate administration of an effective amount of an active moiety (in a pharmaceutical composition) to achieve the desired or stated effect. Typically, the pharmaceutical compositions of this disclosure will be administered from about 1 to about 6 times per day or alternatively, as a continuous infusion. Such administration can be used as a chronic or acute therapy. The amount of active moiety that may be combined with pharmaceutically acceptable excipients or carriers to produce a single dosage form will vary depending upon the host treated and the particular mode of administration. A typical composition will contain from about 5% to about 95% active moiety (w/w). Alternatively, such preparations may contain from about 20% to about 80% active active moiety. Specific dosage and treatment regimens for any particular patient will depend upon a variety of factors, including the activity of the specific active moiety employed, the age, body weight, general health status, sex, diet, time of administration, rate of excretion, drug combination, the severity and course of the disease, condition or symptoms, the patient's disposition to the disease, condition or symptoms, and the judgment of the treating physician.

All references cited in this application, including publications, patents and patent applications, shall be considered as having been incorporated in their entirety.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as reference to an element or elements is intended to provide support for a similar aspect or embodiment of the disclosure that "consists of'," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present disclosure, thus generally described, will be understood more readily by reference to the following examples, which are provided by way of illustration and are not intended to be limiting of the present invention.

EXAMPLES

Note: In the examples relating to synthesis of side chain-linked amino acids names are first given in IUPAC nomenclature. Thereafter, abbreviated names are used. Table 1 shows the correspondence.

TABLE 1

IUPAC names and abbreviations

| IUPAC | Abbreviation |
|---|---|
| Co-principal monomers | |
| (S)-6-acrylamido-2-aminohexanoic acid | Acryloyl-L-lysine, AK |
| (2S)-3-(acryloyloxy)-2-aminopropanoic acid | Acryloyl-L-serine, AS |
| (2S)-3-(acryloyloxy)-2-aminobutanoic acid | Acryloyl-L-threonine, AT |
| (S)-3-(4-(acryloyloxy)phenyl)-2-aminopropanoic acid | Acryloyl-L-tyrosine, AY |
| (S)-2-(4-acrylamidophenyl)-2-aminoacetic acid | Acryloyl-L-amino-phenylalanine, AHOX |
| (2S)-4-(acryloyloxy)pyrrolidine-2-carboxylic acid | Acryloyl-L-cysteine, AC |
| (R)-3-(acryloylthio)-2-aminopropanoic acid | Acryloyl-L-oxi-proline, AHOP |

TABLE 1-continued

| IUPAC names and abbreviations | |
|---|---|
| IUPAC | Abbreviation |
| (R)-2-((5-acrylamido-1-carboxypentyl)amino)-2-oxoethanediazonium | AK-Azide |
| 17-(4-acrylamidobutyl)-1-azido-15-oxo-3,6,9,12-tetraoxa-16-azaoctadecan-18-oic acid | AK-$PEG_{(4)}$-Azide |
| (S)-3-(4-acrylamidophenyl)-2-(2-azidoacetamido)propanoic acid | AHOX-Azide |
| 3-(2,5-dioxo-2,5-dihydro-1H-pyrrol-1 -yl)-N-(2-(2-(2-(2-(4-(6-methyl-1,2,4,5-tetrazin-3-yl)phenoxy)ethoxy)ethoxy)ethoxy)ethyl)propanamide | Tetrazine-$PEG_{(4)}$-MC |
| Polymeric substances | |
| α-ethyl-trithiocarbonate-ω-tert-butyl (14-methyl-2,5,8,13-tetraoxo-3,6,9,12-tetraazapentadecyl)carbamate poly(N,N-dimethylacrylamide) | BOC-G3-DMA-RAFT pre-polymer |
| α-thiol-ω-2-methylpropanoic acid poly(N,N-dimethylacrylamide, (S)-6-acrylamido-2-aminohexanoic acid) | HS-($DMA_{(55)}$-$AK_{(4)}$) |
| α-thiol-ω-2-methylpropanoic acid poly(N,N-dimethylacrylamide, (S)-6-acrylamido-2-(6-azidohexanamido)hexanoic acid) | HS-($DMA_{(55)}$-AK-(6-Azidohexanoyl)$_{(4)}$) |
| α-thiol-ω-2-methylpropanoic acid poly(N,N-dimethylacrylamide, 2-hydroxypropyl)acrylamide) | HS-($HPA_{(55)}$-$AK_{(4)}$) |
| Intermediates | |
| 2-(((ethylthio)carbonothioyl)thio)-2-methylpropanoic acid | Ethyl-RAFT |
| 2,5-dioxopyrrolidin-1-yl 2-(((ethylthio)carbonothioyl)thio)-2-methylpropanoate | RAFT-NHS |
| tert-butyl (2-(2-(((ethylthio)carbonothioyl)thio)-2-methylpropanamido)ethyl)carbamate | RAFT-EDA-BOC |
| 2-(2-(((ethylthio)carbonothioyl)thio)-2-methylpropanamido)ethanaminium 2,2,2-trifluoroacetate | RAFT-EDA-OTf |
| tert-butyl (6,6-dimethyl-7,12,15,18-tetraoxo-4-thioxo-3,5-dithia-8,11,14,17-tetraazanonadecan-19-yl)carbamate | BOC-$G_{(3)}$-RAFT |
| 6,6-dimethyl-7-oxo-4-thioxo-11,14,17,20,23-pentaoxa-3,5-dithia-8-azapentacosan-25-aminium chloride | $NH_2$-$PEG_{(5)}$ RAFT |
| 2,2',2''-(10-(2,6-dioxotetrahydro-2H-pyran-3-yl)-1,4,7,10-tetraazacyclododecane-1,4,7-triyl)triacetic acid | DOTA-Anhydride |
| 4,7,10-Tetraazacyclododecane-1,4,7-tris(acetic acid)-10-[3-oxo-3-(5-azadibenzocyclootyne)acetamide] | DBCO-DOTA |
| 2,2',2''-(10-(4-((2-((((1R,8S,9s)-bicyclo[6.1.0]non-4-yn-9-ylmethoxy)carbonyl)amino)ethyl)amino)-1-carboxy-4-oxobutyl)-1,4,7,10-tetraazacyclododecane-1,4,7-triyl)triacetic acid | BCN-DOTA |
| N-[3-(11,12-Didehydrodibenz[b,f]azocin-5(6H)-yl)-3-oxopropyl]-2,5-dihydro-2,5-dioxo-1H-pyrrole-1-propanamide | MC-DBCO |
| (E)-cyclooct-4-en-1-yl (2-(2-(2-(2-aminoethoxy)ethoxy)ethoxy)ethyl)carbamate | TCO-$PEG_{(3)}$-amine |
| 4-((3-azidopropyl)carbamoyl)-2-(6-hydroxy-3-oxo-3H-xanthen-9-yl)benzoic acid | FAM-Azide |
| 4-(2-(2-((((2,5-dioxopyrrolidin-1-yl)oxy)carbonyl)amino)-3-methylbutanamido)-5-ureidopentanamido)benzyl (1-((1-((1-(2-(3-((1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate | MMAE-NHS |
| Chemicals | |
| N-Hydroxysuccinimide | NHS |
| N-Ethyl-N'-(3-dimethylaminopropyl)carbodiimide hydrochloride | EDC•HCl |
| 2,2'-Azobis[2-(2-imidazolin-2-yl)propane]dihydrochloride | VA044 |
| 4-aminobenzyl alcohol | PABOH |
| N-Ethoxycarbonyl-2-ethoxy-1,2-dihydroquinoline | EEDQ |
| Diisopropylethylamine | DIEA |
| N-methyl-2-pyrrolidone | NMP |
| Dichloromethane | DCM |
| Tetrahydrofuran | THF |
| Ethyl acetate | EtOAc |
| Methanol | MeOH |
| 2,5-dioxopyrrolidin-1-yl 2-(4-(6-methyl-1,2,4,5-tetrazin-3-yl)phenyl)acetate | Tetrazine-NHS |

It is noted that the copolymers in this disclosure are polymerized by controlled radical polymerization techniques like RAFT polymerization and have a low poly dispersion index (PDI) that is usually in the range of 1.1-1.4. The numbers given for the exemplified polymeric drug carriers in this disclosure indicate the average monomer composition of the copolymer chain. The copolymers in this disclosure are random copolymers unless otherwise stated.

Example 1: Synthesis of 6-acrylamido-2-(2-azidoacetamido)hexanoic acid

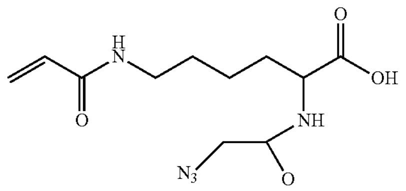 [SMILES: C=CC(=O)NCCCCC(NC(O)CN=[N+]=[N-])C(=O)O]

A solution of 2,5-dioxopyrrolidin-1-yl 2-azidoacetate (4.0 eq.) in tetrahydrofuran was added dropwise to a cooled solution of 6-acrylamido-2-aminohexanoic acid (1.0 eq.) and sodium hydrogen carbonate (2.0 eq.) in $H_2O$. The solution was stirred at 0° C. for 1 hour and then at room temperature overnight. THF was removed from the solution under reduced pressure. The solution was then acidified with 6M HCl to a pH of 1 and extracted with ethyl acetate (3×). The combined organic phases were dried over $Na2SO_4$ and concentrated under reduced pressure. The resulting oily film was dissolved in a small amount of EtOAc and added dropwise to Heptane. The fine white precipitated powder was filtered off and dried under vacuum resulting in the desired product (95% yield). The structure of the obtained compound was verified by NMR spectroscopy.

Example 2: Synthesis of 6-acrylamido-2-(6-azidohexanamido)hexanoic acid

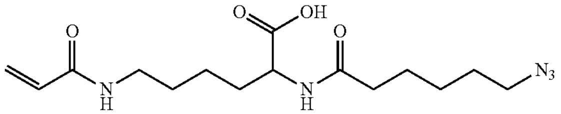 [SMILES: C=CC(=O)NCCCCC(NC(=O)CCCCCN=[N+]=[N-])C(=O)O]

6-acrylamido-2-(6-azidohexanamido)hexanoic acid (85% Yield) was prepared as described in Example 1 except that 2,5-dioxopyrrolidin-1-yl 6-azidohexanoate, (Sigma-Aldrich, Switzerland, 4.0 eq.) was used. The structure of the obtained compound was verified by NMR spectroscopy.

Example 3: Synthesis of AK-$PEG_M$-Azide

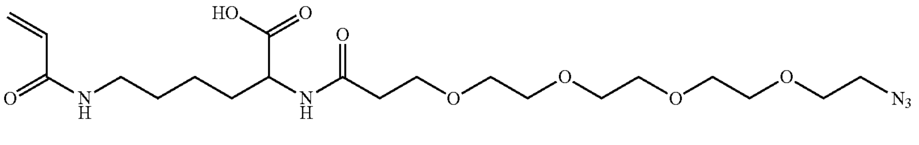 [SMILES: C=CC(=O)NCCCCC(NC(=O)CCOCCOCCOCCOCCN=[N+]=[N-])C(=O)O]

AK-$PEG_4$-Azide (82% Yield) was prepared as described in Example 1 except that azido-$PEG_{(4)}$-NHS (Click Chemistry Tools, Scottsdale, USA, 4.0 eq.) was used. The structure of the obtained compound was verified by NMR spectroscopy.

Example 4: Synthesis of (S)-6-acrylamido-2-aminohexanoic acid Monomers Via Copper Complex L-lysine (14.62 g; 100 mmol) was dissolved in 150 mL deionized water and heated to about 80° C. Copper carbonate (16.6 g; 75 mmol) was added in portions over a period of 30 minutes. The reaction was stirred for an additional 30 minutes. The hot, deep-blue suspension was filtered through silica gel. The filter was washed with a small amount of water. On the subsequent day, the lysine copper complex-containing the combined filtrate was cooled in an ice bath, and 100 mL tetrahydrofuran (THF) were added. A solution of acryloyl chloride in methyl-tert-butylether (TBME) (8.9 mL, 110 mmol) was added dropwise during a period of one hour. The pH was initially maintained between 8 and 10 by parallel, dropwise addition of 10% sodium hydroxide solution. After half the acryloyl chloride solution had been added, the product began to precipitate. When most of the acryloyl chloride had been added, the addition of sodium hydroxide was slowed down to allow the pH to drop to about 6 and the temperature of the reaction mixture to reach room temperature. The blue suspension was stirred during an additional 2 hours and was then filtered. The solid material retained on the filter was washed with water and acetone and then dried. A yield of 6.5 g of acryloyl-L-lysine copper complex was obtained.

Acryloyl-L-lysine copper complex (29.5 g) was suspended in 300 mL deionized water and cooled in an ice bath. $H_2S$ gas was bubbled into the suspension until the copper sulfide precipitation was complete. Three grams of active charcoal were added to the suspension. The suspension was heated briefly to 100° C. After cooling to room temperature, 500 mL acetone were added to the suspension which was then filtered on silica gel. The clear filtrate was put in a rotary evaporator. After evaporation of the solvent, the solid product was recrystallized from 200 mL of 50% aqueous acetone. A yield of 17.76 g (70%) of white powder was obtained. The structure of the compound was verified by NMR and LC-MS spectroscopy.

Example 5: Synthesis (2S)-3-(acryloyloxy)-2-aminopropanoic acid

A solution of L-serine (5 g, 47.6 mmol) in water (50 mL) was heated to 80° C., and solid copper carbonate (5.79 g, 26.2 mmol) was added. The solution was stirred for 10 min. Undissolved residue was subsequently collected by filtration and washed with water (30 mL). The combined filtrate was cooled in an ice bath, and KOH (27.1 mL, 47.6 mmol) was added slowly. To this solution a mixture of acryloyl chloride (4.52 mL, 59.5 mmol) in acetone (30 mL) was added dropwise. The reaction mixture was then incubated at 4° C. overnight under stirring. The formed solid was isolated and washed with water (50 mL)/methanol (50 mL)/ethyl-tert-butylether (50 mL) (MTBE) and finally dried under reduced pressure to give O-acryloyl-L-serine-$Cu^{2+}$ complex (3.8 g, 10.01 mmol; 42.1% yield). The copper in the complex was subsequently removed by a similar procedure as that described in example 1. A yield of 1.43 g (45%) of acryloyl-L-serine as white powder was obtained. The identity of the compound was verified by NMR and LC-MS spectroscopy.

Example 6: Synthesis (2S)-3-(acryloyloxy)-2-aminobutanoic acid

A reaction vessel with 6 mL trifluoroacetic acid (TFA) was cooled in an ice bath. Subsequently, solid L-threonine (2.00 g, 16.79 mmol) was added, and the mixture was stirred for 5 min. Trifluromethanesulfonic acid (0.18 mL, 2.0 mmol) and, subsequently, acryloyl chloride (2.5 mL, 32.9 mmol) were added, and the reaction mixture was incubated for 2 h at room temperature. After completion of the reaction, the product was precipitated with methyl-tert-butylether (MTBE). After isolation of the solid, the product was washed with MTBE and acetone. O-Acryloyl-L-threonine hydrochloride was finally dried under reduced pressure to give a white powder (yield 32%). The structure of the compound was verified by NMR and LC-MS spectroscopy.

Example 7: Synthesis of (S)-3-(4-(acryloyloxy)phenyl)-2-aminopropanoic acid

The synthesis of O-acryloyl-L-tyrosine-$Cu^{2+}$-complex was performed according to the procedure described in Example 1. Copper was removed from the complex by the following procedure: 73.15 g (140 mmol) of O-acryloyl-L-tyrosine-$Cu^{2+}$-complex was dissolved in 220 mL 2 N HCl in a grinding dish. The mixture was homogenized using Polytron® PT 3000 equipment. Subsequently, the mixture was filtered and the residue washed twice with 50 mL 2 N HCl. The solid compound was then dried over NaOH at 40° C. under reduced pressure to give O-acryloyl-L-tyrosine hydrochloride (46.96 g, 63% yield).

Example 8: Synthesis of (S)-2-(4-acrylamidophenyl)-2-aminoacetic acid

Boc-4-amino-L-phenylalanine (2.50 g, 8.9 mmol, Anaspec, Fremont, Calif.) was dissolved in 25 mL chloroform. Triethylamine (2.47 mL, 17.8 mmol) was given to this solution, and the mixture was cooled to −15° C. Subsequently, acryloyl chloride (0.79 mL, 9.8 mmol) in chloroform was added dropwise to the mixture under stirring. After the acryloyl chloride addition was completed, the reaction mixture was stirred for three additional hours. The reaction mixture was thereafter passed through a glass filter, the protected (S)-2-(4-acrylamidophenyl)-2-aminoacetic acid was purified by column chromatography, and the residual solvents were evaporated. The obtained (S)-2-(4-acrylamidophenyl)-2-((tert-butoxycarbonyl)amino)acetic acid (500 mg, 1.5 mmol) was dissolved in 5 mL dichloromethane (DCM). Trifluoracetic acid (TFA) (800 µL, 10.38 mmol) was added, and the solution was stirred for 1 h at room temperature. Afterwards, the solvent was removed under reduced pressure, 5 mL DCM were added, and the solvent was again removed under reduced pressure. This procedure was repeated several times. Finally, the product was dissolved in 3 mL DCM and precipitated with methyl-tert-butylether (MTBE). The solid was collected on a glass filter and dried in vacuo to obtain pure acryloyl-4-amino-L-phenylalanine at a yield of 15%. The structure of the compound was verified by NMR.

Example 9: Synthesis of (2S)-4-(acryloyloxy)pyrrolidine-2-carboxylic acid and (R)-3-(acryloylthio)-2-aminopropanoic acid The synthesis of these compounds was performed as described in Example 4. For (2S)-4-(acryloyloxy)pyrrolidine-2-carboxylic acid and (R)-3-(acryloylthio)-2-aminopropanoic acid, the starting materials were, respectively, 4-hydroxy-L-proline and L-cysteine.

Example 10 Synthesis AHOX-Azide Based on Example 8

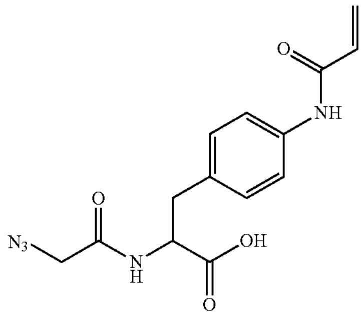 [SMILES: C=CC(=O)Nc1ccc(CC(NC(=O)CN=[N+]=[N-])C(=O)O)cc1]

A solution of acryloyl-4-amino-L-phenylalanine (4.0 eq.) in tetrahydrofuran is added dropwise to a cooled solution of 6-acrylamido-2-aminohexanoic acid (1.0 eq.) and sodium hydrogen carbonate (2.0 eq.) in $H_2O$. The solution is stirred at 0° C. for 1 hour and then at room temperature overnight. THF is removed from the solution under reduced pressure. The solution is then acidified with 6M HCl to a pH of 1 and extracted with ethyl acetate (3×). The combined organic phases are dried over $Na_2SO_4$ and concentrated under reduced pressure. The resulting oily film is dissolved in a small amount of EtOAc and added dropwise to Heptane. The fine white precipitate is filtered off and dried under vacuum resulting in the desired product.

Example 11: Synthesis of BOC-$G_{(3)}$-RAFT Agent

Step 1: Synthesis of the RAFT-NHS Intermediate:

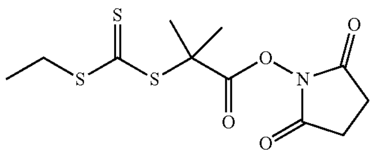 [SMILES: CCSC(=S)SC(C)(C)C(=O)ON1C(=O)CCC1=O]

To a solution of Ethyl-RAFT (22.85 g, 102 mmol, 1.0 eq.), synthesized as described in Tucker et al. (ACS Macro Letters (2017) 6(4): 452-457), and 1-hydroxypyrrolidine-2,5-dione (12.89 g, 112 mmol, 1.1 eq.) in $CH_2Cl_2$ was added EDC-HCl (21.48 g, 112 mmol, 1.1 eq.) at 0° C. The reaction mixture was allowed to stir at room temperature for 16 h. The reaction mixture was then partially evaporated (to about half of the total volume) under a flow of $N_2$ and diluted with AcOEt and double-distilled water ($ddH_2O$). The biphasic solution was transferred in a separating funnel and, after extraction, the organic phase was successively washed with $ddH_2O$, an aqueous saturated solution of $NaHCO_3$ (3×), $ddH_2O$ (2×) and brine. The organic phase was dried ($Na_2SO_4$), and all volatiles were removed under reduced pressure. The residue was triturated with n-hexane and the resulting yellow suspension was filtered. The cake was washed with n-hexane. The yellow solid was dried under reduced pressure, and the resulting intermediate (RAFT-NHS) was used without further purification (31.8 g, 99.0 mmol, 97%). All analytical data were in agreement with literature values. Yang et al. (2012) Macromolecular rapid communications 33(22): 1921-6.

Step 2: Synthesis of the RAFT-EDA-BOC Intermediate:

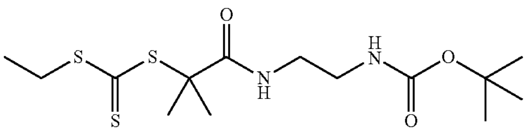 [SMILES: CCSC(=S)SC(C)(C)C(=O)NCCNC(=O)OC(C)(C)C]

To a solution of RAFT-NHS starting material (1.22 g, 3.61 mmol 1.0 eq.) in $CH_2Cl_2$ was added dropwise and at −10° C. a solution of t-butyl-(2-aminoethyl) carbamate (0.81 g, 5.0 mmol, 1.4 eq.) and $Et_3N$ (1.0 mL, 7.2 mmol, 2.0 eq.) in $CH_2Cl_2$. The reaction mixture was stirred for 12 h at room temperature. The organic mixture was successively washed with an aqueous saturated solution of $NH_4Cl$ (2×), an aqueous saturated solution of $NaHCO_3$ (2×), and brine. The organic phase was dried ($Na_2SO_4$), and all volatiles were removed under reduced pressure. The residue was recrystallized from a mixture of n-heptane and $Et_2O$. The yellow crystals were filtrated, washed with n-heptane and dried under reduced pressure to give the next intermediate (RAFT-EDA-BOC, 1.26 g, 3.44 mmol, 95%). The structure of the obtained compound was verified by MS and NMR spectroscopy.

Step 3: Synthesis of the RAFT-EDA-OTf Intermediate:

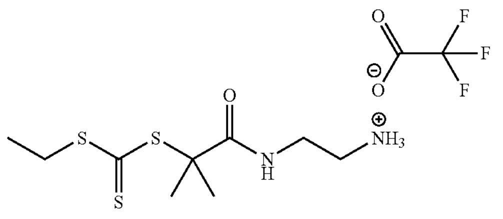

A cold solution of RAFT-EDA-BOC (1.25 g, 3.41 mmol, 1.0 eq.) in TFA was stirred for 60 min. The reaction mixture was then diluted with MeOH and $CH_2Cl_2$ (½), and the volatiles were partially (% of the total volume) removed under a flow of $N_2$. The resulting RAFT-EDA-OTf was isolated as a yellow oil (2.00 g, 3.29 mmol, 96%) and was used in the next step without further purification. The structure of the obtained compound was verified by MS and NMR spectroscopy.

Step 4: Synthesis of a BOC-$G_{(3)}$-RAFT Intermediate:

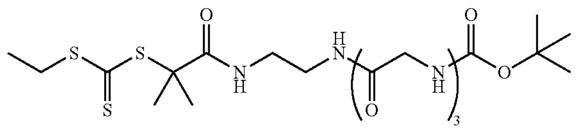

A solution of BOC-$G_{(3)}$ (Bachem AG, Bubendorf, Switzerland) (697 mg, 2.41 mmol, 1.0 eq.), 1-hydroxybenzotriazole hydrate (HOBt hydrate) (92.0 mg, 600 μmol, 0.25 eq.) and EDC-HCl (485 mg, 2.53 mmol, 1.05 eq.) in $CH_2Cl_2$ was stirred for 30 min at 0° C. under inert atmosphere ($N_2$). To this solution was successively and dropwise added a solution of RAFT-EDA-OTf (917 mg, 2.41 mmol, 1.0 eq.) in $CH_2Cl_2$ and DIPEA (2.13 mL, 12.5 mmol, 5.2 eq.). The reaction mixture was stirred for 1 h at 0° C. and then overnight at room temperature. The reaction mixture was diluted with $CH_2Cl_2$, and the organic mixture was successively washed with a saturated solution of $NH_4Cl$ (3×), with a saturated solution of $NaHCO_3$, $ddH_2O$ and brine. The organic phase was collected, dried ($Na_2SO_4$), and the volatiles were partially removed (% of the total volume) under reduced pressure. To the resulting solution was added EtOAc. The resulting cloudy solution was then stored in the refrigerator overnight to obtain a yellow suspension, which was filtered, and the cake was washed with cold EtOAc. The yellow solid was dried under reduced pressure to obtain BOC-$G_{(3)}$-RAFT agent (396 mg, 736 μmol, 31%). The structure of the obtained compound was verified by MS and NMR spectroscopy.

The here presented example is thought to be a general procedure for the synthesis of a RAFT agent which is functionalized with an ology-glycine spacer. Longer or shorter spacers can be synthesized by the exchange of the oligo-glycine building block.

Example 12: Synthesis of RAFT-$PEG_{(5)}$-$NH_3Cl$

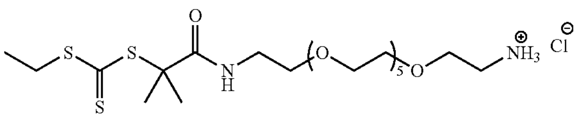

To a solution of RAFT-NHS starting material (1.4 mmol) in $CH_2Cl_2$ was added a solution of BOC-$PEG_{(5)}$-$CH_2CH_2$—$NH_2$ (1.4 mmol) and $Et_3N$ (1.5 mmol) in $CH_2Cl_2$ dropwise at 0° C. The reaction mixture was then stirred at rt overnight. The mixture was evaporated and purified over a RP-18 column chromatography (1:1 ACN:$H_2O$) to give RAFT-$PEG_{(5)}$-BOC (1.2 mmol, 88%). The structural assignment has been determined from mass and NMR spectroscopic data.

A cold solution of RAFT-$PEG_{(5)}$-BOC (0.25 mmol) in 3M HCl in EtOAc was stirred for 120 min. The reaction mixture was then evaporated and purified over a RP-18 column chromatography (1:1 ACN:$H_2O$+0.1% Acetic acid). The resulting RAFT-$PEG_{(5)}$-$NH_3Cl$ was isolated as a yellow oil (0.21 mmol, 84%). The structural assignment has been determined from mass and NMR spectroscopic data.

Example 13: Synthesis of a $NH_2$-$PEG_{(5)}$-($DMA_{(45)}$ AK-$Azid_{(4)}$) Copolymer Using $NH_2$-$PEG_{(5)}$

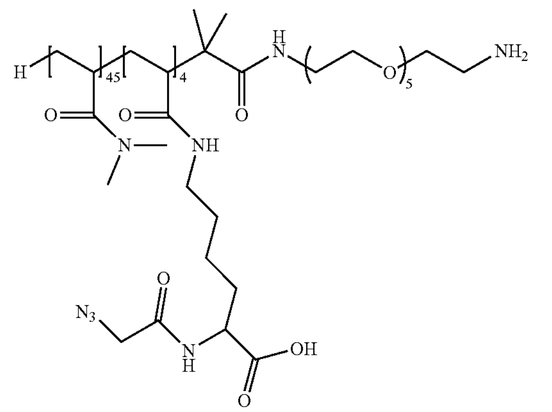

To a solution of DMA (100 μL, 970 μmol, 30 eq.) and AK-Azide (69.7 mg, 259 μmol, 8 eq.) in 0.1 M $NaHCO_3$ were successively added $NH_2$-$PEG_{(5)}$ RAFT (16.92 mg, 32.2 μmol, 1.0 eq.) and VA044 (3.14 mg, 9.7 μmol, 0.3 eq.). The reaction mixture was stirred for 4 h at 60° C. The reaction mixture was diluted with $ddH_2O$ and dioxane. To this solution was successively added phosphinic acid (50 w %, 27 μL, 158 μmol, 5 eq.), TEA (22 μL, 158 μmol, 5 eq.) and AIBN (1.6 mg, 9.5 μmol, 0.3 eq.). The reaction mixture was stirred for 8 h at 75° C. The resulting mixture was then dialyzed (MWCO 3.5 kDa) against $ddH_2O$ and the retentate was freeze-dried to obtain $NH_2$-$PEG_{(5)}$-($DMA_{(45)}$-AK-$Azide_{(4)}$) as a white powder (130 mg, 120 μmol, 85% over two steps). The structure of the obtained compound was investigated by NMR spectroscopy and GPC using the following protocol: A stock solution of 3.33 mg/mL copolymer was prepared in elution buffer (deionized water containing 0.05% (w/v) $NaN_3$) and filtered through a 0.45 μm syringe filter. Subsequently, 0.4 mL of stock solution was injected in the port of the GPC device (1260 Infinity LC-System, Agilent, Santa Clara, Calif.). Chromatography was performed at a constant flow rate of 0.5 mL/min in elution buffer. Copolymer samples were separated on a Suprema three-column system (pre-column, 1000 Å, 30 Å; 5 μm particle size; PSS, Mainz, Germany) which was placed in an external column oven at 55° C. Copolymers were analyzed by RI (refractive index) and UV detectors. A calibration curve (10 points) was established using a pullulan standard obtained from PSS (Mainz, Germany), including the following 10 polymers (Mw, Mn and PDI are given): (1) Mw: 342/Mn: 342, PDI 1.0; (2) Mw:1320/Mn: 1080, PDI 1.23; (3) Mw: 6200/Mn: 5900, PDI 1.05; (4) Mw: 10000/Mn: 9200, PDI 1.09; (5) Mw: 21700/Mn: 20000, PDI 1.09; (6) Mw: 48800/Mn 45500, PDI 1.07; (7) Mw: 113000/Mn: 100000, PDI 1.13; (8) Mw: 210000/Mn 189000, PDI 1.11; (9) Mw: 366000/Mn 318000, PDI 1.15; (10) Mw: 805000/Mn: 636000, PDI: 1.27. Molecular weights of characterized copolymers were estimated with reference to this standard. To this end, weight average molecular weight of the polymer (Mw), number average molecular weight of the polymer (Mn) and its PDI are determined based on GPC measurements by the software PSS WinGPC Unichrom V:8.1 Build 2827 (PSS; https://www.pss-polymer.com/).

Example 14: Synthesis of $NH_2$-$PEG_{(5)}$-($DMA_{(45)}$ AK-$DOTA_{(4)}$)

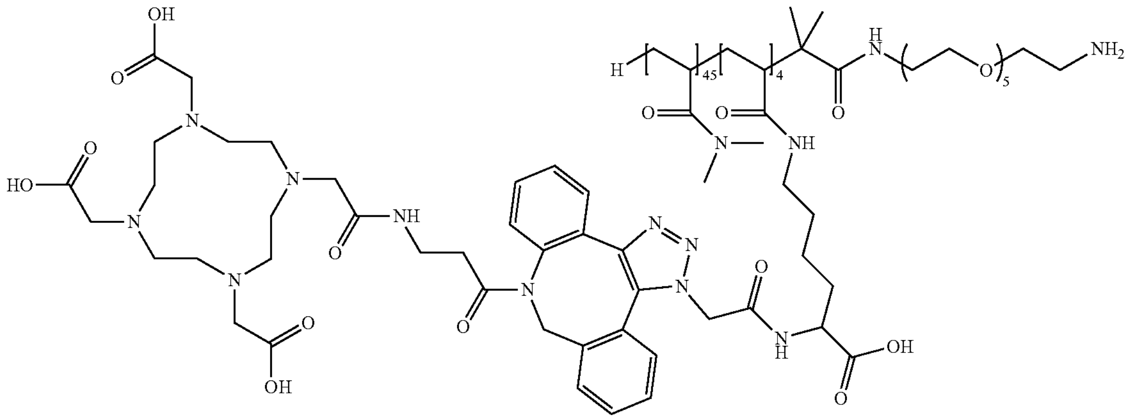

A solution of $NH_2$-$PEG_{(5)}$-($DMA_{(45)}$AK-$Azid_{(4)}$) (20 mg, 3.45 μmol) and chelating agent BCN-DOTA (Chematech Dijon, France) (24 mg, 34 μmol) in 0.1 M $NaHCO_3$ was stirred for 24 h at 35° C. The resulting mixture was then dialyzed (MWCO 3.5 kDa) against dd$H_2O$ and the retentate was freeze-dried to obtain $NH_2$-$PEG_{(5)}$-($DMA_{(45)}$AK-$DOTA_{(4)}$). The structure of the obtained compound was investigated by NMR spectroscopy.

Example 15: Synthesis of DBCO-NH-$PEG_{(5)}$-($DMA_{(45)}$AK-$DOTA_{(4)}$)

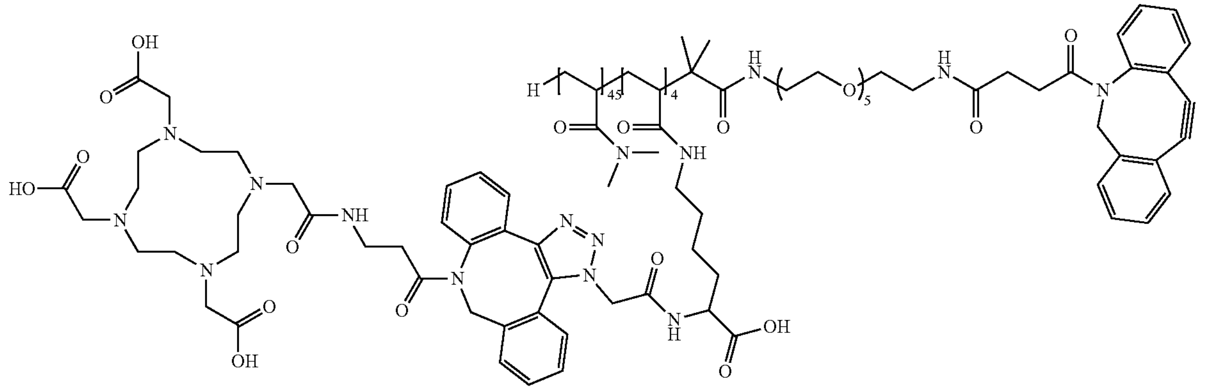

A solution of $NH_2$-$PEG_{(5)}$-($DMA_{(45)}$AK-$DOTA_{(4)}$) (10 mg, 1.15 μmol) synthesized according to example 14, DBCO-NHS (3.96 mg, 9.2 μmol) and TEA (1.275 μL, 9.2 μmol) in DMF was stirred for 7 h at 25° C. The resulting mixture was then dialyzed (MWCO 3.5 kDa) against dd$H_2$ O and the retentate was freeze-dried to obtain DBCO-NH-$PEG_{(5)}$-($DMA_{(45)}$AK-$DOTA_{(4)}$). The structure of the obtained compound was investigated by NMR spectroscopy. To verify the activity of this DBCO—group, the obtained polymer was dissolved in DMF and an excess of FAM-azide was added at RT and the mixture was stirred for 4 h. The resulting compound was verified with GPC using the protocol presented in example 13

Example 16: Synthesis of a Radiolabeled Trastuzumab-[NH-$PEG_{(4)}$-Triazole-$PEG_{(5)}$-($DMA_{(45)}$AK-$DOTA_{(4)}$]$_2$ Conjugate for Diagnostic and Therapeutic Targeting of Her2 Receptor Over-expressing Cancer Cells

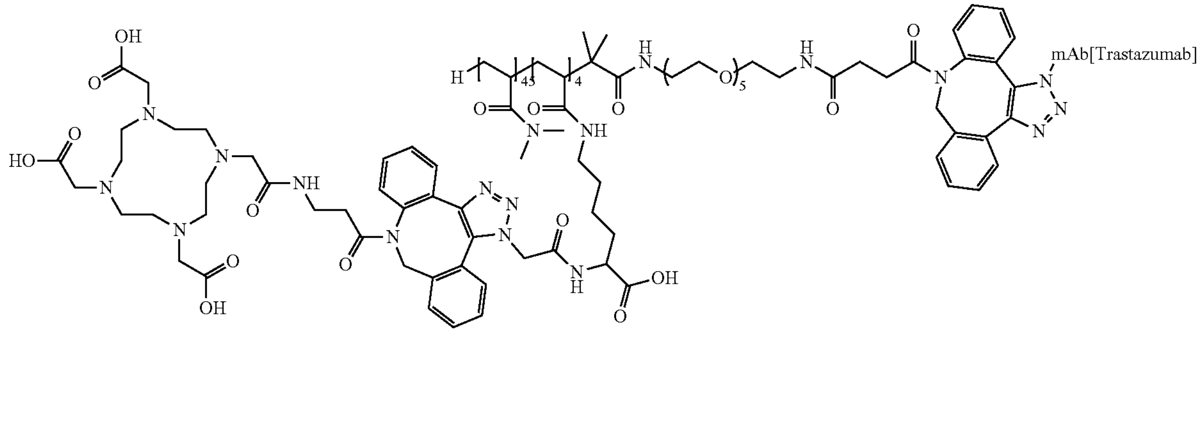

In tumor diagnosis, the detection limit for the primary tumor or its metastases is crucial for the survival rate of patients since late stage tumors are often associated with a poor prognosis. Using radiolabeled tumor tissue-specific antibodies for detection as well as subsequent therapy of cancer cells is a potentially promising method for radio medicine. However, approaches of this type have been hampered by low signal to noise ratios due to the facts that only a few radioisotopes could be attached to a targeting moiety/antibody and that the radioisotopes of interest have short half-lives (usually shorter than the half-life of the antibody). Therefore, an increased cargo of radioisotopes would be highly desirable. In this example, a radiolabeled antibody-copolymer conjugate for improved tumor cell detection and therapy is described.

DBCO-functionalized copolymer DBCO-NH-PEG$_{(5)}$-(DMA$_{(45)}$-AK-DOTA$_{(4)}$, synthesized by procedures presented in example 15, was conjugated to a cancer cell-specific antibody of the IgG type (Trastuzumab for targeting Her2+ cancer cells) that had been functionalized with an azide group at the glutamine in position 295 (Q 295) by a procedure described by Dennler et al. (Bioconjugate Chem. (2014) 25: 569-578).

Briefly, the antibody was deglycosylated by PNGaseF (Merck KGaA, Darmstadt, Germany). A reaction mixture containing 1 unit of enzyme per 10 µg Trastuzumab (Carbosynth Ltd, Berkshir, UK) in PBS (pH 7.4) was incubated overnight at 37° C. in order to activate Q295. Subsequently, deglycosylated Trastuzumab (6.6 µm) in PBS (pH 8) was incubated with $NH_2$-PEG$_{(4)}$-Azide (Click Chemistry Tools, Scottsdale, USA) (80 molar eq.) and microbial transglutaminase (MTGase) (6 U/mL, Zedira, Darmstadt, Germany) for 16 h at 37° C. After incubation MTGase activity was blocked by the addition of MTGase reactionstopper (Zedira, Darmstadt, Germany). To remove excess $NH_2$-PEG$_4$-Azide, MTGase and residual PNGaseF, the reaction mixture was buffer-exchanged (three times) into $NH_4$OAc (0.5 m, pH 5.5) by using an Amicon® Ultra 4 mL column (100 kDa MWCO, Merck KGaA, Darmstadt, Germany).

The actual click reaction was subsequently performed by incubation of Trastuzumab-(NH-PEG$_{(4)}$-Azide)$_2$ with a 3-fold molar excess of DBCO-functionalized polymer overnight at 37° C., yielding Trastuzumab-[NH-PEG$_{(4)}$-Triazole-PEG$_{(5)}$-(DMA$_{(45)}$AK-DOTA$_{(4)}$)]$_2$ The success of the reaction was investigated by SDS PAGE using non-modified Trastuzumab as control. Reaction mixtures (20 µl) were stopped by the addition of 5 µl 4×SDS-PAGE loading buffer +10% w/v β-mercaptoethanol (Biorad, Germany) and incubated (60 min, 37° C., constant shaking at 600 rpm). The samples were subsequently electrophoresed on 4-20% SDS-PAGE gels (Mini-PROTEAN® TGX™ Precast Gels Biorad, Germany) at 150 V for 40 min, and the gels were subjected hereafter to Coomassie blue staining. These experiments revealed a quantitative functionalization of the antibody's heavy chain with the copolymer.

Excess polymer and residual non-functionalized Trastuzumab can be removed by size exclusion chromatography (SEC) and the fraction containing the desired product can be combined.

Radiolabeling of the antibody-copolymer conjugate with 111-InCl$_3$ (4 MBq per µg Trastuzumab-[NH-PEG$_{(4)}$-Triazole-PEG$_{(5)}$-(DMA$_{(45)}$AK-DOTA$_{(4)}$)]$_2$ is performed for 1 h at 37° C., after which the indium-111-labeled antibody-polymer-conjugate is purified by SEC on a Superdex 75 10/300 GL column (GE Healthcare, Chicago, USA) run at a 0.5 mL/min flow rate. Major peak fractions are pooled. The resulting Trastuzumab-[NH-PEG$_{(4)}$-Triazole-PEG$_{(5)}$-(DMA$_{(45)}$AK-DOTA-IN-111$_{(4)}$)]$_2$ may be used to detect Her2+ cancer cells by positron-emission-tomography (PET), e.g., in breast, colon or lung cancer patients, with a higher sensitivity than could be attained by conventional antibody-radioisotope complexes. The increased sensitivity is due to the increase In-111 cargo carried by the antibody-carrier complex compared to conventionally radiolabeled antibody.

The same procedure may be used to prepare a therapeutic antibody-copolymer conjugate loaded with a suitable therapeutic radioisotope such as Lutecium-177 [substituting the 111-InCl$_3$ used in the above-described procedure with 177-LuCl$_3$].

Example 17: Synthesis of a Tetrazine-NH-PEG$_{(5)}$-(DMA$_{(45)}$AK-Azide$_{(4)}$) Copolymer Using $NH_2$-PEG$_{(5)}$-(DMA$_{(45)}$AK-Azide$_{(4)}$)

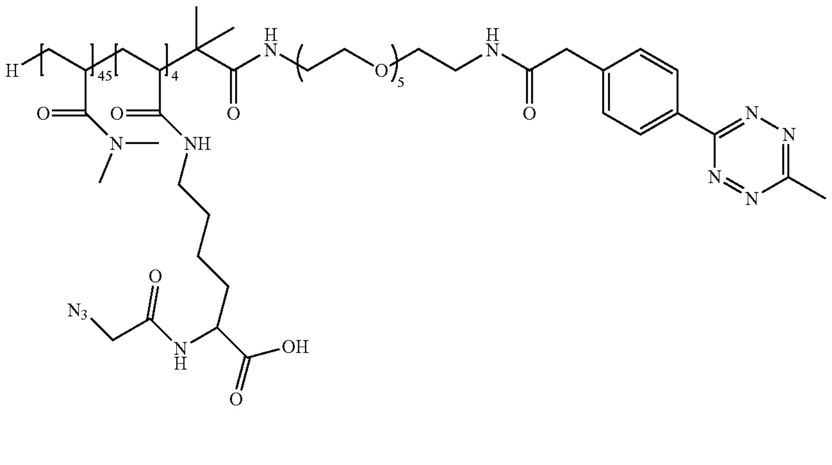

To a solution of $NH_2$-PEG$_{(5)}$-(DMA$_{(45)}$AK-Azide$_{(4)}$) (3.57 μmol) synthesized according to example 13, Tetrazine-NHS (18 μmol) and TEA (3.57 μmol) in DMF was stirred for 8 h at 25° C. The resulting mixture was then dialyzed (MWCO 3.5 kDa) against dd$H_2O$ and the retentate was freeze-dried to obtain Tetrazine-NH-PEG$_{(5)}$-(DMA$_{(45)}$AK-Azide$_{(4)}$). The structure of the obtained compound was investigated by NMR spectroscopy.

Example 18: Synthesis of a BOC-G$_{(3)}$-RAFT Prepolymer

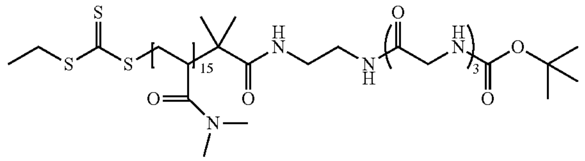

To a solution of DMA (1000 μL, 9704 μmol, 15 eq.) in Dioxane were successively added BOC-$G_3$-RAFT (348 mg, 647 μmol, 1.0 eq.) and AIBN (31.9 mg, 194 μmol, 0.3 eq.). The reaction mixture was stirred for 4 h at 70° C. The reaction mixture was diluted with n-hexane and the prepolymer was obtained as yellow powder after n-hexane washing. The structure of the obtained compound was investigated by NMR spectroscopy and GPC using the following protocol: A stock solution of 3.33 mg/mL copolymer was prepared in elution buffer (deionized water containing 0.05% (w/v) $NaN_3$) and filtered through a 0.45 μm syringe filter. Subsequently, 0.4 mL of stock solution was injected in the port of the GPC device (1260 Infinity LC-System, Agilent, Santa Clara, Calif.). Chromatography was performed at a constant flow rate of 0.5 mL/min in elution buffer. Copolymer samples were separated on a Suprema three-column system (pre-column, 1000 Å, 30 Å; 5 μm particle size; PSS, Mainz, Germany) which was placed in an external column oven at 55° C. Copolymers were analyzed by RI (refractive index) and UV detectors. A calibration curve (10 points) was established using a pullulan standard. Molecular weights of characterized copolymers were estimated with reference to this standard.

Example 19: Synthesis of Boc-G$_{(3)}$-(DMA$_{(45)}$AK$_{(4)}$AK-Azide$_{(4)}$)

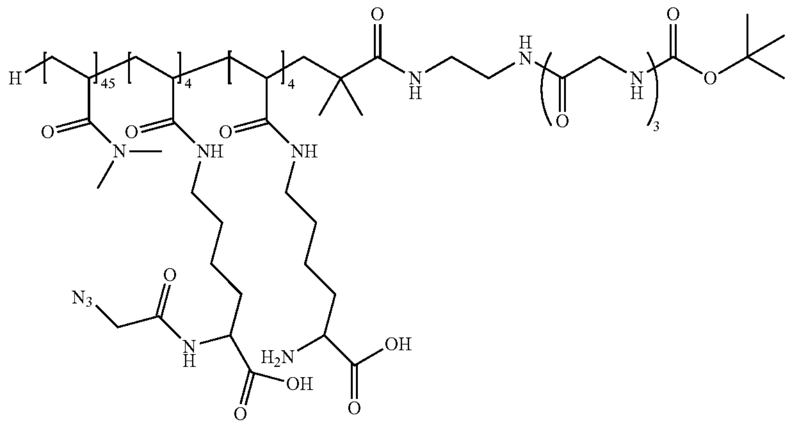

To a solution of DMA (116 μL, 1120 μmol, 30 eq.), AK (30 mg, 150 μmol, 4 eq.), AK-Azide (42 mg, 150 μmol, 4 eq.) in dd$H_2O$ were successively added the BOC-G$_{(3)}$-RAFT prepolymer (79 mg, 37 μmol, 1.0 eq.) from example 16 and VA044 (3.6 mg, 11.2 μmol, 0.3 eq.). The reaction mixture was stirred for 4 h at 60° C. The resulting mixture was then dialyzed (MWCO 3.5 kDa) against dd$H_2O$ and the retentate was freeze-dried to obtain BOC-G$_{(3)}$-(DMA$_{(45)}$AK$_{(4)}$AK-Azide$_{(4)}$) The structure of the obtained compound was investigated by NMR spectroscopy and GPC using the protocol presented in example 13.

Example 20: Synthesis of Boc-$G_{(3)}$-($DMA_{(45)}AK_{(4)}$ AK-$DOTA_{(4)}$)

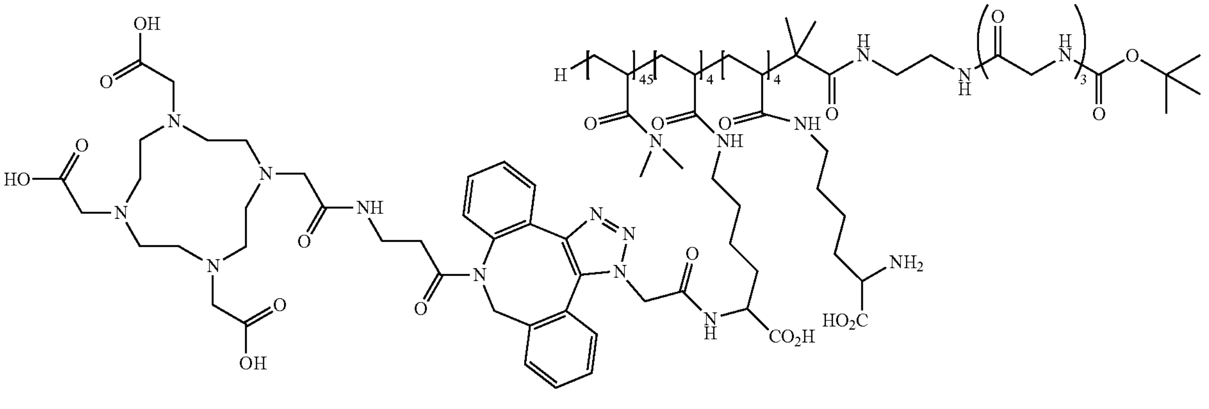

To a solution of Boc-$G_3$-($DMA_{(45)}AK_{(4)}$AK-$Azide_{(4)}$) (260 mg, 37 μmol, 1 eq) in DMF was added DBCO-DOTA (199 mg, 300 μmol, 8 eq.) in DMF. The reaction mixture was stirred for 4 h at room temperature and diluted with dioxane. To this solution was successively added phosphinic acid (50 w %, 32 μL, 185 μmol, 5 eq.), TEA (26 μL, 158 μmol, 5 eq.) and AIBN (1.9 mg 11.1 μmol, 0.3 eq.). The reaction mixture was stirred for 8 h at 75° C. The resulting mixture was then dialyzed (MWCO 3.5 kDa) against dd$H_2O$ and the retentate was freeze-dried to obtain Boc-$G_3$-($DMA_{(45)}AK_{(4)}$AK-$DOTA_{(4)}$) as a white powder (198 mg, 22 μmol, 56% over three steps). The structure of the obtained compound was investigated by NMR spectroscopy and GPC using the protocol presented in example 13.

Example 21: Synthesis of Boc-$G_3$-($DMA_{(45)}$AK-$MMAE_{(4)}$AK-$DOTA_{(4)}$)

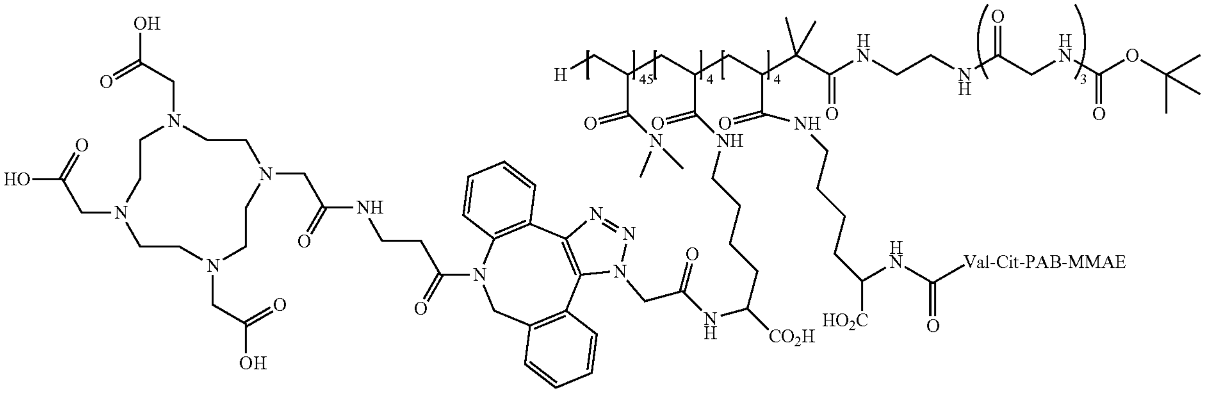

To a solution of Boc-$G_3$- ($DMA_{(45)}AK_{(4)}$AK-$DOTA_{(4)}$) (14 mg, 1.5 μmol, 1 eq.) in dd$H_2O$ a solution of MMAE-NHS (5 eq.) (cytotoxic agent) in DMSO is added and stirred for 24 h at 35° C. The resulting mixture is then dialyzed (MWCO 3.5 kDa) against dd$H_2O$ and the retentate is freeze-dried to obtain Boc-$G_{(3)}$-($DMA_{(45)}$AK.$MMAE_{(4)}$-AK-$DOTA_{(4)}$). The structure of the obtained compound is investigated by NMR spectroscopy.

Example 22: Synthesis of DBCO-$G_3$-($DMA_{(45)}$AK-$MMAE_{(4)}$AK-$DOTA_{(4)}$)

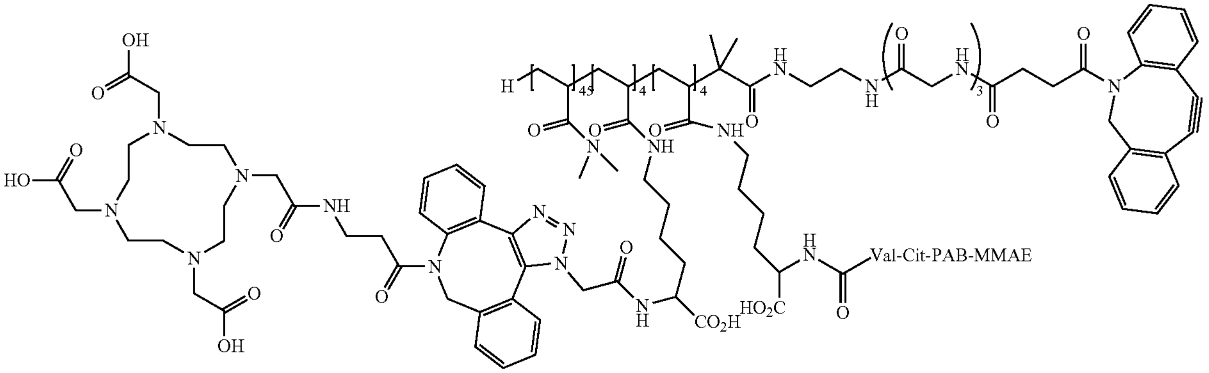

Boc-$G_{(3)}$-($DMA_{(45)}$AK-$MMAE_{(4)}$AK-$DOTA_{(4)}$) (28 mg, 2 μmol) is dissolved in a solution of TFA in DCM (1:1). After 4 h the organic solvent is removed under reduced pressure to obtain $NH_3Cl$-$G_3$-($DMA_{(45)}$AK-$MMAE_{(4)}$AK-$DOTA_{(4)}$). To a solution of $NH_3Cl$-$G_{(3)}$-($DMA_{(45)}$AK-$MMAE_{(4)}$AK-$DOTA_{(4)}$) (14, 1 μmol, 1 eq.) in DMF is successively added DBCO-NHS (3.4 mg, 8 μmol, 8.0 eq.) and TEA (1.1 μL, 8 μmol, 8.0 eq.). The reaction mixture is stirred for 4 h at 25°. The resulting mixture is diluted with $ddH_2O$ and then dialyzed (MWCO 3.5 kDa) against $ddH_2O$ and the retentate is freeze-dried to obtain DBCO-NH-$G_{(3)}$-($DMA_{(45)}$AK-$MMAE_{(4)}$AK-$DOTA_{(4)}$. The structure of the obtained compound is investigated by NMR spectroscopy. To verify the activity of this DBCO—group, the obtained polymer is dissolved in DMF and FAM-Azide was added. The resulting compound was verified with GPC using the protocol presented in example 13.

Example 23: Synthesis of a Radiolabeled Trastuzumab-[NH-$PEG_{(4)}$-Triazole-PEG-NH-$G_{(3)}$-($DMA_{(45)}$AK-$MMAE_{(4)}$AK-$DOTA_{(4)}$]$_2$ Conjugate for Diagnostic and Therapeutic Targeting Her2 Receptor Overexpressing Cancer Cells

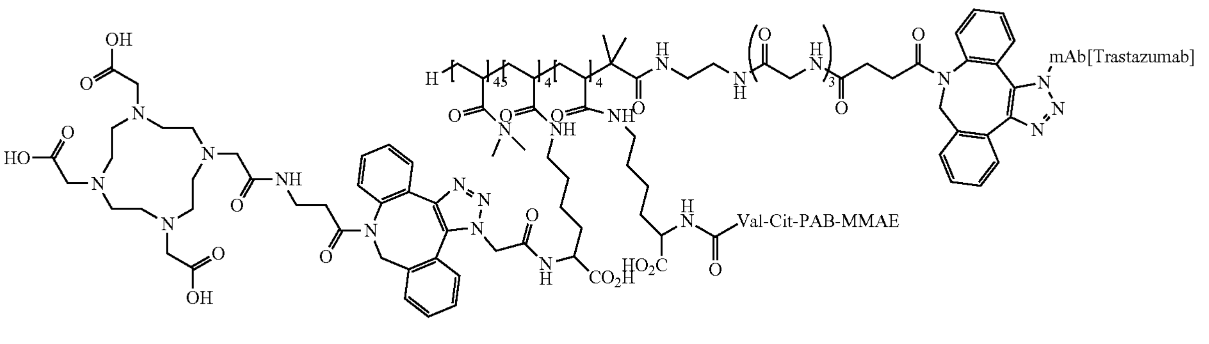

Most tumor therapies are monitored qualitatively by the reduction of tumor size (CT, MRT scans) and usually detailed characterization of the distribution of the cytotoxic agent is not performed. In some cases, it would be useful to get information on the actual tissue distribution with non-invasive methods. This could be achieved by binding to the same drug carrier a cytotoxin for the therapeutic approach and a diagnostic radioisotope for the monitoring. Thanks to this approach the fate of the antibody-polymer conjugated can be visualized and give useful information on potential side effects e.g. non intended metabolism in the liver or aggregation in other tissues. This approach would be advantageous especially for phase I clinical studies where dose finding and side effects are characterized.

DBCO-functionalized copolymer (DBCO-NH-$G_{(3)}$-($DMA_{(45)}$AK-$MMAE_{(4)}$AK-$DOTA_{(4)}$)), synthesized by procedures presented in example 22, is conjugated to a cancer cell-specific antibody of the IgG type (Trastuzumab for targeting Her2+ cancer cells) that is functionalized with an azide-group at the glutamine in position 295 (Q 295) by a procedure described by Dennler et al. (Bioconjugate Chem. (2014) 25: 569-578).

Briefly, the antibody is deglycosylated by PNGaseF (Merck KGaA, Darmstadt, Germany). A reaction mixture containing 1 unit of enzyme per 10 μg Trastuzumab (Carbosynth Ltd, Berkshir, UK) in PBS (pH 7.4) is incubated overnight at 37° C. in order to activate Q295. Subsequently, deglycosylated Trastuzumab (6.6 μm) in PBS (pH 8) is incubated with $NH_2$-$PEG_4$-Azide (Click Chemistry Tools, Scottsdale, USA) (80 molar eq.) and microbial transglutaminase (MTGase) (6 U/mL, Zedira, Darmstadt, Germany) for 16 h at 37° C. After incubation MTGase activity is blocked by the addition of MTGase reactionstopper (Zedira, Darmstadt, Germany). To remove excess $NH_2$-$PEG_4$-Azide, MTGase and residual PNGaseF, the reaction mixture is buffer-exchanged (three times) into $NH_4OAc$ (0.5 m, pH 5.5) by using an Amicon® Ultra 4 mL column (100 kDa MWCO, Merck KGaA, Darmstadt, Germany).

The actual click reaction is subsequently performed by incubation of Trastuzumab-(NH-$PEG_4$-Azide)$_2$ with a 3-fold molar excess of DBCO-functionalized polymer overnight at 37° C., yielding Trastuzumab-[DBCO-NH-$G_{(3)}$-($DMA_{(45)}$AK-$MMAE_{(4)}$AK-$DOTA_{(4)}$$]_2$. The success of the reaction is investigated by SDS PAGE using non-modified Trastuzumab as control. Reaction mixtures (20 µl) are stopped by the addition of 5 µl 4×SDS-PAGE loading buffer +10% w/v β-mercaptoethanol (Biorad, Germany) and incubated (60 min, 37° C., constant shaking at 600 rpm). The samples are subsequently electrophoresed on 4-20% SDS-PAGE gels (Mini-PROTEAN® TGX™ Precast Gels Biorad, Germany) at 150 V for 40 min, and the gels are subjected hereafter to Coomassie blue staining.

Excess polymer and residual non-functionalized Trastuzumab can be removed by size exclusion chromatography (SEC) and pooling of the fractions containing fully functionalized antibody.

Radiolabeling of the antibody-copolymer conjugate with 111-$InCl_3$ (4 MBq per µg Trastuzumab-[DBCO-NH-$G_{(3)}$-($DMA_{(45)}$AK-$MMAE_{(4)}$AK-$DOTA_{(4)}$$]_2$ is performed for 1 h at 37° C., after which the indium-111-labeled antibody-polymer-conjugate is purified by SEC on a Superdex 75 10/300 GL column (GE Healthcare, Chicago, USA) run at a 0.5 mL/min flow rate. Major peak fractions are pooled. The resulting Trastuzumab-[DBCO-NH-$G_{(3)}$-($DMA_{(45)}$AK-$MMAE_{(4)}$AK-Azide-(DOTA-In-111$)_4]_2$ may be used to detect Her2+ cancer cells by positron-emission-tomography (PET), e.g., in breast, colon or lung cancer patients, with a higher sensitivity than could be attained by conventional antibody-radioisotope complexes. The increased sensitivity is due to the increase In-111 cargo carried by the antibody-carrier complex compared to conventionally radiolabeled antibody.

Example 24: Tetrazine-$G_{(3)}$-($DMA_{(45)}$AK-$DOTA_{(4)}$AK-$Azide_{(4)}$)

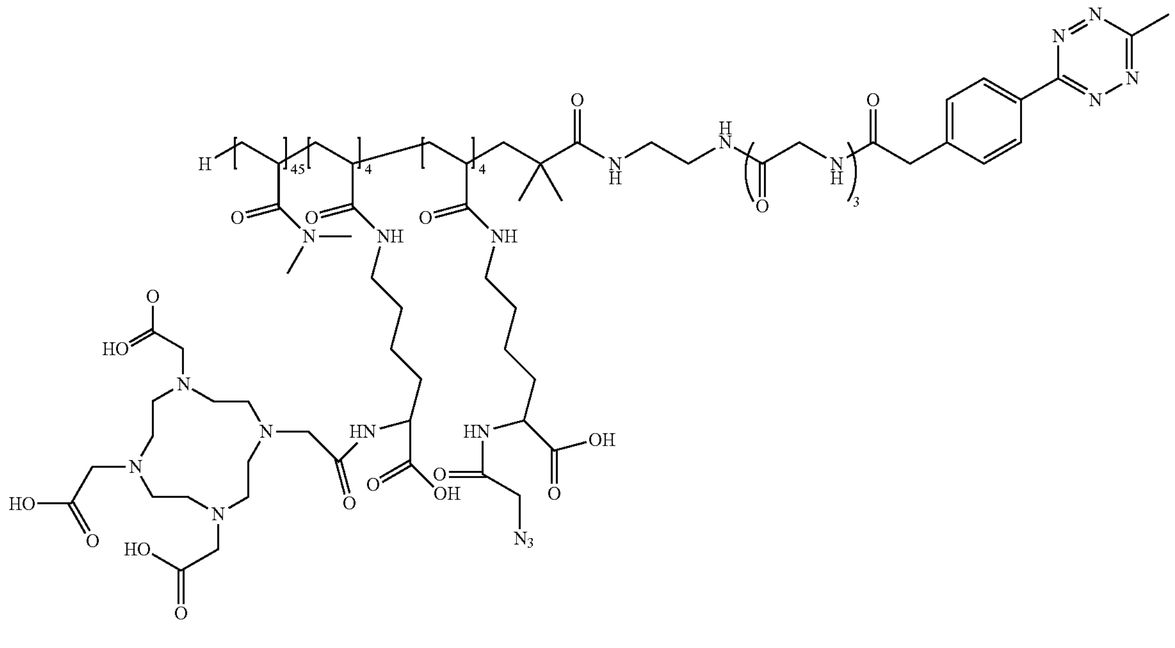

To a solution of Boc-$G_{(3)}$-($DMA_{(45)}$$AK_{(4)}$AK-$Azide_{(4)}$) (14 mg, 1.5 µmol, 1 eq.) in $ddH_2O$ a solution of DOTA-NHS (6 µmol, 4 eq.) in DMSO is added and stirred for 24 h at 35° C. The resulting mixture is then dialyzed (MWCO 3.5 kDa) against $ddH_2O$ and the retentate was freeze-dried to obtain Boc-$G_{(3)}$-($DMA_{(45)}$AK-$DOTA_{(4)}$AK-$Azide_{(4)}$). Subsequently Boc-$G_{(3)}$-($DMA_{(45)}$AK-$DOTA_{(4)}$AK-$Azide_{(4)}$) (2

µmol) is dissolved in a solution of TFA in DCM (1:1). After 4 h the organic solvent is removed under reduced pressure to obtain $NH_2$-$G_{(3)}$-($DMA_{(45)}$AK-$DOTA_{(4)}$AK-$Azide_{(4)}$). To a solution of $NH_2$-$G_{(3)}$-($DMA_{(45)}$AK-$DOTA_{(4)}$AK-$Azide_{(4)}$) (14, 1 µmol) in DMF is successively added Tetrazine-NHS (5 µmol) and TEA (2 µmol). The reaction mixture is stirred for 8 h at 25° C. The resulting mixture is diluted with $ddH_2O$ and then dialyzed (MWCO 3.5 kDa) against $ddH_2O$ and the retentate is freeze-dried to obtain Tetrazine-NH-$G_{(3)}$-($DMA_{(45)}$AK-$DOTA_{(4)}$AK-$Azide_{(4)}$). The structure of the obtained compound is investigated by NMR spectroscopy.

Example 25: Synthesis of HS-($DMA_{(45)}$AK-$Azide_{(4)}$)

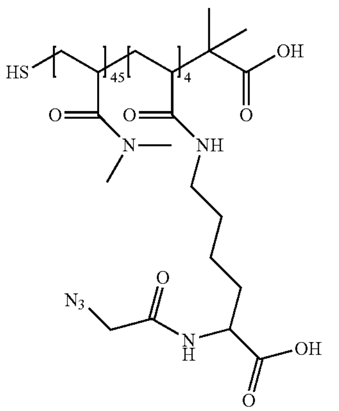

To a solution of DMA (116 µL, 1120 µmol, 45 eq.), AK-Azide (42 mg, 150 µmol, 4 eq.) in $ddH_2O$ were successively added Ethyl-RAFT (see example 11) (5.6 mg, 24.9 µmol, 1.0 eq.) and VA044 (3.6 mg, 11.2 µmol, 0.3 eq.). The reaction mixture was stirred for 4 h at 60° C. The reaction mixture was stirred for 4 h at room temperature. Cyclohexylamine (493 µL, 4977 µmol, 200 eq.) was added to the reaction mixture and stirred for 3 h at 30° C. The resulting mixture was then dialyzed (MWCO 3.5 kDa) against $ddH_2O$ and the retentate was freeze-dried to obtain HS-($DMA_{(45)}$ AK-$Azide_{(4)}$) as a white powder (120 mg, 20 μmol, 81% over three steps). The structure of the obtained compound was investigated by NMR spectroscopy and GPC using the protocol of example 13.

Example 26: Synthesis of HS-($DMA_{(45)}$ AK-$DOTA_{(4)}$)

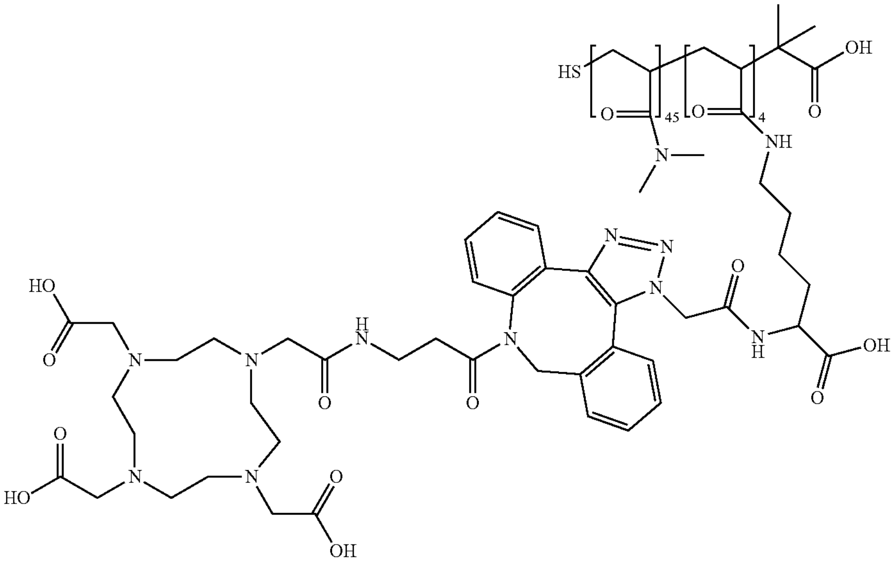

To a solution of HS-($DMA_{(45}$AK-$Azide_{(4)}$) (20 mg, 3.5 μmol, 1 eq.) in $ddH_2O$ a solution of DBCO-DOTA (19.0 mg, 24 μmol, 8 eq.) in DMSO was added and stirred for 24 h at 35° C. The resulting mixture was then dialyzed (MWCO 3.5 kDa) against $ddH_2O$ and the retentate was freeze-dried to obtain HS-($DMA_{(45)}$ AK-$DOTA_{(4)}$). The structure of the obtained compound was investigated by NMR spectroscopy.

Example 27 Synthesis of DBCO-($DMA_{(45)}$ AK-$DOTA_{(4)}$)

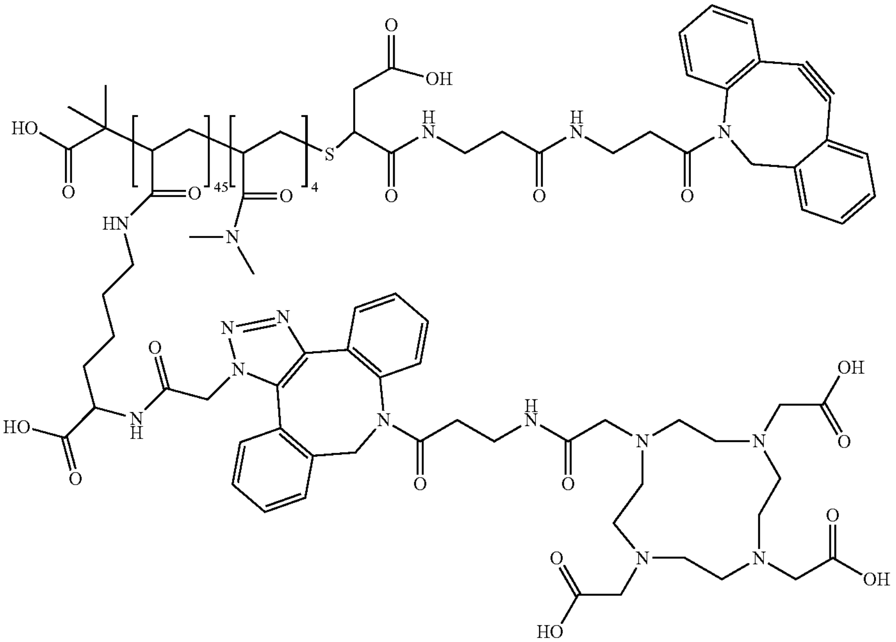

To a solution of HS-($DMA_{(45)}$AK-$DOTA_{(4)}$) (28 mg, 3 μmol) in DMF was added MC-DBCO (11.61 mg 14.4 μmol, 8.0 eq.) After 4 h the reaction mixture was diluted with $ddH_2O$ and then dialyzed (MWCO 3.5 kDa) against 0.1 M $NH_4HCO_3$ and the retentate was freeze-dried to obtain DBCO-($DMA_{(45)}$ AK-$DOTA_{(4)}$. The structure of the obtained compound was investigated by NMR spectroscopy. To verify the activity of this DBCO—group, the obtained polymer was dissolved in DMF and FAM-Azide was added. The resulting compound was verified with GPC using the following protocol: A stock solution of 3.33 mg/mL copolymer was prepared in elution buffer (deionized water containing 0.05% (w/v) $NaN_3$) and filtered through a 0.45 μm syringe filter. Subsequently, 0.4 mL of stock solution was injected in the port of the GPC device (1260 Infinity LC-System, Agilent, Santa Clara, Calif.). Chromatography was performed at a constant flow rate of 0.5 mL/min in elution buffer. Copolymer samples were separated on a Suprema three-column system (pre-column, 1000 Å, 30 Å; 5 μm particle size; PSS, Mainz, Germany) which was placed in an external column oven at 55° C. Copolymers were analyzed by RI (refractive index) and UV detectors. A calibration curve (10 points) was established using a pullulan standard. Molecular weights of characterized copolymers were estimated with reference to this standard. In this test the signal of 495 nm (FAM) and the RI signal of the copolymer showed a match at the overlay indicating that the copolymer was functionalized with an active DBCO head group.

Example 28: Synthesis of HS-($DMA_{(45)}$$AK_4$AK-$Azide_{(4)}$)

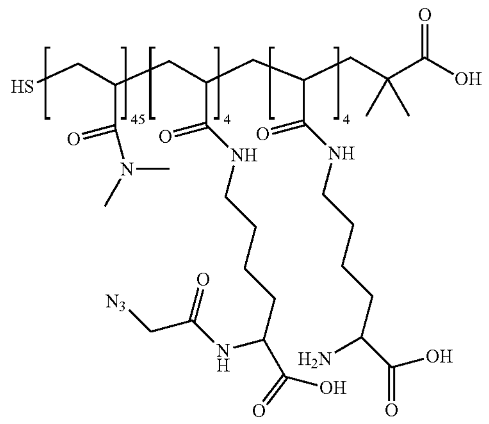

To a solution of DMA (116 μL, 1120 μmol, 45 eq.), AK (30 mg, 150 μmol, 4 eq.), AK-Azide (42 mg, 150 μmol, 4 eq.) in $ddH_2O$ were successively added Ethyl-RAFT (see example 11) (5.6 mg, 24.9 μmol, 1.0 eq.) and VA044 (3.6 mg, 11.2 μmol, 0.3 eq.). The reaction mixture was stirred for 4 h at 60° C. The reaction mixture was stirred for 4 h at room temperature. Cyclohexylamine (493 μL, 4977 μmol, 200 eq.) was added to the reaction mixture and stirred for 3 h at 30° C. The resulting mixture was then dialyzed (MWCO 3.5 kDa) against $ddH_2O$ and the retentate was freeze-dried to obtain HS-($DMA_{(45)}$$AK_{(4)}$AK-$Azide_{(4)}$) as a white powder (150 mg, 23 μmol, 88% over three steps). The structure of the obtained compound was verified by NMR spectroscopy and GPC using the protocol of example 13.

Example 29: Synthesis of HS-($DMA_{(45)}AK_{(4)}$AK-$DOTA_{(4)}$)

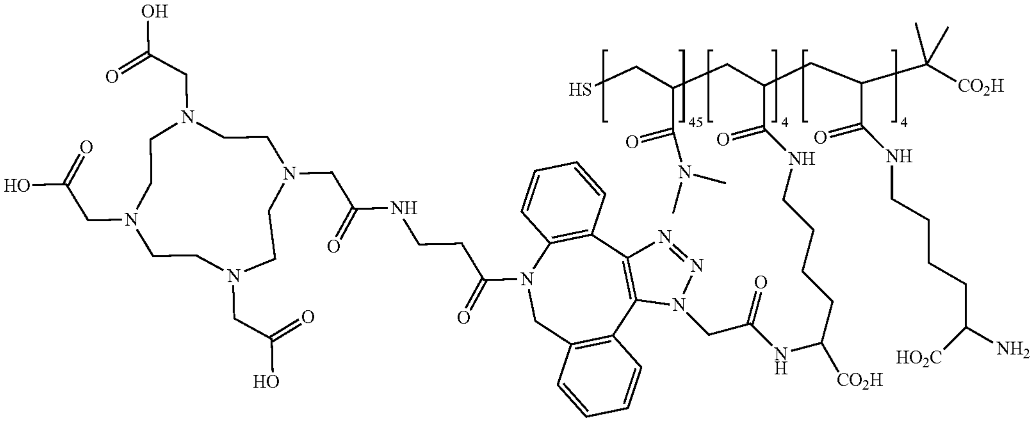

To a solution of HS-($DMA_{(45)}AK_{(4)}$AK-$Azide_{(4)}$) (20 mg, 3 μmol, 1 eq.) in $ddH_2O$ a solution of DBCO-DOTA (16.3 mg, 24 μmol, 8 eq.) in DMSO was added and stirred for 24 h at 35° C. The resulting mixture was then dialyzed (MWCO 3.5 kDa) against $ddH_2O$ and the retentate was freeze-dried to obtain HS-($DMA_{(45)}AK_{(4)}$AK-$DOTA_{(4)}$). The structure of the obtained compound was investigated by NMR spectroscopy.

Example 30: Coupling HS-($DMA_{(45)}AK_{(4)}$AK-$DOTA_{(4)}$) with MMAE

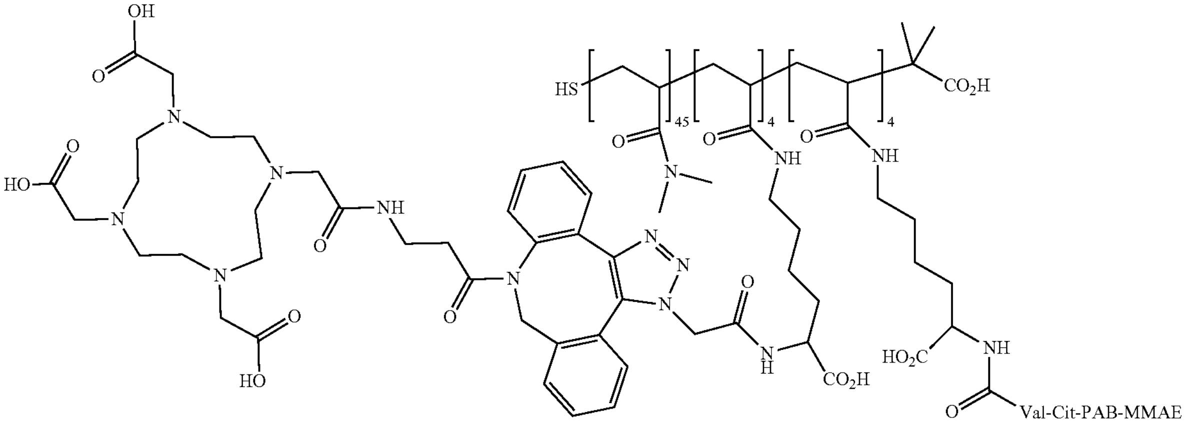

To a solution of HS-($DMA_{(45)}AK_{(4)}$AK-$DOTA_{(4)}$) (14 mg, 1.5 μmol, 1 eq.) in $ddH_2O$ a solution of MMAE-NHS (15.16 mg, 12 μmol, 8 eq.) in DMSO is added and stirred for 24 h at 35° C. The resulting mixture is then dialyzed (MWCO 3.5 kDa) against $ddH_2O$ and the retentate is freeze-dried to obtain HS-($DMA_{(45)}$AK-$MMAE_{(4)}$AK-$DOTA_{(4)}$). The structure of the obtained compound can be investigated by NMR spectroscopy.

Example 31: Synthesis of DBCO-$DMA_{(45)}$AK-$MMAE_{(4)}$AK-$DOTA_{(4)}$)

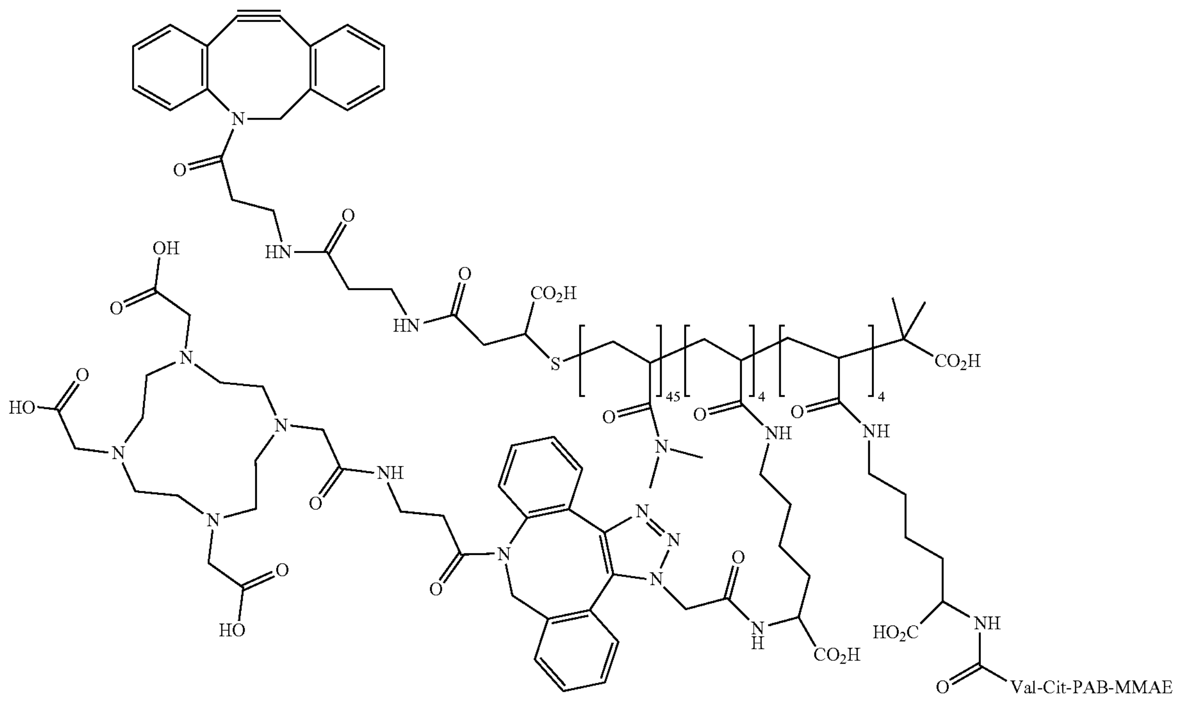

To a solution of HS-($DMA_{(45)}$AK-$MMAE_{(4)}$AK-$DOTA_{(4)}$) (28 mg, 1.8 µmol) in DMF are successively added MC-DBCO (6.1 mg, 14.4 µmol, 8.0 eq.) After 4 h the reaction mixture is diluted with $ddH_2O$ and then dialyzed (MWCO 3.5 kDa) against 0.1 M $NH_4HCO_3$ and the retentate is freeze-dried to obtain DBCO-MC-S-($DMA_{(45)}$AK-$MMAE_{(4)}$AK-$DOTA_{(4)}$. The structure of the obtained compound is investigated by NMR spectroscopy. To verify the activity of the DBCO—group, a small sample of copolymer is dissolved in DMF, FAM-Azide is added, and the mixture is incubated for 4 h at 37° C. Afterward the so functionalized copolymer can be analyzed by GPC using the protocol of example 13 with detection of the RI signal and UV (495 nm). In this test, the signal of 495 nm (FAM) and the RI signal of the copolymer showed a match at the overlay indicating that the copolymer was functionalized with an active DBCO head group.

Example 32: Synthesis of Tetrazine-($DMA_{(45)}$AK-$Azide_{(4)}$)

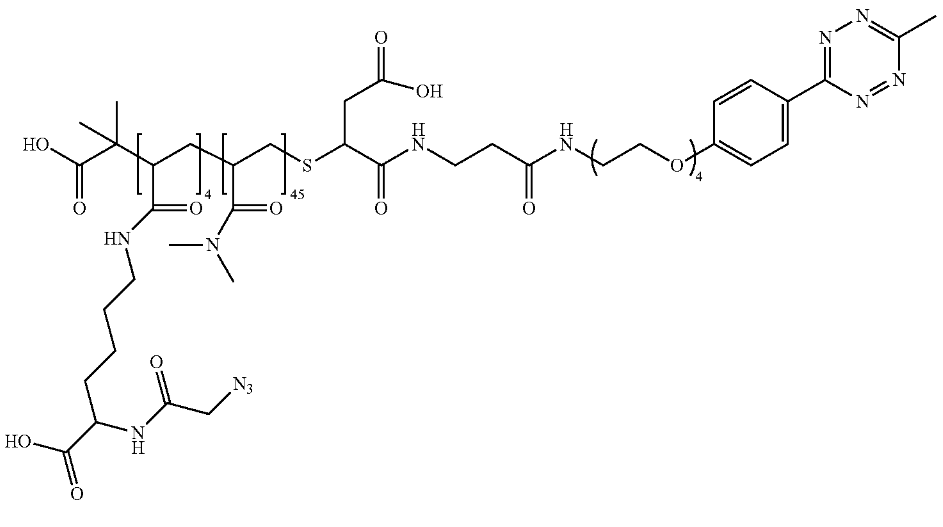

To a solution of HS-($DMA_{(45)}$AK-$Azide_{(4)}$) (1 eq.) in DMF, Tetrazine-$PEG_{(4)}$-MC (8.0 eq.) is added. After 4 h the reaction mixture is diluted with $ddH_2O$ and then dialyzed (MWCO 3.5 kDa) against 0.1 M $NH_4HCO_3$ and the retentate is freeze-dried to obtain Tetrazine-($DMA_{(45)}$AK-$Azide_{(4)}$).

Example 33: Synthesis of Tetrazine-($DMA_{(45)}$AK-$DOTA_{(4)}$AK-$Azide_{(4)}$)

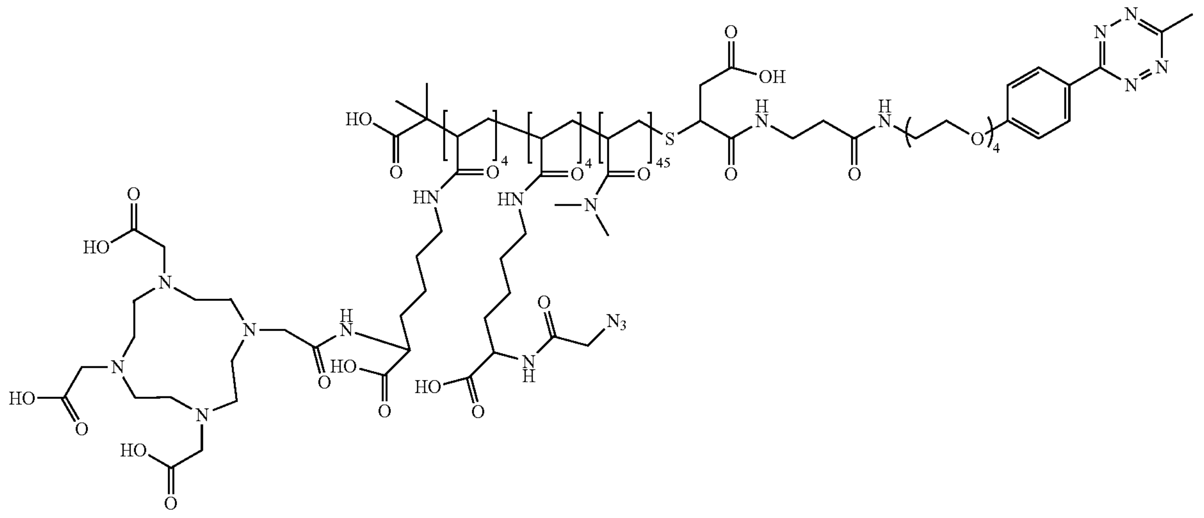

To a solution of HS-($DMA_{(45)}AK_{(4)}$AK-$Azide_{(4)}$) (1 eq.) in $ddH_2O$ a solution of DOTA-NHS (6 μmol, 4 eq.) in DMSO is added, and the mixture is stirred for 24 h at 35° C. The mixture is then dialyzed (MWCO 3.5 kDa) against $ddH_2O$, and the retentate is freeze-dried to obtain HS-($DMA_{(45)}$AK-$DOTA_{(4)}$AK-$Azide_{(4)}$).

To a solution of HS-($DMA_{(45)}$AK-$DOTA_{(4)}$AK-$Azide_{(4)}$) (1 eq.) in DMF Tetrazine-$PEG_{(4)}$-MC (8.0 eq.) is added. After 4 h the reaction mixture is diluted with $ddH_2O$ and then dialyzed (MWCO 3.5 kDa) against 0.1 M $NH_4HCO_3$, and the retentate is freeze-dried to obtain Tetrazine-($DMA_{(45)}$AK-$DOTA_{(4)}$AK-$Azide_{(4)}$)

Example 34: Synthesis of a Radiolabeled Trastuzumab-Azide-Copolymer (Example 17, 24, 32 and 33) Conjugate for Diagnostic and Therapeutic Targeting of Her2 Receptor Overexpressing Cancer Cells The Tetrazine-functionalized copolymer synthesized by one of the procedures presented in example 17, 24, 32 and 33 is conjugated to a cancer cell-specific antibody of the IgG type (e.g. Trastuzumab for targeting Her2+ cancer cells) that has been functionalized with a TCO-group at the glutamine position 295 (Q 295) by a procedure described by Dennler et al. (Bioconjugate Chem. (2014) 25: 569-578) using TCO-$PEG_{(3)}$-amine as substrate.

Briefly, the antibody is deglycosylated by PNGaseF (Merck KGaA, Darmstadt, Germany). A reaction mixture containing 1 unit of enzyme per 10 μg Trastuzumab (Carbosynth Ltd, Berkshir, UK) in PBS (pH 7.4) is incubated overnight at 37° C. in order to activate Q295. Subsequently, deglycosylated Trastuzumab (6.6 μm) in PBS (pH 8) is incubated with TCO-$PEG_{(3)}$-amine (80 molar eq.) and microbial transglutaminase (MTGase) (6 U/mL, Zedira, Darmstadt, Germany) for 16 h at 37° C. After incubation MTGase activity is blocked by the addition of MTGase reactionstopper (Zedira, Darmstadt, Germany). To remove excess TCO-$PEG_{(3)}$-amine, MTGase and residual PNGaseF, the reaction mixture is buffer-exchanged (three times) into $NH_4OAc$ (0.5 m, pH 5.5) by using an Amicon® Ultra 4 mL column (100 kDa MWCO, Merck KGaA, Darmstadt, Germany).

The actual click reaction is subsequently performed by overnight incubation of Trastuzumab-(NH-$PEG_{(3)}$-$TCO)_{(2)}$ with a 3-fold molar excess of Tetrazine-functionalized polymer (Example 17, 24, 32 or 33) at 37° C., yielding Trastuzumab coupled to copolymer synthesized in example 17, 24, 32 and 33. The success of the reaction is investigated by SDS-PAGE using non-modified Trastuzumab as a control. For this, reaction samples (20 μl) are stopped by the addition of 5 μl 4×SDS-PAGE loading buffer +10% w/v β-mercaptoethanol (Biorad, Germany) and incubation at 37° C. for 60 min, with constant shaking at 600 rpm). The samples are subsequently electrophoresed on 4-20% SDS-PAGE gels (Mini-PROTEAN® TGX™ Precast Gels Biorad, Germany) at 150 V for 40 min, and the gels are subjected thereafter to Coomassie blue staining.

Example 35: Loading of Trastuzumab-Azide-Copolymer Conjugates with a Cytotoxic Drug To a solution of Trastuzumab-Azide-Copolymer synthesized according to example 34 in PBS, DBCO-$PEG_{(3)}$-VC-PAB-MMAE (Lucerna-Chem, Lucerne, 3 eq/AK-Azide monomer) is added and the mixture is incubated at 37° C. for 12 hours. The success of the reaction is investigated by SDS-PAGE and GPC according to the procedures presented in the examples above, using non-loaded Trastuzumab-$(Azide\text{-}Copolymer)_2$ as a control.

Example 36: Synthesis of DBCO-$CF_3$ (Model Payload)

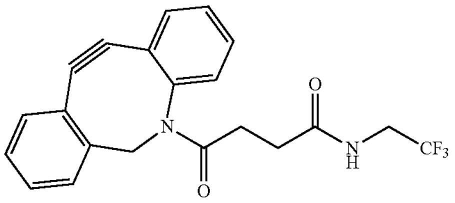 [SMILES: O=C(CCC(=O)N1Cc2ccccc2C#Cc2ccccc21)NCC(F)(F)F]

To a solution of commercially available DBCO-$CO_2H$ (1353016-70-2, 100 mg, 0.328 mmol) in dry DCM (6 mL) were added DIPEA (0.200 mL, 1.146 mmol) and PyBOP (170 mg, 0.328 mmol) at 0° C. The mixture was stirred 30 min at 0° C. and 2,2,2-trifluoroethanamine (0.039 mL, 0.491 mmol) was portionwise added to the mixture. The reaction mixture was then stirred 2 h at 0° C. and with aqueous $KHSO_4$ diluted. The aqueous phase was then extracted with DCM (3x20 mL) and the combined organic phases were washed with brine and dried over $Na_2SO_4$. The volatiles were then removed under reduced pressure and the residue was purified by chromatography column on silica gel using 1.2 Hept/1 EtOAc as eluent. The product was isolated as a white powder (125 mg, 0.324 mmol, 99%).

Example 37: Synthesis of HS-($DMA_{(55)}$-AK-(6-Azidohexanoyl)$_{(4)}$) Via a Polymer-Analogous reaction

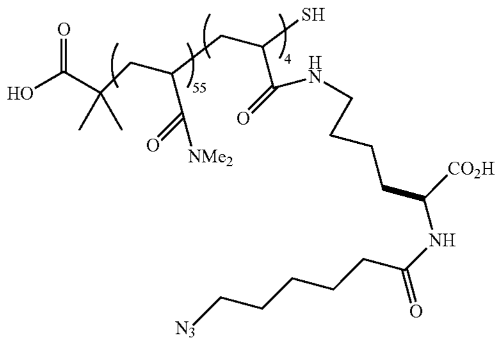

To a solution of HS-($DMA_{(55)}$-$AK_{(4)}$), obtained via the RAFT polymerization (see example 25 for a similar detailed protocol) of DMA (55 eq.) and AK (4 eq.) using Ethyl-RAFT (1 eq.) as a transfer reagent (200 mg, 31 μmol) in DMF (5 mL) were added 1(6-azidohexanoyl)pyrrolidine-2,5-dione (75 mg, 314 μmol) and TEA (44 μL, 314 μmol). The reaction mixture was stirred 16 h at RT, diluted with $ddH_2O$ (12 mL) and dialyzed against $ddH_2O$ (10 L), aqueous $NH_4HCO_3$ (0.1 M, 3 L) and $ddH_2O$ (10 L). The retentate was lyophilized (−78° C., 0.010 mBar). The structure of the obtained construct was investigated by $^1H/^{13}C$-NMR spectroscopy and the DAR (=4.2) was estimated by $^{19}F$-NMR spectroscopy after the derivatization of the titled compound with DBCO-CF3.

Example 38: Synthesis of the Model Compound HS-($DMA_{(55)}$-(AK-Triazin-$CF_3$)$_{(1)}$-(AK-Acetyl-$CF_3$)$_{(3)}$ Via a Polymer-Analogous Reaction

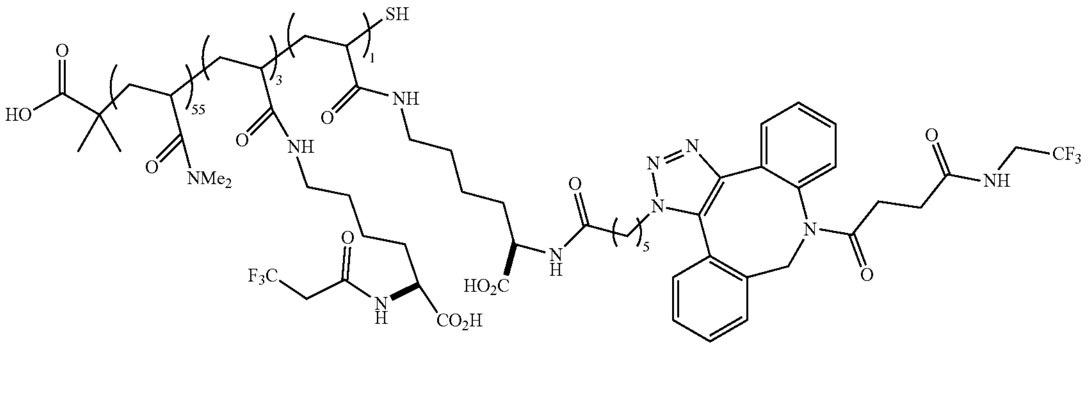

To a solution of HS-($DMA_{(55)}$-AK-$Azide_{(4)}$) in DMF-$D_6$ (0.7 mL) were added 1-(6-azidohexanoyl)pyrrolidine-2,5-dione (5.98 mg, 25 μmol), 1-(3,3,3-trifluoropropanoyl)pyrrolidine-2,5-dione (5.25 mg, 25 μmol) (both substances were added simultaneously) and triethylamine (10.51 μl, 75 μmol). The mixture was stirred 4 h at RT and then DBCO-$CF_3$ (19.40 mg, 50 μmol) was added and the reaction mixture was stirred overnight. The polymer was then purified by ultrafiltration (2000 MWCO, resuspended and filtrated with 3×10 mL $ddH_2O$). The retentate was then lyophilized to obtain a white powder (35 mg, 4.84 μmol, 77%). The white residue was analyzed by $^{19}$F-NMR spectroscopy.

Example 39: Synthesis of the Model Compound Methyltetrazine-PEG4-Succinic Acid-S-($DMA_{(55)}$-(AK-triazin-$CF_3$)$_{(1)}$-(AK-acetyl-$CF_3$)$_{(3)}$

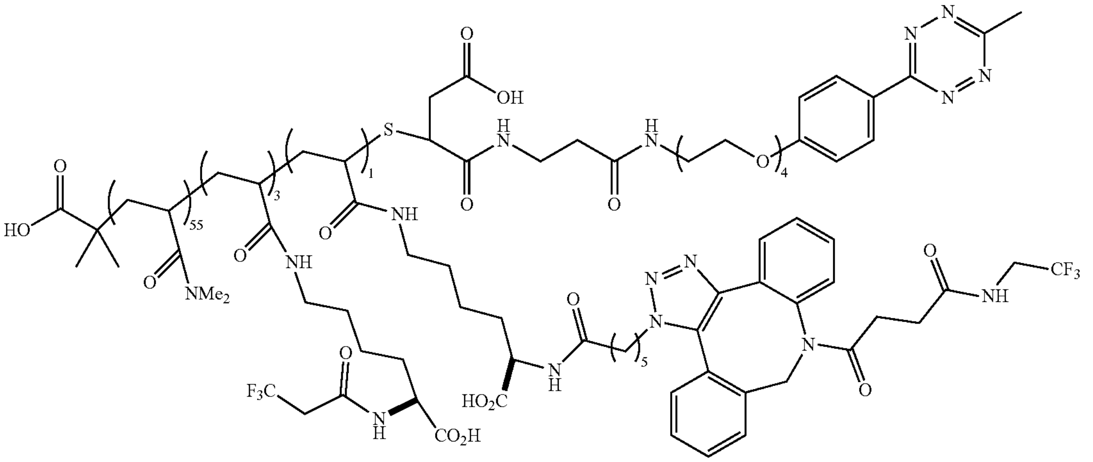

To a solution of HS-($DMA_{(55)}$-(AK-triazin-$CF_3$)$_{(1)}$-(AK-acetyl-$CF_3$)(3) in DMF-$D_6$ (0.7 mL), Tetrazine-$PEG_{(4)}$-MC (8.0 eq.) was added. After 4 h the reaction mixture was diluted with $ddH_2O$ and then dialyzed (MWCO 3.5 kDa) against 0.1 M $NH_4HCO_3$ and the retentate was freeze-dried to obtain Methyltetrazine-$PEG_4$-succinic acid-S-($DMA_{(55)}$-(AK-triazin-$CF_3$)$_{(1)}$-(AK-acetyl-$CF_3$)(3).

Example 40: Synthesis of HS-($HPA_{(55)}$-$AK_{(4)}$)

This compound was obtained analogously to the copolymer HS-($DMA_{(55)}$-AK-$Azide_{(4)}$) (see first part of example 37) using HPA (2-hydroxypropyl)acrylamide) (55 eq.) obtained following the protocol of Fairbanks and coworkers (dx.doi.org/10.1021/bm500654q) as an alternative to DMA monomer.

Example 41: Synthesis of HS-($HEAa_{53)}$ $AK_{(4)}$)

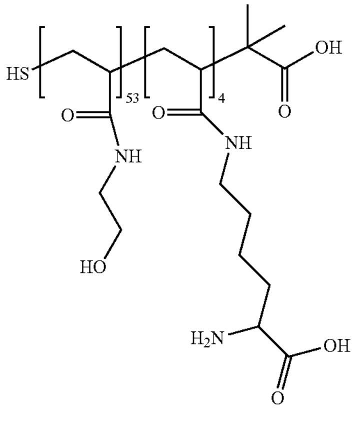

To a solution of HEAa (368 μL, 3540 μmol, 53 eq.), AK (54 mg, 267 μmol, 4 eq.) in $ddH_2O$ were successively added Ethyl-RAFT (see example 11) (15 mg, 67 μmol, 1.0 eq.) and VA044 (6.5 mg, 20 μmol, 0.3 eq.). The reaction mixture was stirred for 4 h at 60° C. The reaction mixture was stirred for 4 h at room temperature. Cyclohexylamine (1533 μL, 13.37 mmol, 200 eq.) was added to the reaction mixture and stirred for 3 h at 30° C. The resulting mixture was then dialyzed (MWCO 3.5 kDa) against $ddH_2O$ and the retentate was freeze-dried to obtain HS-($HEAa_{(53)}$ $AK_{(4)}$) as a white powder (395 mg, 55.6 μmol, 83% over three steps). The structure of the obtained compound was investigated by NMR spectroscopy and GPC using the protocol of example 13.

Further aspects and/or embodiments of the invention are disclosed in the following numbered items.

1. A copolymer containing multiple copies of a first payload molecule made by (a) polymerization of a reaction mixture comprising (1) a co-principal monomer of formula I containing an azide moiety, (I)

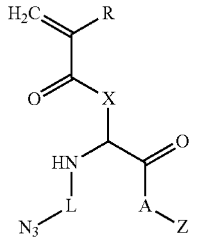

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—$CH(CH_3)$—, —S—$CH_2$— or —NH—$C_6H_4$—$CH_2$—; Z is H (if A is —O—) or —$C_nH_{2n+1}$ (with n=1-8); and A is —O— or —NH—; L is a linker/spacer which can be cleavable or non-cleavable under physiological conditions, (2) a polymerizable principal monomer, which monomer is characterized as having at least one vinylic group and not containing an amino acid moiety or an azide moiety, and (3) an initiator system for generating free radical species, the polymerization yielding a copolymer; and (b) coupling of the first payload molecules to the azide moieties contained in the copolymer of step (a).

2. The copolymer of any of item 1, wherein the reaction mixture further includes a co-principal monomer of one or both of formula II, (II)

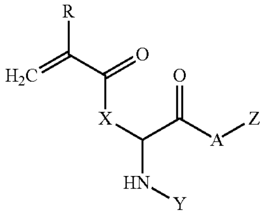

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—$CH(CH_3)$—, —S—$CH_2$— or —NH—$C_6H_4$—$CH_2$—; Y is H or —CO—$C_nH_{2n+1}$ (with n=1-8); Z is H (if A is —O—) or —$C_nH_{2n+1}$ (with n=1-8); and A is —O— or —NH—, or of formula III, (III)

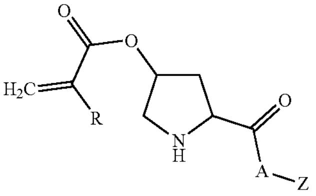

wherein: R is —H, —$CH_3$, —$CH_2$—$CH_3$ or —$(CH_2)_2$—$CH_3$; Z is H (if A is O) or —$C_nH_{2n+1}$ (with n=1-8); and A is —O— or —NH—.

3. The copolymer of item 2, wherein subsequent to step (a) or (b) a further step comprises coupling reactive group-containing second payload molecules to the co-principal monomers of one or both formulae II or III whereby either one or both of Y and Z in the monomers of formula II is H or Z in the monomers of formula III is H.

4. The copolymer of any of items 1-3, wherein the reaction mixture further includes a RAFT reagent for controlling the copolymerization.

5. The copolymer of item 4, wherein step (a) is divided into two successive polymerization reactions, wherein the first polymerization reaction is carried out in a first reaction mixture comprising a polymerizable principal monomer not containing an amino acid moiety or an azide moiety, a RAFT agent for controlling the copolymerization, and an initiator system for generating free radical species, the polymerization yielding a RAFT pre-polymer, and wherein the second polymerization reaction is carried out in a second reaction mixture comprising the RAFT pre-polymer of the first polymerization reaction, a co-principle monomer of formulae I and an initiator system for generating free radical species.

6. The copolymer of item 5 wherein the second reaction mixture further comprises a co-principal monomer of one or both of formulae II and III and a polymerizable principal monomer not containing an amino acid moiety or an azide moiety.

7. The copolymer of any of item 4-6, wherein the RAFT agent contains a reactive group or is converted to provide a reactive group subsequent to step (a).

8. The copolymer of item 4-7, wherein the RAFT agent contains a monodisperse spacer of 2-30 units.

9. The copolymer of any of items 7-8, wherein prior to step (b), a cell type-specific or tissue type-specific targeting moiety is coupled to said reactive group.

10. The copolymer of any of items 7-8, wherein subsequent to step (b), a cell type-specific or tissue type-specific targeting moiety is coupled to said reactive group.

11. The copolymer of any of items 1-10, wherein the first payload molecule is a chelating agent, the copolymer is exposed to an active agent and the active agent is captured by the chelating agent.

12. The copolymer of any of items 1-11, wherein the copolymer has an average molecular weight of 5,000 Daltons to 80,000 Daltons.

13. The copolymer of any of items 1-11, wherein the copolymer has an average molecular weight of 5,000 Daltons to 40,000 Daltons.

14. The copolymer of any of items 1-11, wherein the copolymer has an average molecular weight of 5,000 Daltons to 20,000 Daltons.

15. The copolymer of item 1, wherein the reaction mixture contains (1) a co-principal monomer of formula I, (2) a polymerizable principal monomer, which monomer is characterized as having at least one vinylic group and not containing an amino acid moiety or an azide moiety, (3) optionally, an agent for controlling radical polymerization, and (3) an initiator system for generating free radical species; and the copolymer contains 2-12 molecules of the co-principal monomer of formula I.

16. The copolymer of item 15, wherein the copolymer contains 2-8 molecules of a co-principal monomer of formula I.

17. The copolymer of item 15, wherein the copolymer contains 2-6 molecules of a co-principal monomer of formula I.

18. The copolymer of item 2, wherein the reaction mixture contains (1) a co-principal monomer of formula I, (2) a co-principal monomer of one or both formulae II or III, (3) a polymerizable principal monomer, which monomer is characterized as having at least one vinylic group and not containing an amino acid moiety or an azide moiety, (4) optionally, an agent for controlling radical polymerization, and (5) an initiator system for generating free radical species; and the copolymer contains 10-50 molecules of any of the co-principal monomers of formulae I-III.

19. The copolymer of item 18, wherein the copolymer contains 10-40 molecules of any of the co-principal monomers of formulae I-III.

20. The copolymer of item 18, wherein the copolymer contains 10-30 molecules of any of the co-principal monomers of formulae I-III.

21. The copolymer of item 3, wherein the reaction mixture contains (1) a co-principal monomer of formula I, (2) a co-principal monomer of one or both formulae II or III, (3) a polymerizable principal monomer, which monomer is characterized as having at least one vinylic group and not containing an amino acid moiety or an azide moiety, (4) optionally, an agent for controlling radical polymerization, and (5) an initiator system for generating free radical species, the polymerization yielding a copolymer; and the copolymer contains 4-20 molecules of any of the co-principal monomers of formulae I-III.

22. The copolymer of item 18, wherein the copolymer contains 4-15 molecules of any of the co-principal monomers of formulae I-III.

23. The copolymer of item 18, wherein the copolymer contains 4-10 molecules of any of the co-principal monomers of formulae I-III.

24. A pharmaceutical composition comprising an effective amount of a copolymer according to any of items 1-23 and a pharmaceutically acceptable carrier or excipient.

25. Use of the pharmaceutical composition of item 24 for the treatment of a cancer or another disease or condition in a subject, comprising administering the pharmaceutical composition to the subject.

Further aspects and/or embodiments of the invention are disclosed in the following numbered paragraphs.

1. A copolymer containing multiple copies of a first payload molecule made by (a) polymerization of a reaction mixture comprising (1) a co-principal monomer of formula I, (II)

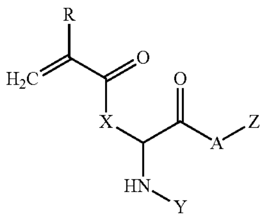

wherein R is —H, —$CH_3$, —$CH_2$—$CH_3$ or —$(CH_2)_2$—$CH_3$; X is —$NH(CH_2)_4$—, —$NH(CH_2)_3$—, —O—$CH_4$—$CH_2$—, —O—$CH_2$—, —O—$CH(CH_3)$—, —S—$CH_2$— or —NH—$CH_4$—$CH_2$—; Y is H; Z is H (if A is —O—) or —$C_nH_{2n+1}$ (with n=1-8); and A is —O— or —NH—, (2) a polymerizable principal monomer, which monomer is characterized as having at least one vinylic group and not containing an amino acid moiety or an azide moiety, (3) optionally a RAFT reagent for controlling the copolymerization, and (4) an initiator system for generating free radical species, the polymerization yielding a copolymer; and (b) treating the copolymer of step (a) with an amine reactive agent containing a linker and an azide moiety, and (c) coupling of the first payload molecules to the azide moieties contained in the copolymer of step (b).

2. The copolymer of paragraph 1, wherein the reaction mixture further includes a co-principal monomer of formula III, (III)

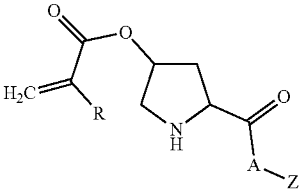

wherein: R is —H, —$CH_3$, —$CH_2$—$CH_3$ or —$(CH_2)_2$—$CH_3$; Z is H (if A is O) or —$C_nH_{2n+1}$ (with n=1-8); and A is —O— or —NH—.

3. The copolymer of paragraph 1 or 2, wherein L is —CO—$C_nH_{2n}$ (with n=1-10) or —CO-$PEG_n$(with n=1-14), or wherein L is —CO-valine-citrulline-PABC or variants thereof, valine-lysine, valine-alanine, valine-arginine, glutamate-valine-citrulline.

4. The copolymer of any one of paragraphs 1 to 3, wherein the polymerizable principal monomer is N,N-dimethyl-acrylamide, N-isobutyl-acrylamide, N-tert. butyl-acrylamide, N-hydroxyethyl-acrylamide, N-(2-Hydroxypropyl)-acrylamide, N-(3-Hydroxypropyl)-acrylamide, N-(3-Hydroxypropyl)-methacrylamide, N-(2-Hydroxypropyl)-methacrylamide, N-(3-Aminopropyl)-acrylamide hydrochloride, or N-(3-Aminopropyl)-methacrylamide hydrochloride, or wherein the polymerizable principal monomer is methacrylic acid, 2-hydroxyethyl-acrylate, 2-hydroxypropyl-acrylate, 3-hydroxypropyl-acrylate, 2-hydroxy-1-methyl-ethyl-acrylate, 2-aminoethyl acrylate hydrochloride, 3-hydroxypropyl-methacrylate, 2-hydroxy-1-methylethylmethacrylate, 2-hydroxyethyl-methacrylate, 2-hydroxypropyl-methacrylate or 2-aminoethyl methacrylate hydrochloride.

5. A copolymer comprising a repeating unit of a formula (R1a)

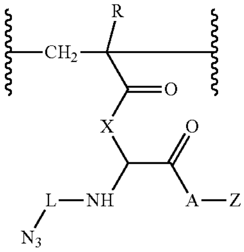

wherein R is —H, —$CH_3$, —$CH_2$—$CH_3$ or —$(CH_2)_2$—$CH_3$; X is —$NH(CH_2)_4$—, —$NH(CH_2)_3$—, —O—$CH_4$—$CH_2$—, —O—$CH_2$—, —O—$CH(CH_3)$—, —S—$CH_2$— or —NH—$CH_4$—$CH_2$—; Z is H (if A is —O—) or —$C_nH_{2n+1}$ (with n=1-8); and A is —O— or —NH—; L is a linker/spacer which can be cleavable or non-cleavable under physiological conditions.

6. A copolymer comprising a repeating unit of a formula:

(R1)

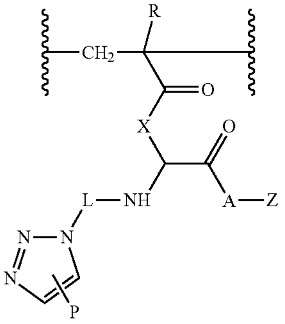

wherein R is —H, —$CH_3$, —$CH_2$—$CH_3$ or —$(CH_2)_2$—$CH_3$; X is —$NH(CH_2)_4$—, —$NH(CH_2)_3$—, —O—$CH_4$—$CH_2$—, —O—$CH_2$—, —O—$CH(CH_3)$—, —S—$CH_2$— or —NH—$CH_4$—$CH_2$—; Z is H (if A is —O—) or —$C_nH_{2n+1}$ (with n=1-8); and A is —O— or —NH—; L is a linker/spacer which can be cleavable or non-cleavable under physiological conditions, and P comprises the first payload molecule.

7. The copolymer of paragraph 5 or 6, further comprising a repeating unit of a formula:

(R2)

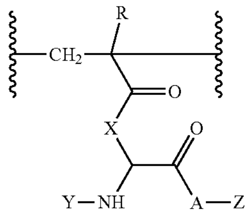

wherein R is —H, —$CH_3$, —$CH_2$—$CH_3$ or —$(CH_2)_2$—$CH_3$; X is —$NH(CH_2)_4$—, —$NH(CH_2)_3$—, —O—$CH_4$—$CH_2$—, —O—$CH_2$—, —O—$CH(CH_3)$—, —S—$CH_2$— or —NH—$CH_4$—$CH_2$—; Y is H or —CO—$C_nH_{2n+1}$ (with n=1-8); Z is H (if A is —O—) or —$C_nH_{2n+1}$ (with n=1-8); and A is —O— or —NH—, and/or a repeating unit of a formula:

(R3)

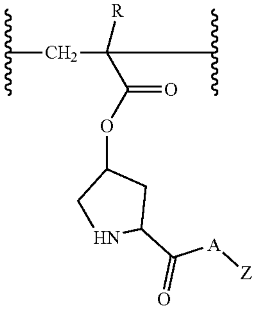

wherein: R is —H, —$CH_3$, —$CH_2$—$CH_3$ or —$(CH_2)_2$—$CH_3$; Z is H (if A is O) or —$C_nH_{2n+1}$ (with n=1-8); and A is —O— or —NH—.

8. The copolymer of paragraph 7, wherein Y is H and/or Z is H.

9. The copolymer of paragraph 7, wherein Y and/or Z comprises a second payload molecule.

10. The copolymer of any one of paragraphs 5 to 9, wherein L is —CO—$C_nH_{2n}$ (with n=1-10) or —CO-$PEG_n$ (with n=1-14), or wherein L is —CO-valine-citrulline-PABC or variants thereof, valine-lysine, valine-alanine, valine-arginine, glutamate-valine-citrulline.

11. The copolymer of any one of paragraphs 5 to 10, further comprising a repeating unit obtained through polymerization of N,N-dimethyl-acrylamide, N-isobutyl-acrylamide, N-tert. butyl-acrylamide, N-hydroxyethyl-acrylamide, N-(2-Hydroxypropyl)-acrylamide, N-(3-Hydroxypropyl)-acrylamide, N-(3-Hydroxypropyl)-methacrylamide, N-(2-Hydroxypropyl)-methacrylamide, N-(3-Aminopropyl)-acrylamide hydrochloride, or N-(3-Aminopropyl)-methacrylamide hydrochloride, or a repeating unit obtained through polymerization of methacrylic acid, 2-hydroxyethyl-acrylate, 2-hydroxypropyl-acrylate, 3-hydroxypropyl-acrylate, 2-hydroxy-1-methylethyl-acrylate, 2-aminoethyl acrylate hydrochloride, 3-hydroxypropyl-methacrylate, 2-hydroxy-1-methylethyl-methacrylate, 2-hydroxyethyl-methacrylate, 2-hydroxypropyl-methacrylate or 2-aminoethyl methacrylate hydrochloride.

12. The copolymer of any one of paragraphs 6 to 11, wherein the repeating units of formulae (R2) and (R3) are absent, the average number of repeating units according to formula (R1) is 2 to 12, preferably 2 to 8, more preferably 1 to 6.

13. The copolymer of any one of paragraphs 5 to 11, wherein the repeating units of formulae (R2) or (R3) are not functionalized, and wherein the average number of repeating units according to formulae (R1), (R2) or (R3) is 10 to 50, preferably 10 to 40, more preferably 10 to 30.

14. The copolymer of any one of paragraphs 5 to 11, wherein the repeating units of formulae (R2) or (R3) are functionalized with a second payload molecule, and wherein the average number of repeating units according to formulae (R1), (R2) or (R3) is 4 to 20, preferably 4 to 15, more preferably 4 to 10

The invention claimed is:

1. A copolymer containing multiple copies of a first payload molecule, wherein the copolymer is obtainable by (a) polymerization of a reaction mixture comprising (1) a monomer of formula I containing an azide moiety, (I)

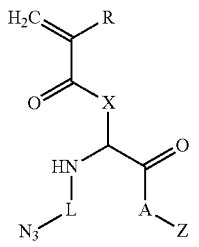

wherein R is —H, $—CH_3$, $—CH_2—CH_3$ or $—(CH_2)_2—CH_3$; X is $—NH(CH_2)_4—$, $—NH(CH_2)_3—$, $—O—C_6H_4—CH_2—$, $—O—CH_2—$, $—O—CH(CH_3)—$, $—S—CH_2—$ or $—NH—C_6H_4—CH_2—$; Z is H or $—C_nH_{2n+1}$ wherein n=1-8; and A is —O— or —NH—; L is a linker/spacer, (2) a monomer having at least one vinylic group and not containing an amino acid moiety or an azide moiety, and (3) an initiator system for generating free radical species, the polymerization yielding a copolymer; and (b) coupling of the first payload molecules to the azide moieties contained in the copolymer of step (a);

wherein said first payload molecule is a cytotoxic substance or chelating agent.

2. The copolymer of any of claim 1, wherein the reaction mixture further includes a monomer of one or both of formula II or formula III, wherein (II)

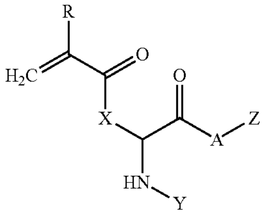

wherein R is —H, $—CH_3$, $—CH_2—CH_3$ or $—(CH_2)_2—CH_3$; X is $—NH(CH_2)_4—$, $—NH(CH_2)_3—$, $—O—C_6H_4—CH_2—$, $—O—CH_2—$, $—O—CH(CH_3)—$, $—S—CH_2—$ or $—NH—C_6H_4—CH_2—$; Y is H or $—CO—C_nH_{2n+1}$ wherein n=1-8; Z is H or $—C_nH_{2n+1}$ wherein n=1-8; and A is —O— or —NH—, and wherein (III)

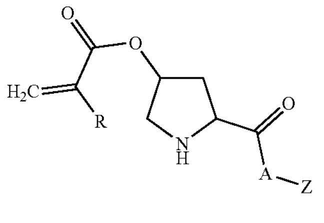

wherein R is —H, $—CH_3$, $—CH_2—CH_3$ or $—(CH_2)_2—CH_3$; Z is H or $—C_nH_{2n+1}$ wherein n=1-8; and A is —O— or —NH—.

3. The copolymer of claim 2, wherein subsequent to step (a) or (b) a further step comprises coupling reactive group-containing second payload molecules to the monomers of one or both formulae II or III wherein either one or both of Y and Z in the monomers of formula II is H or Z in the monomers of formula III is H.

4. The copolymer of claim 1, wherein the reaction mixture further includes a reversible addition-fragmentation chain transfer reagent (RAFT agent) for controlling the copolymerization.

5. The copolymer of claim 4, wherein step (a) is divided into two successive polymerization reactions, wherein the first polymerization reaction is carried out in a first reaction mixture comprising a monomer having at least one vinylic group and not containing an amino acid moiety or an azide moiety, a RAFT agent for controlling the copolymerization, and an initiator system for generating free radical species, the polymerization yielding a RAFT pre-polymer, and wherein the second polymerization reaction is carried out in a second reaction mixture comprising the RAFT pre-polymer of the first polymerization reaction, a monomer of formulae I and an initiator system for generating free radical species.

6. The copolymer of claim 5, wherein the second reaction mixture further comprises a monomer of one or both of formulae II and III and a monomer having at least one vinylic group and not containing an amino acid moiety or an azide moiety.

7. The copolymer of claim 4, wherein the RAFT agent contains a reactive group or is converted to provide a reactive group subsequent to step (a), or wherein the RAFT agent contains a monodisperse spacer of 2-30 units.

8. The copolymer of claim 7, wherein prior to step (b), a cell type-specific or tissue type-specific targeting moiety is coupled to said reactive group, or wherein subsequent to step (b), a cell type-specific or tissue type-specific targeting moiety is coupled to said reactive group;

wherein said cell type-specific or tissue type-specific targeting moiety is a molecule that binds to a surface marker on cells and is selected from the group consisting of a monoclonal antibody, a single-domain, variable fragment of an antibody chain, a single-chain antibody, a DARPin (Designed Ankyrin Repeat Protein), a DNA- or RNA-based aptamer, a peptide-based aptamer, a peptide or protein capable of binding a cell surface marker, a hormone, and a small molecule capable of binding a cell surface marker.

9. A copolymer containing multiple copies of a first payload molecule obtainable by (a) polymerization of a reaction mixture comprising (1) a monomer of formula II, (II)

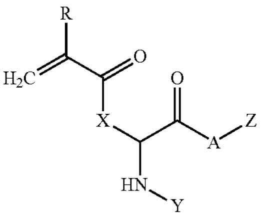

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—$CH(CH_3)$—, —S—$CH_2$— or —NH—$C_6H_4$—$CH_2$—; Y is H; Z is H or —$C_nH_{2n+1}$ wherein n=1-8; and A is —O— or —NH—, (2) a monomer having at least one vinylic group and not containing an amino acid moiety or an azide moiety, and (3) an initiator system for generating free radical species, the polymerization yielding a copolymer;

(b) treating the copolymer of step (a) with an amine reactive agent containing a linker/spacer L and an azide moiety, and (c) coupling of the first payload molecules to the azide moieties contained in the copolymer of step (b);

wherein said first payload molecule is a cytotoxic substance or chelating agent.

10. The copolymer of claim 9, wherein the reaction mixture further includes a monomer of formula III,

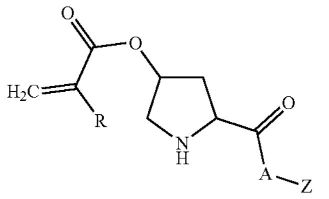

(III)

wherein: R is —H, —$CH_3$, —$CH_2$—$CH_3$ or —$(CH_2)_2$—$CH_3$; Z is H or —$C_nH_{2n+1}$ (with n=1-8); and A is —O— or —NH—, optionally wherein a further step comprises coupling reactive group-containing second payload molecules to the monomers of III wherein Z in the monomers of formula III is H.

11. The copolymer of claim 1, wherein the first payload molecule is a chelating agent, the copolymer is exposed to an active agent and the active agent is captured by the chelating agent.

12. The copolymer of claim 1, wherein the copolymer has an average molecular weight of 5,000 Daltons to 80,000 Daltons, or wherein the copolymer has an average molecular weight of 5,000 Daltons to 40,000 Daltons, or wherein the copolymer has an average molecular weight of 5,000 Daltons to 20,000 Daltons.

13. The copolymer of claim 1, wherein the reaction mixture contains (1) a monomer of formula I, (2) a monomer having at least one vinylic group and not containing an amino acid moiety or an azide moiety, (3) optionally, an agent for controlling radical polymerization, and (4) an initiator system for generating free radical species; and the copolymer contains 2-12 molecules of the monomer of formula I.

14. The copolymer of claim 13, wherein the copolymer contains 2-8 molecules of the monomer of formula I, or wherein the copolymer contains 2-6 molecules of the monomer of formula I.

15. The copolymer of claim 2, wherein the reaction mixture contains (1) a monomer of formula I, (2) a monomer of one or both formulae II or III, (3) a monomer having at least one vinylic group and not containing an amino acid moiety or an azide moiety, (4) optionally, an agent for controlling radical polymerization, and (5) an initiator system for generating free radical species; and the copolymer contains 10-50 molecules of any of the monomers of formulae I-III.

16. The copolymer of claim 15, wherein the copolymer contains 10-40 molecules of any of the monomers of formulae I-III, or wherein the copolymer contains 10-30 molecules of any of the monomers of formulae I-III.

17. The copolymer of claim 3, wherein the reaction mixture contains (1) a co-principal monomer of formula I, (2) a co-principal monomer of one or both formulae II or III, (3) a monomer having at least one vinylic group and not containing an amino acid moiety or an azide moiety, (4) optionally, an agent for controlling radical polymerization, and (5) an initiator system for generating free radical species, the polymerization yielding a copolymer; and the copolymer contains 4-20 molecules of any of the monomers of formulae I-III.

18. The copolymer of claim 17, wherein the copolymer contains 4-15 molecules of any of the monomers of formulae I-III, or wherein the copolymer contains 4-10 molecules of any of the monomers of formulae I-III.

19. The copolymer of claim 1, wherein L is —CO—$C_nH_{2n}$—, wherein n=1-10, or —CO-$(PEG)_n$-, wherein n=1-14; or wherein L is —CO-valine-citrulline-PABC, wherein PABC is p-aniline-beta-carbamate, or variants thereof, valine-lysine, valine-alanine, valine-arginine, glutamate-valine-citrulline, and/or wherein the monomer having at least one vinylic group and not containing an amino acid moiety or an azide moiety is N,N-dimethyl-acrylamide, N-isobutyl-acrylamide, N-tert. Butyl-acrylamide, N-hydroxyethyl-acrylamide, N-(2-hydroxypropyl)-acrylamide, N-(3-hydroxypropyl)-acrylamide, N-(3-hydroxypropyl)-methacrylamide, N-(2-hydroxypropyl)-methacrylamide, N-(3-aminopropyl)-acrylamide hydrochloride, or N-(3-aminopropyl)-methacrylamide hydrochloride; or wherein the monomer having at least one vinylic group and not containing an amino acid moiety or an azide moiety is meth-acrylic acid, 2-hydroxyethyl-acrylate, 2-hydroxypropyl-acrylate, 3-hydroxypropyl-acrylate, 2-hydroxy-1-methylethyl-acrylate, 2-aminoethyl acrylate hydrochloride, 3-hydroxypropyl-methacrylate, 2-hydroxy-1-methylethyl-methacrylate, 2-hydroxyethyl-methacrylate, 2-hydroxypropyl-methacrylate or 2-aminoethyl methacrylate hydrochloride.

20. A copolymer comprising an optional repeating unit of formula (R1a)

(R1a)

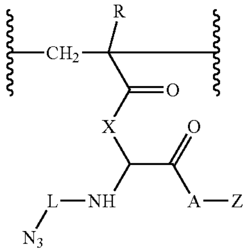

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—CH($CH_3$)—, —S—$CH_2$— or —NH—$C_6H_4$—$CH_2$—; Z is H or —$C_nH_{2n+1}$ (with n=1-8); and A is —O— or —NH—, L is a linker/spacer, or a repeating unit of a formula (R1)

(R1)

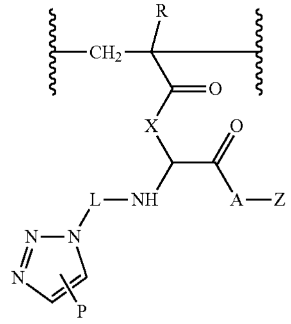

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—CH($CH_3$)—, —S—$CH_2$— or —NH—$C_6H_4$—$CH_2$—; Z is H or —$C_nH_{2n+1}$ (with n=1-8); and A is —O— or —NH—; L is a linker/spacer, and P comprises a first payload molecule; wherein said first payload molecule is a cytotoxic substance or chelating agent.

21. The copolymer of claim 20, further comprising a repeating unit of formula (R2):

(R2)

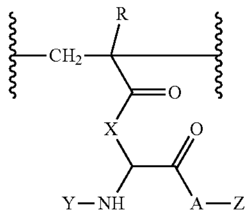

wherein R is —H, —$CH_3$, —$CH_2$—$CH_3$ or —$(CH_2)_2$—$CH_3$; X is —$NH(CH_2)_4$—, —$NH(CH_2)_3$—, —O—$C_6H_4$—$CH_2$—, —O—$CH_2$—, —O—CH($CH_3$)—, —S—$CH_2$— or —NH—$C_6H_4$—$CH_2$—; Y is H or —CO—$C_nH_{2n+1}$ (with n=1-8) or Y comprises a second payload molecule; Z is H or —$C_nH_{2n+1}$ (with n=1-8), or Z comprises a second payload molecule; and A is —O— or —NH—, and/or a repeating unit of formula (R3):

(R3)

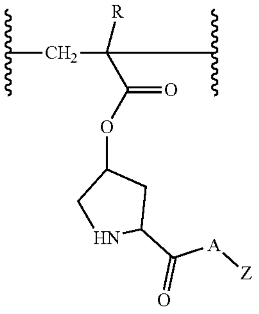

wherein: R is —H, —$CH_3$, —$CH_2$—$CH_3$ or —$(CH_2)_2$—$CH_3$; Z is H or —$C_nH_{2n+1}$ (with n=1-8), or Z comprises a second payload molecule; and A is —O— or —NH—.

22. The copolymer of claim 21, wherein Y is H and/or Z is H, or wherein Y and/or Z comprises a second payload molecule.

23. The copolymer of claim 20, wherein L is —CO—$C_nH_{2n}$— (with n=1-10) or —CO-$(PEG)_n$- (with n=1-14), or wherein L is —CO-valine-citrulline-PABC, wherein PABC represents p-aniline-beta-carbamate, or variants thereof, valine-lysine, valine-alanine, valine-arginine, glutamate-valine-citrulline.

24. The copolymer of claim 20, further comprising a repeating unit obtainable by polymerization of N,N-dimethyl-acrylamide, N-isobutyl-acrylamide, N-tert. butyl-acrylamide, N-hydroxyethyl-acrylamide, N-(2-hydroxypropyl)-acrylamide, N-(3-hydroxypropyl)-acrylamide, N-(3-hydroxypropyl)-methacrylamide, N-(2-hydroxypropyl)-methacrylamide, N-(3-aminopropyl)-acrylamide hydrochloride, or N-(3-aminopropyl)-methacrylamide hydrochloride, or a repeating unit obtained through polymerization of methacrylic acid, 2-hydroxyethyl-acrylate, 2-hydroxypropyl-acrylate, 3-hydroxypropyl-acrylate, 2-hydroxy-1-methylethyl-acrylate, 2-aminoethyl acrylate hydrochloride, 3-hydroxypropyl-methacrylate, 2-hydroxy-1-methylethyl-methacrylate, 2-hydroxyethyl-methacrylate, 2-hydroxypropyl-methacrylate or 2-aminoethyl methacrylate hydrochloride.

25. The copolymer of claim 20, wherein the repeating units of formulae (R2) and (R3) are absent, and the average number of repeating units according to formula (R1) per molecule of copolymer is 2 to 12, preferably 2 to 8, more preferably 2 to 6.

26. The copolymer of claim 20, wherein the repeating units of formulae (R2) or (R3) are not functionalized, and wherein the average number of repeating units according to formulae (R1), (R2) or (R3) per molecule of copolymer is 10 to 50.

27. The copolymer of a claim 20, wherein the repeating units of formulae (R2) or (R3) are functionalized with a second payload molecule, and wherein the average number of repeating units according to formulae (R1), (R2) or (R3) per molecule of copolymer is 4 to 20.

28. A pharmaceutical composition comprising an effective amount of a copolymer according to claim 1 and a pharmaceutically acceptable carrier or excipient.

29. A method for the treatment of a cancer or another disease or condition in a subject, or the diagnosis thereof, comprising administering the pharmaceutical composition of claim 28 to the subject.

30. The method of claim 29, wherein said subject has cancer and said administration of said pharmaceutical composition is cancer treatment therapy.

31. The method of claim 30, wherein the copolymer comprises a first payload molecule and a second payload molecule, and wherein the first payload molecule and a second payload molecule are two active agents to be administered together as a combination therapy.

32. The method of claim 29, wherein said administration of said pharmaceutical composition is for a diagnostic application.

33. The method of claim 32, wherein the diagnostic application is monitoring of cancer.

34. The method of claim 33, wherein the monitoring of cancer is performed simultaneously with cancer therapy.

35. The method of claim 32, wherein the copolymer comprises a radionuclide useful in diagnosis.

* * * * *